(12) United States Patent
Levesque et al.

(10) Patent No.: US 10,687,526 B2
(45) Date of Patent: *Jun. 23, 2020

(54) GAS DEPLETION AND GAS ADDITION DEVICES FOR BLOOD TREATMENT

(71) Applicant: Hemanext Inc., Lexington, MA (US)

(72) Inventors: Steven F. Levesque, North Pembroke, MA (US); Thomas R. Ruth, South Easton, MA (US)

(73) Assignee: Hemanext Inc., Lexington, MA (US)

( * ) Notice: Subject to any disclaimer, the term of this patent is extended or adjusted under 35 U.S.C. 154(b) by 120 days.

This patent is subject to a terminal disclaimer.

(21) Appl. No.: 15/842,824

(22) Filed: Dec. 14, 2017

(65) Prior Publication Data

US 2018/0153157 A1   Jun. 7, 2018

Related U.S. Application Data

(63) Continuation of application No. 14/771,438, filed as application No. PCT/US2014/019537 on Feb. 28, 2014, now Pat. No. 9,877,476.

(60) Provisional application No. 61/770,516, filed on Feb. 28, 2013.

(51) Int. Cl.
*A01N 1/02*   (2006.01)
*B01D 19/00*   (2006.01)
*A61M 1/02*   (2006.01)

(52) U.S. Cl.
CPC ......... *A01N 1/0242* (2013.01); *A01N 1/0263* (2013.01); *B01D 19/0031* (2013.01); *A61M 1/0281* (2013.01); *B01D 2257/104* (2013.01)

(58) Field of Classification Search
CPC .......... B01D 19/0031; B01D 2257/504; B01D 2311/13; A01N 1/0242; A01N 1/0263; A61M 1/0281; A61M 1/1698
See application file for complete search history.

(56) References Cited

U.S. PATENT DOCUMENTS

| 3,064,647 A | 11/1962 | Earl |
| 3,361,041 A | 1/1968 | Grob |
| 3,668,837 A | 6/1972 | Gross |

(Continued)

FOREIGN PATENT DOCUMENTS

| CA | 2477946 | 9/2003 |
| CN | 1195965 A | 10/1998 |

(Continued)

OTHER PUBLICATIONS

Extended European Search Report dated Apr. 16, 2019, in European Patent Application No. 16845192.0.

(Continued)

*Primary Examiner* — Jason M Greene
(74) *Attorney, Agent, or Firm* — Arnold & Porter Kaye Scholer LLP

(57) ABSTRACT

Devices for the preparation of depleted blood products that provide for the depletion of oxygen, carbon dioxide, or oxygen and carbon dioxide are described. In addition, devices for the replenishment of oxygen and other gases to an anaerobic blood product are described. Methods and systems incorporating depletion and addition devices are provided to optimize the preparation, storage and transfusion of blood products to a recipient are described.

19 Claims, 18 Drawing Sheets

(56) References Cited

U.S. PATENT DOCUMENTS

| | | | |
|---|---|---|---|
| 3,668,838 A | 6/1972 | McNeil et al. | |
| 3,803,810 A | 4/1974 | Rosenberg | |
| 3,910,841 A | 10/1975 | Esmond | |
| 3,942,529 A | 3/1976 | Waage | |
| 4,075,091 A * | 2/1978 | Bellhouse | B01D 63/08 |
| | | | 210/637 |
| 4,086,924 A | 5/1978 | Latham, Jr. | |
| 4,093,515 A | 6/1978 | Kolobow | |
| 4,131,200 A | 12/1978 | Rinfret | |
| 4,162,676 A | 7/1979 | Talcott | |
| 4,222,379 A | 9/1980 | Smith | |
| 4,225,439 A | 9/1980 | Spranger | |
| 4,228,032 A | 10/1980 | Talcott | |
| 4,253,458 A | 3/1981 | Bacehowski et al. | |
| 4,256,692 A | 3/1981 | Cover | |
| 4,262,581 A | 4/1981 | Ferrell | |
| 4,300,559 A | 11/1981 | Gajewski et al. | |
| 4,314,480 A | 2/1982 | Becker | |
| 4,342,723 A * | 8/1982 | Sado | A61M 1/1698 |
| | | | 210/321.75 |
| 4,366,179 A | 12/1982 | Nawata et al. | |
| 4,370,160 A | 1/1983 | Ziemelis | |
| 4,381,775 A | 5/1983 | Nose' et al. | |
| 4,386,069 A | 5/1983 | Estep | |
| 4,398,642 A | 8/1983 | Okudaira et al. | |
| 4,440,815 A | 4/1984 | Zomorodi et al. | |
| 4,455,299 A | 6/1984 | Grode | |
| 4,540,416 A | 9/1985 | Hattori et al. | |
| 4,568,328 A | 2/1986 | King | |
| 4,572,899 A | 2/1986 | Walker et al. | |
| 4,579,223 A | 4/1986 | Otsuka et al. | |
| 4,585,735 A | 4/1986 | Meryman et al. | |
| 4,629,544 A | 12/1986 | Bonaventura et al. | |
| 4,639,353 A * | 1/1987 | Takemura | A61M 1/1698 |
| | | | 128/DIG. 3 |
| 4,654,053 A | 3/1987 | Sievers et al. | |
| 4,659,549 A * | 4/1987 | Hamada | A61M 1/1698 |
| | | | 128/DIG. 3 |
| 4,670,013 A | 6/1987 | Barnes et al. | |
| 4,701,267 A | 10/1987 | Watanabe et al. | |
| 4,713,176 A | 12/1987 | Schoendorfer et al. | |
| 4,731,978 A | 5/1988 | Martensson | |
| 4,748,121 A | 5/1988 | Beaver et al. | |
| 4,749,551 A | 6/1988 | Borgione | |
| 4,769,175 A | 9/1988 | Inoue | |
| 4,769,318 A | 9/1988 | Hamasaki et al. | |
| 4,798,728 A | 1/1989 | Sugisawa | |
| 4,837,047 A | 6/1989 | Sato et al. | |
| 4,859,360 A | 8/1989 | Suzuki et al. | |
| 4,861,867 A | 8/1989 | Estep | |
| 4,880,548 A | 11/1989 | Pall et al. | |
| 4,880,786 A | 11/1989 | Sasakawa et al. | |
| 4,902,701 A | 2/1990 | Batchelor et al. | |
| 4,925,572 A | 5/1990 | Pall | |
| 4,986,837 A | 1/1991 | Shibata | |
| 4,998,990 A | 3/1991 | Richter et al. | |
| 5,000,848 A | 3/1991 | Hodgins et al. | |
| 5,023,054 A | 6/1991 | Sato et al. | |
| 5,037,419 A | 8/1991 | Valentine et al. | |
| 5,120,659 A | 6/1992 | King et al. | |
| 5,137,531 A * | 8/1992 | Lee | A61M 1/1698 |
| | | | 128/DIG. 3 |
| 5,139,668 A | 8/1992 | Pan et al. | |
| 5,143,763 A | 9/1992 | Yamada et al. | |
| 5,152,905 A | 10/1992 | Pall et al. | |
| 5,192,320 A | 3/1993 | Anazawa et al. | |
| 5,194,158 A | 3/1993 | Matson | |
| 5,208,335 A | 5/1993 | Ramprasad et al. | |
| 5,229,012 A | 7/1993 | Pall et al. | |
| 5,254,248 A | 10/1993 | Nakamura et al. | |
| 5,286,407 A | 2/1994 | Inoue et al. | |
| 5,328,268 A | 7/1994 | LaFleur | |
| 5,353,793 A | 10/1994 | Bornn | |
| 5,356,375 A | 10/1994 | Higley | |
| 5,360,734 A | 11/1994 | Chapman et al. | |
| 5,362,442 A | 11/1994 | Kent | |
| 5,368,808 A | 11/1994 | Koike et al. | |
| 5,382,526 A | 1/1995 | Gajewski et al. | |
| 5,386,014 A | 1/1995 | Nho et al. | |
| 5,387,624 A | 2/1995 | Morita et al. | |
| 5,417,986 A | 5/1995 | Reid et al. | |
| 5,427,663 A | 6/1995 | Austin et al. | |
| 5,443,743 A | 8/1995 | Gsell | |
| 5,449,617 A | 9/1995 | Falkenberg et al. | |
| 5,476,764 A | 12/1995 | Bitensky | |
| 5,506,141 A | 4/1996 | Weinreb et al. | |
| 5,529,821 A | 6/1996 | Ishikawa et al. | |
| 5,605,934 A | 2/1997 | Giertych | |
| 5,617,873 A | 4/1997 | Yost et al. | |
| 5,624,794 A | 4/1997 | Bitensky et al. | |
| 5,635,358 A | 6/1997 | Wilding et al. | |
| 5,686,304 A | 11/1997 | Codner | |
| 5,691,452 A | 11/1997 | Gawryl et al. | |
| 5,693,122 A | 12/1997 | Berndt | |
| 5,693,230 A | 12/1997 | Asher | |
| 5,698,250 A | 12/1997 | DelDuca et al. | |
| 5,709,472 A | 1/1998 | Prusik et al. | |
| 5,744,056 A | 4/1998 | Venkateshwaran et al. | |
| 5,730,989 A | 5/1998 | Wright | |
| 5,750,115 A | 5/1998 | Van Den Bosch | |
| 5,783,094 A | 7/1998 | Kraus et al. | |
| 5,783,148 A | 7/1998 | Cottingham et al. | |
| 5,789,151 A | 8/1998 | Bitensky et al. | |
| 5,789,152 A | 8/1998 | Black et al. | |
| 5,811,142 A | 9/1998 | DelDuca et al. | |
| 5,846,427 A | 12/1998 | Kessler et al. | |
| 5,858,015 A | 1/1999 | Fini | |
| 5,858,643 A | 1/1999 | Ben-Hur et al. | |
| 5,863,460 A | 1/1999 | Slovacek et al. | |
| 5,895,810 A | 4/1999 | Light et al. | |
| 5,902,747 A | 5/1999 | Nemser et al. | |
| 5,906,285 A | 5/1999 | Slat | |
| 5,955,519 A | 9/1999 | Neri | |
| 5,962,650 A | 10/1999 | Osterberg et al. | |
| 5,972,710 A | 10/1999 | Weigl et al. | |
| 6,007,529 A | 12/1999 | Gustafsson et al. | |
| 6,027,623 A | 2/2000 | Ohkawa | |
| 6,042,264 A | 3/2000 | Prusik et al. | |
| 6,045,701 A | 4/2000 | Ung-Chhun et al. | |
| 6,047,203 A | 4/2000 | Sackner et al. | |
| 6,076,664 A | 6/2000 | Yeager | |
| 6,080,322 A | 6/2000 | Deniega et al. | |
| 6,090,062 A | 7/2000 | Sood et al. | |
| 6,097,293 A | 8/2000 | Galloway et al. | |
| 6,148,536 A | 11/2000 | Iijima | |
| 6,150,085 A | 11/2000 | Hess et al. | |
| 6,156,231 A | 12/2000 | McKedy | |
| 6,162,396 A | 12/2000 | Bitensky et al. | |
| 6,164,821 A | 12/2000 | Randall | |
| 6,187,572 B1 | 2/2001 | Platz et al. | |
| 6,210,601 B1 | 4/2001 | Hottle et al. | |
| 6,231,770 B1 | 5/2001 | Bormann et al. | |
| 6,248,690 B1 | 6/2001 | McKedy | |
| 6,254,628 B1 | 7/2001 | Wallace et al. | |
| 6,287,284 B1 | 9/2001 | Warburton-Pitt | |
| 6,315,815 B1 | 11/2001 | Spadaccini et al. | |
| 6,337,026 B1 | 1/2002 | Lee et al. | |
| 6,358,678 B1 | 3/2002 | Bakaltcheva et al. | |
| 6,368,871 B1 | 4/2002 | Christel et al. | |
| 6,387,461 B1 | 5/2002 | Ebner et al. | |
| 6,402,818 B1 | 6/2002 | Sengupta | |
| 6,403,124 B1 | 6/2002 | Dottori | |
| 6,413,713 B1 | 7/2002 | Serebrennikov | |
| 6,436,872 B2 | 8/2002 | McKedy | |
| 6,439,577 B2 | 8/2002 | Jorgensen et al. | |
| 6,447,987 B1 | 9/2002 | Hess et al. | |
| 6,468,732 B1 | 10/2002 | Malin et al. | |
| 6,475,147 B1 | 11/2002 | Yost et al. | |
| 6,482,585 B2 | 11/2002 | Dottori | |
| 6,494,909 B2 | 12/2002 | Greenhalgh | |
| 6,527,957 B1 | 3/2003 | Denienga et al. | |
| 6,558,571 B1 | 5/2003 | Powers | |
| 6,564,207 B1 | 5/2003 | Abdoh | |

(56) References Cited

U.S. PATENT DOCUMENTS

| | | |
|---|---|---|
| 6,582,496 B1 | 6/2003 | Cheng et al. |
| 6,610,772 B1 | 8/2003 | Clauberg et al. |
| 6,626,884 B1 | 9/2003 | Dillon et al. |
| 6,688,476 B2 | 2/2004 | Breillatt, Jr. et al. |
| 6,695,803 B1 | 2/2004 | Robinson et al. |
| 6,697,667 B1 | 2/2004 | Lee et al. |
| 6,709,492 B1 | 3/2004 | Spadaccini et al. |
| 6,723,051 B2 | 4/2004 | Davidson et al. |
| 6,761,695 B2 | 7/2004 | Yost et al. |
| 6,773,407 B2 | 8/2004 | Yost et al. |
| 6,808,675 B1 | 10/2004 | Coelho et al. |
| 6,817,979 B2 | 11/2004 | Nihtilä |
| 6,866,783 B2 | 3/2005 | Baurmeister et al. |
| 6,878,335 B2 | 4/2005 | Britten et al. |
| 6,899,822 B2 | 5/2005 | McKedy |
| 6,955,648 B2 | 10/2005 | Mozayeni et al. |
| 6,977,105 B2 | 12/2005 | Fujieda et al. |
| 7,041,800 B1 | 5/2006 | Gawryl et al. |
| 7,097,690 B2 | 8/2006 | Usher et al. |
| 7,104,958 B2 | 9/2006 | Crutchfield et al. |
| 7,125,498 B2 | 10/2006 | McKedy |
| 7,208,120 B2 | 4/2007 | Bitensky et al. |
| 7,347,887 B2 | 3/2008 | Bulow et al. |
| 7,361,277 B2 | 4/2008 | Bormann et al. |
| 7,431,995 B2 | 10/2008 | Smith et al. |
| 7,452,601 B2 | 11/2008 | Ebner et al. |
| 7,517,146 B2 | 4/2009 | Smith et al. |
| 7,666,486 B2 | 2/2010 | Sato et al. |
| 7,713,614 B2 | 5/2010 | Chow et al. |
| 7,721,898 B2 | 5/2010 | Yagi et al. |
| 7,723,017 B2 | 5/2010 | Bitensky et al. |
| 7,754,798 B2 | 7/2010 | Ebner et al. |
| 7,763,097 B2 | 7/2010 | Federspiel |
| 7,775,376 B2 | 8/2010 | Bonaguidi et al. |
| 7,784,619 B2 | 8/2010 | Jacobson |
| 8,070,664 B2 | 12/2011 | Rochat |
| 8,071,282 B2 | 12/2011 | Bitensky et al. |
| 8,535,421 B2 | 9/2013 | Yoshida et al. |
| 8,569,052 B2 | 10/2013 | Federspiel et al. |
| 8,864,735 B2 | 10/2014 | Sano et al. |
| 8,887,721 B2 | 11/2014 | Zapol et al. |
| 9,005,343 B2 | 4/2015 | Yoshida et al. |
| 9,067,004 B2 | 6/2015 | Yoshida et al. |
| 9,199,016 B2 | 12/2015 | Yoshida et al. |
| 9,296,990 B2 | 3/2016 | Federspiel et al. |
| 9,539,375 B2 | 1/2017 | Yoshida et al. |
| 9,801,784 B2 | 10/2017 | Yoshida et al. |
| 9,844,615 B2 | 12/2017 | Yoshida et al. |
| 2001/0027156 A1 | 10/2001 | Egozy et al. |
| 2001/0037078 A1 | 11/2001 | Lynn et al. |
| 2001/0049089 A1 | 12/2001 | Dottori |
| 2002/0062078 A1 | 5/2002 | Crutchfield et al. |
| 2002/0066699 A1 | 6/2002 | Boggs et al. |
| 2002/0085952 A1 | 7/2002 | Ellingboe et al. |
| 2002/0086329 A1 | 7/2002 | Shvets et al. |
| 2002/0099570 A1 | 7/2002 | Knight |
| 2002/0176798 A1 | 11/2002 | Linker et al. |
| 2002/0182241 A1 | 12/2002 | Borenstein et al. |
| 2003/0003575 A1 | 1/2003 | Vacanti et al. |
| 2003/0039582 A1 | 2/2003 | Chambers et al. |
| 2003/0040835 A1* | 2/2003 | Ng .................. A61M 1/387 700/214 |
| 2003/0062299 A1 | 4/2003 | Lee et al. |
| 2003/0106861 A1 | 6/2003 | Gibbs et al. |
| 2003/0124504 A1 | 7/2003 | Bitensky et al. |
| 2003/0153074 A1 | 8/2003 | Bitensky et al. |
| 2003/0183801 A1 | 10/2003 | Yang et al. |
| 2003/0189003 A1 | 10/2003 | Kraus et al. |
| 2003/0190272 A1 | 10/2003 | Raine et al. |
| 2003/0201160 A1 | 10/2003 | Goodrich et al. |
| 2003/0215784 A1 | 11/2003 | Dumont et al. |
| 2003/0233934 A1 | 12/2003 | Wijmans et al. |
| 2004/0013566 A1 | 1/2004 | Myrick et al. |
| 2004/0026341 A1 | 2/2004 | Hogberg et al. |
| 2004/0097862 A1 | 5/2004 | Lampeter et al. |
| 2004/0126880 A1 | 7/2004 | Manders et al. |
| 2004/0168982 A1* | 9/2004 | Bitensky .......... B01L 3/5027 210/649 |
| 2004/0254560 A1 | 12/2004 | Coelho et al. |
| 2005/0038342 A1 | 2/2005 | Mozayeni et al. |
| 2005/0085785 A1 | 4/2005 | Shang et al. |
| 2005/0137517 A1 | 6/2005 | Blickhan et al. |
| 2005/0139806 A1 | 6/2005 | Havens et al. |
| 2005/0208462 A1 | 9/2005 | Bitensky et al. |
| 2005/0210141 A1 | 9/2005 | Oyama et al. |
| 2005/0230856 A1 | 10/2005 | Parekh et al. |
| 2005/0233302 A1 | 10/2005 | Hess et al. |
| 2006/0081524 A1 | 4/2006 | Sengupta et al. |
| 2006/0118479 A1 | 6/2006 | Shevkoplyas et al. |
| 2006/0160724 A1 | 7/2006 | Gawryl et al. |
| 2006/0169138 A1 | 8/2006 | Schmidt |
| 2006/0226087 A1 | 10/2006 | Robinson et al. |
| 2006/0278073 A1 | 12/2006 | McHugh |
| 2007/0078113 A1 | 4/2007 | Roth et al. |
| 2007/0099170 A1 | 5/2007 | Goodrich et al. |
| 2007/0240569 A1 | 10/2007 | Ooya |
| 2007/0276508 A1* | 11/2007 | Fischer .......... A61M 1/1698 623/23.65 |
| 2008/0027368 A1 | 1/2008 | Kollar et al. |
| 2008/0098894 A1 | 5/2008 | Sabatino et al. |
| 2008/0160107 A1 | 7/2008 | McCaney et al. |
| 2008/0234327 A1 | 9/2008 | Cadieux et al. |
| 2008/0243045 A1 | 10/2008 | Pasqualini |
| 2008/0276803 A1 | 11/2008 | Molaison et al. |
| 2009/0017128 A1 | 1/2009 | Monzyk et al. |
| 2009/0084720 A1 | 4/2009 | Dannenmaier et al. |
| 2009/0235619 A1 | 9/2009 | Ostler et al. |
| 2009/0269837 A1 | 10/2009 | Shevkoplyas et al. |
| 2010/0021879 A1 | 1/2010 | Delgado et al. |
| 2010/0133203 A1 | 6/2010 | Walker et al. |
| 2010/0221697 A1 | 9/2010 | Sehgal |
| 2010/0282662 A1 | 11/2010 | Lee et al. |
| 2010/0294128 A1 | 11/2010 | Schmidt et al. |
| 2010/0313755 A1 | 12/2010 | Koros et al. |
| 2010/0331767 A1 | 12/2010 | Frankowski |
| 2011/0092875 A1 | 4/2011 | Beck |
| 2012/0024156 A1 | 2/2012 | Yoshida et al. |
| 2012/0077182 A1 | 3/2012 | Bitensky et al. |
| 2012/0100523 A1 | 4/2012 | Federspiel et al. |
| 2012/0115124 A1 | 5/2012 | Yoshida et al. |
| 2012/0129148 A1 | 5/2012 | Hess et al. |
| 2012/0129149 A1 | 5/2012 | Federspiel et al. |
| 2012/0146266 A1 | 6/2012 | Oda et al. |
| 2012/0219633 A1 | 8/2012 | Sowemimo-Coker |
| 2013/0004937 A1 | 1/2013 | Yoshida et al. |
| 2013/0144266 A1* | 6/2013 | Borenstein .......... A61M 1/1698 604/522 |
| 2013/0197420 A1 | 8/2013 | Fissell, IV et al. |
| 2013/0259744 A1 | 10/2013 | Yoshida et al. |
| 2013/0327677 A1 | 12/2013 | McDorman |
| 2014/0012185 A1 | 1/2014 | Ishizuka et al. |
| 2014/0134503 A1 | 5/2014 | Lockett et al. |
| 2014/0146266 A1 | 5/2014 | Zhang |
| 2014/0158604 A1 | 6/2014 | Chammas et al. |
| 2014/0248005 A1 | 9/2014 | David et al. |
| 2015/0306288 A1 | 10/2015 | Delorme et al. |
| 2016/0007588 A1 | 1/2016 | Levesque et al. |
| 2016/0242410 A9 | 8/2016 | Yoshida et al. |

FOREIGN PATENT DOCUMENTS

| | | |
|---|---|---|
| CN | 2502700 Y | 7/2002 |
| CN | 1642628 A | 7/2005 |
| CN | 2780207 Y | 5/2006 |
| CN | 2894710 Y | 5/2007 |
| CN | 101039737 A | 9/2007 |
| DE | 3722984 | 1/1989 |
| DE | 10327988 A1 | 7/2004 |
| EP | 0 100 419 A2 | 2/1984 |
| EP | 0 217 759 A1 | 4/1987 |
| EP | 0 299 381 A2 | 1/1989 |
| EP | 0 890 368 A1 | 1/1999 |
| EP | 1109447 | 10/2003 |
| EP | 1 891 999 A1 | 2/2008 |

(56) References Cited

FOREIGN PATENT DOCUMENTS

| | | |
|---|---|---|
| EP | 2635114 | 9/2013 |
| EP | 3 285 711 A1 | 10/2016 |
| EP | 3 268 015 A1 | 1/2018 |
| FR | 2 581 289 A1 | 11/1986 |
| FR | 2 996 413 A1 | 4/2014 |
| GB | 1 044 649 A2 | 10/1966 |
| GB | 2283015 A1 | 4/1995 |
| JP | 58-194879 | 11/1983 |
| JP | 59-115349 | 7/1984 |
| JP | 61-109577 A | 5/1986 |
| JP | 63-63616 A | 3/1988 |
| JP | 01-104271 A | 4/1989 |
| JP | 3-284263 | 12/1991 |
| JP | 5-503075 A | 5/1993 |
| JP | 5-503304 A | 6/1993 |
| JP | H 05-148151 A | 6/1993 |
| JP | 05-305123 A | 11/1993 |
| JP | H 05-317413 | 12/1993 |
| JP | 06-121920 A | 5/1994 |
| JP | 2668446 | 7/1997 |
| JP | 2700170 B2 | 1/1998 |
| JP | 10-501443 A | 2/1998 |
| JP | 11-216179 | 8/1999 |
| JP | 2000-516963 A | 12/2000 |
| JP | 2002-087971 | 3/2002 |
| JP | 2002-253936 A | 9/2002 |
| JP | 2002-541941 | 12/2002 |
| JP | 2004-089495 A | 3/2004 |
| JP | 2005-533041 A | 11/2005 |
| JP | 2005-535279 A | 11/2005 |
| JP | 2005-535289 A | 11/2005 |
| JP | 2006-502078 A | 1/2006 |
| JP | 2006-515279 | 5/2006 |
| JP | 2006-213923 | 8/2006 |
| JP | 2007-260393 A | 10/2007 |
| JP | 2008-86996 | 4/2008 |
| JP | 2008-528066 | 7/2008 |
| JP | 2008-529550 A | 8/2008 |
| JP | 2008-253452 | 10/2008 |
| JP | 2009-513235 | 4/2009 |
| JP | 10/501443 | 2/2010 |
| JP | 2010-503501 A | 2/2010 |
| JP | 2010-509353 | 3/2010 |
| JP | 2010-116626 | 5/2010 |
| JP | 2010-538735 | 12/2010 |
| JP | 2011-92905 | 5/2011 |
| JP | 2013-500794 | 1/2013 |
| JP | 2014-518283 | 7/2014 |
| JP | 2014-527436 | 10/2014 |
| JP | 2007-509206 A | 4/2017 |
| KR | 10-0721054 | 5/2006 |
| SU | 1718766 A1 | 1/1990 |
| WO | WO 1981/02239 A1 | 8/1981 |
| WO | WO 1986/00809 A1 | 2/1986 |
| WO | WO 1989/02274 A1 | 3/1989 |
| WO | WO 1991/04659 A1 | 4/1991 |
| WO | WO 1992/08348 A1 | 5/1992 |
| WO | WO 1995/29662 A2 | 11/1995 |
| WO | WO 1996/29103 A1 | 9/1996 |
| WO | WO 1996/29346 A1 | 9/1996 |
| WO | WO 1996/29864 A1 | 10/1996 |
| WO | WO 1996/39026 A1 | 12/1996 |
| WO | WO 1997/37628 A1 | 10/1997 |
| WO | WO 1998/046073 A1 | 10/1998 |
| WO | WO 1998/51147 A1 | 11/1998 |
| WO | WO 1999/25726 A1 | 5/1999 |
| WO | WO 1999/29346 A1 | 6/1999 |
| WO | WO 1999/48963 A2 | 9/1999 |
| WO | WO 2000/011946 A2 | 3/2000 |
| WO | WO 2000/0062891 | 10/2000 |
| WO | WO 2003/043419 A1 | 5/2003 |
| WO | WO 2003/043571 A2 | 5/2003 |
| WO | WO 2003/086577 A1 | 10/2003 |
| WO | WO 03/103390 A1 | 12/2003 |
| WO | WO 2004/043381 A2 | 5/2004 |
| WO | WO 2006-057473 A1 | 6/2006 |
| WO | WO 2006/088455 A1 | 8/2006 |
| WO | WO 2008/063868 | 5/2008 |
| WO | WO 2009/132839 A1 | 11/2009 |
| WO | WO 2011/014855 A2 | 2/2011 |
| WO | WO 2011/046841 A1 | 4/2011 |
| WO | WO 2011/046963 A1 | 4/2011 |
| WO | WO 2011/068897 A1 | 6/2011 |
| WO | WO 2012/027582 A1 | 3/2012 |
| WO | WO 2012/061731 A1 | 5/2012 |
| WO | WO 2012/120927 A1 | 9/2012 |
| WO | WO 2013/006631 A1 | 1/2013 |
| WO | WO 2013/022491 A1 | 2/2013 |
| WO | WO 2013/023156 A1 | 2/2013 |
| WO | WO 2013/043658 A1 | 3/2013 |
| WO | WO 2013/153441 A1 | 10/2013 |
| WO | WO 2013/177339 A1 | 11/2013 |
| WO | WO 2014/134503 A1 | 9/2014 |
| WO | WO 2014/194931 A1 | 12/2014 |
| WO | WO 2016/145210 A1 | 9/2016 |
| WO | WO 2016/172645 A1 | 10/2016 |

OTHER PUBLICATIONS

Gardner, "Problems of Multiple Transfusions," *Official Journal of the California Medical Associate*, 83(2):93-97 (1958).
Peirce et al., "The Membrane Lung: Studies with a New High Permeability Co-Polymer Membrane," Trans. Amer. Soc. Artif. Int. Organs vol. XIV:220-226 (1968).
Steurer et al., "Trauma and Massive Blood Transfusions," Curr. Anesthesiol. Rep 4:200-208 (2014).
International Search Report for PCT/US2016/051115 dated Nov. 21, 2016.
International Search Report for PCT/US2017/034410 dated Dec. 22, 2017.
U.S. Appl. No. 10/295,781, filed Nov. 15, 2002, Bitensky et al.
U.S. Appl. No. 12/901,350, filed Oct. 8, 2010, Yoshida et al.
U.S. Appl. No. 62/131,130, filed Mar. 15, 2015, Wolf et al.
U.S. Appl. No. 62/151,957, filed Apr. 23, 2015, Yoshida et al.
Alcantar et al., "Polyethylene glycol-coated biocompatible surfaces," *Journal of Biomedical Materials Research*, 51(3):343-351 (2000).
Anderson et al., "Microfabrication and microfluidics for tissue engineering: state of the art and future opportunities," *Lab Chip*, 4:98-103 (2004).
Barbee et al., "The Fahraeus Effect," *Microvascular Research*, 3:6-16 (1971).
Barclay et al., "A Method for Detecting Chaos in Canine Myocardial Microcirculatory Red Cell Flux," *Microcirculation*, 7(5):335-346 (2000).
Bardy et al., "Technetium-99m Labeling by Means of Stannous Pyrophosphate: Application to Bleomycin and Red Blood Cells," *Journal of Nuclear Medicine*, 16(5):435-437 (1975).
Barras et al., "Einfluss der Rejuvenation auf die rheologischen Eigenschaften gelagerter Erythrozyten," *VASA*, 23(4):305-311 (1994).
Buskirk et al., "Accumulation of Biologic response modifiers during red blood cell cold storage," *Transfusion*, 49(Suppl3): 102A-103A (2009).
Benson et al., "Accumulation of Pro-Cancer Cytokines in the Plasma Fraction of Stored Packed Red Cells," *J Gastrointest Surg.*, 16:460-468 (2012).
Bensinger et al., "Prolonged maintenance of 2,3-DPG in liquid blood storage: Use of an internal $CO_2$ trap to stabilize pH," *J. Lab. Clin. Med.*, 89(3):498-503 (1977).
Beutler et al., "Storage of red cell concentrates in CPD-A2 for 42 and 49 days," *The Journal of Laboratory and Clinical Medicine*, 102(1):53-62 (1983).
Borenstein et al., "Microfabrication Technology for Vascularized Tissue Engineering," *Biomedical Microdevices*, 4(3):167-175 (2002).
Brody et al., "Deformation and Flow of Red Blood Cells in a Synthetic Lattice: Evidence for an Active Cytoskeleton," *Biophysical Journal*, 68:2224-2232 (1995).

(56) References Cited

OTHER PUBLICATIONS

Burns et al., "Artificial microvascular network: a new tool for measuring rheologic properties of stored red blood cells," *Transfusion*, 52(5):1010-1023 (2012).
Carr et al., "Nonlinear Dynamics of Microvascular Blood Flow," *Annals of Biomedical Engineering*, 28:641-652 (2000).
Carmen, "The Selection of Plastic Materials for Blood Bags," *Transfusion Medicine Reviews*, 7(1):1-10 (1993).
Cell Deformability, RheoSCAN (Rheo Scan-AnD300/RheoScan-D300), obtained on Dec. 11, 2012, from: http://www.rheoscan.com/products/products/products-01.html.
Chaplin et al., "The Proper Use of Previously Frozen Blood Cells for Transfusion," *Blood*, 59:1118-1120 (1982).
Chilton et al., "Privacy Protection of Health Information: Patient Rights and Pediatrician Responsibilities," *Pediatrics*, 104(4):973-977 (1999).
Cognasse et al., "The role of microparticles in inflammation and transfusion: A concise review," *Transfus. Apher. Sci.* 53(2):159-167 (2015).
Cokelet et al., "Fabrication of in Vitro Microvascular Blood Flow Systems by Photolithography," *Microvascular Research*, 46:394-400 (1993).
Dale et al., "Human Vaccination with *Escherichia coli* J5 Mutant Induces Cross-Reactive Bactericidal Antibody against *Neisseria gonorrhoeae* Lipooligosaccharide," *The Journal of Infectious Diseases*, 166:316-325 (1992).
De Angelis et al., "Erythrocyte Shape Control in Stored Blood: The Effect of Additive Solutions on Shape Recovery," *Haematologica*, 73:7-12 (1988).
Deible et al., "Molecular barriers to biomaterial thrombosis by modification of surface proteins with polyethylene glycol," *Biomaterials*, 19:1885-1893 (1998).
De Korte et al., "Prolonged maintenance of 2,3-diphosphoglycerate acid and adenosine triphosphate in red blood cells during storage," *Transfusion*, 48:1081-1089 (2008).
De Venuto et al., "Rejuvenation of Human Red Blood Cells During Liquid Storage," *Transfusion*, 14(4):338-344 (1974).
Dumaswala et al., "Studies in Red Blood Cell Preservation: 9. The Role of Glutamine in Red Cell Preservation," *Vox Sang*, 67:255-259 (1994).
Dumaswala et al., "Glutamine- and Phosphate-Containing Hypotonic Storage Media Better Maintain Erythrocyte Membrane Physical Properties," *Blood*, 88(2):697-704 (1996).
Dumaswala et al., "Improved Red Blood Cell Preservation Correlates With Decreased Loss of Bands 3, 4.1, Aeetyleholinestrase, and Lipids in Microvesicles," *Blood*, 87(4): 1612-1616 (1996).
Dumont et al., "Anaerobic storage of red blood cells in a novel additive solution improves in vivo recovery," *Transfusion*, 49(3):458-464 (2009).
Dumont et al., "$CO_2$-dependent metabolic modulation in red cells stored under anaerobic conditions," *Transfusio* 56(2): 392-403 (epub 2015).
Durapore® Membrane Filters—Filter Discs and Membranes, retrieved on Aug. 26, 2014, from: www.emdmillipore.com/US/en/product/Durapore.
Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).
European Search Report completed on Feb. 11, 2005, in European Patent Application No. 02 78 2307.9.
Extended European Search Report, dated Aug. 29, 2014 for European Patent Application No. 10823965.8.
Extended European Search Report dated Oct. 30, 2014 in European Patent Application No. 11838889.1.
Extended European Search Report dated Nov. 3, 2014 in European Patent Application No. 12807324.4.
Extended European Search Report dated Mar. 5, 2015, in European Patent Application No. 12821624.9.
Extended European Search Report dated Jun. 15, 2015, in European Patent Application No. 11820660.6.
Fage et al., "On transition from laminar to turbulent flow in the boundary layer," The gamma-ray transition of radio-bromine, *Proceedings of the Royal Society*, 178(973):205-227 (1940).
Fahraeus et al., "The Viscosity of the Blood in Narrow Capillary Tubes," *Am. J. Physiol.*, 96(3):562-568 (1931).
Fang et al., "Inhibition of Lipopolysaccharide-Associated Endotoxin Activities in Vitro and in Vivo by the Human Anti-Lipid A Monoclonal Antibody SdJ5-1.17.15," *Infection and Immunity*, 61(9):3873-3878 (1993).
Fatouros et al., "Recombinant factor VII SQ—influence of oxygen, metal ions, pH and ionic strength on its stability in aqueous solution," *International Journal of Pharmaceuticals*, 155(1):121-131 (1997).
Frame et al., "A System for Culture of Endothelial Cells in 20-50-µm Branching Tubes," *Microcirculation*, 2(4):377-385 (1995).
"Friction Factor for Flow in Coils and Curved Pipe," *Neutrium* Available on the world wide web at neutrium.net/fluid_flow/friction-factor-for-flow-in-coils-and-curved-pipe/. (2017).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).
Gifford et al., "Parallel Microchannel-Based Measurements of Individual Erythrocyte Areas and Volumes," Biophysical Journal, 84:623-633 (2003).
Gifford et al., "A detailed study of time-dependent changes in human red blood cells: from reticulocyte maturation to erythrocyte senescence," British Journal of Haematology, 135:395-404 (2006).
Green et al., "10. Liposomal Vaccines," Immunobiology of Proteins and Peptides VII, Plenum Press, New York, pp. 83-92 (1995).
Greenwalt et al., "Studies in Red Blood Cell Preservation. 7. In vivo and in Vitro Studies with a Modified Phosphate-Ammonium Additive Solution," *Vox Sang*, 65:87-94 (1993).
Greenwalt et al., "Studies in Red Blood Cell Preservation. 8. Liquid Storage of Red Cells in Glycerol-Containing Additive Solution," *Vox. Sang*, 67:139-143 (1994).
Greenwalt et al., "Studies in red blood cell preservation. 10. $^{51}$Cr Recovery of Red Cells after Liquid Storage in a Glycerol-Containing Additive Solution," *Vox Sang*, 70:6-10 (1996).
Greenwalt et al., "The effect of hypotonicity, glutamine, and glycine on red cell preservation," *Transfusion*, 37:269-276 (1997).
Griffith, "Temporal chaos in the microcirculation," *Cardiovascular Research*, 31:342-358 (1996).
Grigioni et al., "A discussion on the threshold limited for nemo lysis related to Reynolds shear stress," *J. Biomech.*, 32:1107-1112 (1999).
Gulliksson et al., "Storage of whole blood overnight in different blood bags preceding preparation of blood components: in vitro effects on red blood cells," *Blood Transfus* 7:210-215 (2009).
Hamasaki et al., "Acid-citrate-dextrose-phosphoenolpyruvate medium as rejuvenant for blood storage," *Transfusion*, 23(1):1-7 (1983).
Heaton et al., "Use of Adsol preservation solution for prolonged storage of low viscosity AS-1 red blood cells," *Br J. Haematol*, 57(3):467-478 (1984).
Hess, "Extended Liquid Storage of Red Blood Cells," Blood Donors and the Supply of Blood and Blood Products, National Academy Press, Washington, D.C., pp. 99-102 (1996).
Hess et al., "Successful storage of RBCs for 9 weeks in a new additive solution," *Transfusion*, 40:1007-1011 (2000).
Hess, "Storage of red blood cells under anaerobic conditions," *Vox Sanguinis*, 93:183 (2007).
Hess et al., "Alkaline CPD and the preservation of RBC 2,3-DPG," *Transfusion*, 42:747-752 (2002).
Hess et al., "Storage of Red Blood Cells: New Approaches," *Transfusion Medicine Reviews*, 16(4):283-295 (2002).
Hodgson et al., "Prophylactic use of human endotoxin-core hyperimmune gammaglobulin to prevent endotoxaemia in colostrum-deprived, gnotobiotic lambs challenged orally with *Escherichia coli,*" *FEMS Immunology and Medical Microbiology*, 11:171-180 (1995).

(56) References Cited

OTHER PUBLICATIONS

Högman et al., "Cell Shape and Total Adenylate Concentration as Important Factors for Posttransfusion Survival of Erythrocytes," *Biomed. Biochim. Acta*, 42:S327-S331 (1983).
Högman et al., "Effects of Oxygen on Red Cells during Liquid Storage at +4° C," *Vox Sang.*, 51:27-34 (1986).
Högman et al., "Effects of Oxygen and Mixing on red cells stored in plastic bags at +4° C," *Biomed. Biochim. Acta.*, 46:S290-S294 (1987).
Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).
Högman, "Preparation and Preservation of Red Cells," *Vox Sanguinis* 74(Suppl. 2):177-187 (1998).
Holme et al., "Current Issues Related to the Quality of Stored RBCs," *Transfusion and Apheresis Science*, 33(1):55-61 (2005).
Huang et al., "Continuous Particle Separation Through Deterministic Lateral Displacement," *Science*, 304:987-990 (2004).
International Committee for Standardization in Hematology, "Recommended Methods for Radioisotope Red Cell Survival Studies," *Blood* 38(3):378-386 (1971).
International Preliminary Report on Patentability dated Apr. 9, 2012 (completed on Feb. 14, 2012), in International Patent Application No. PCT/US2010/52084.
International Search Report and Written Opinion dated Dec. 6, 2010 for corresponding International Patent Application No. PCT/US2010/052376.
International Preliminary Report on Patentability dated May 24, 2012 (completed on May 21, 2012), in International Patent Application No. PCT/US2010/52376.
International Preliminary Report on Patentability completed on Oct. 18, 2011, in International Patent Application No. PCT/US2010/031055.
International Search Report completed on Jul. 8, 1996, in International Patent Application No. PCT/US96/09005.
International Search Report completed on Nov. 10, 2003, in International Patent Application No. PCT/US02/36735.
International Search Report completed on May 20, 2010, in International Patent Application No. PCT/US2010/31055.
International Search Report dated Apr. 27, 2011(completed on Apr. 26, 2011), in International Patent Application No. PCT/US2010/044045.
International Search Report completed on Dec. 21, 2011, in International Patent Application No. PCT/US11/49168.
International Search Report completed on Feb. 12, 2012, in International Patent Application No. PCT/US11/59372.
International Search Report completed on Jun. 18, 2012, in International Patent Application No. PCT/US12/30930.
International Search Report completed on Sep. 24, 2012, in International Patent Application No. PCT/US12/50380.
International Search Report and Written Opinion issued in International Application PCT/US2014/019537 dated Jul. 10, 2014.
International Search Report completed on Nov. 9, 2012 issued in International Patent Application No. PCT/US12/045426 (dated Nov. 26, 2012).
International Search Report for PCT/US2016/021794 dated Jul. 18, 2016.
Irsch et al., "Pathogen inactivation of platelet and plasma blood components for transfusion using the INTERCEPT Blood System™," *Transfusion Medicine and Hemotherapy*, 38:19-31 (2011).
Jain, et al., "Determinants of Leukocyte Margination in Rectangular Microchannels," *PLoS One*, 4(9):1-8 (2009).
Jarus et al., "Barrier Properties of polypropylene/polyamide blends produced by microlayer coextrusion," *Polymer* 43:2401-2408 (2012).
Jayasinghe et al., "Controlled deposition of nanoparticle clusters by electrohydrodynamic atomization," *Nanotechnology*, 15:1519-1523 (2004).
Jiang et al., "Microfluidic synthesis of monodisperse PDMS microbeads as discrete oxygen sensors," *Soft Matter*, 8:923-926 (2011).

Jo et al., "Surface modification using silanated poly(ethylene glycol)s," *Biomaterials*, 21:605-616 (2000).
Johnson et al., "Regulation of blood flow in single capillaries," *American Journal of Physiology*, 212:1405-1415 (1967).
Kaihara et al., "Silicon Micromachining to Tissue Engineer Branched Vascular Channels for Liver Fabrication," *Tissue Engineering*, 6(2):105-117 (2000).
Kaiser-Guignard et al., "The clinical and biological impact of new pathogen inactivation technologies on platelet concentrates," *Blood Reviews* 38:235-241 (2014).
Kakaiya et al., "Platelet preservation in large containers," *Vox Sanguinis*, 46(2):111-118 (1984).
Kiani et al., "Fluctuations in microvascular blood flow parameters caused by hemodynamic mechanisms," *American Journal of Physiology*, 266(5):H1822-H1828 (1994).
Kikuchi et al., "Modified Cell-Flow Microchannels in a Single-Crystal Silicon Substrate and Flow Behavior of Blood Cells," *Microvascular Research*, 47:126-139 (1994).
Kilkson et al., "Platelet metabolism during storage of platelet concentrates at 22° C.," *Blood* 64(2):406-414 (1984).
Koch et al., "Peripheral blood leukocyte NO production and oxidative stress in multiple sclerosis," *Multiple Sclerosis*, 14:159-165 (2008).
Koch et al., "Duration of Red-Cell Storage and Complications After Cardiac Surgery," *The New England Journal of Medicine*, 358:1229-1239 (2008).
Krogh, "Studies on the physiology of capillaries. II. The reactions to local stimuli of the blood-vessels in the skin and web of the frog," *The Journal of Physiology*, 55:412-422 (1921).
Kuraoka, et al., "Ship-in-a-bottle synthesis of a cobalt phthalocyanine/porous glass composite membrane for oxygen separation," *Journal of Membrane Science*, 286(1-2):12-14 (2006).
Kynar Flex Product Catalog, downloaded May 20, 2015 from Kynar.com.
Lowndes, "Blood Interference in fluorescence Spectrum: Experiment, analysis and comparison with intraoperative measurements on brain tumor," Bachelor Thesis, Linköping University, pp. 1-42 (2010).
Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).
Lundblad, "Factor VIII—Reducing agents, copper ions, and stability," http://lundbladbiotech.com.
Mazor et al., "Prolonged Storage of Red Cells: The Effect of pH, Adenine Phosphate," *Vox Sanguinis*, 66:264-269 (1994).
McDonald et al., "Poly(dimethylsiloxane) as a Material for Fabricating Microfluidic Devices," *Accounts of Chemical Research*, 35(7):491-499 (2002).
Meryman et al., "Prolonged storage of red cells at 4° C," *Transfusion*, 26(6):500-505 (1986).
Meryman et al., "Extending the storage of red cells at 4° C," *Transfus. Sci.*, 15(2):105-115 (1994).
Moll et al., "Dean vortices applied to membrane process. Part II: Numerical approach," *Journal of Membrane Science*, 288:321-335 (2007).
Moroff et al., "Factors Influencing Changes in pH during Storage of Platelet Concentrates at 20-24° C," *Vox Sanguinis*, 42(1):33-45 (1982).
Moroff et al., "Proposed standardization of methods for determining the 24-hour survival of stored red cells," *Transfusion*, 24:109-114 (1984).
Moroff et al., "Concepts about current conditions for the preparation and storage of platelets," *Transfus Med Rev* 5:48-59 (1991).
Murphy et al., "Platelet storage at 22° C: role of gas transport across plastic containers in maintenance of viability," *Blood* 46(2):209-218 (1975).
Murphy et al., "Increased Mortality, Postoperative Morbidity, and Cost After Red Blood Cell Transfusion in Patients Having Cardiac Surgery," *Circulation*, 116:2544-2552 (2007).

(56) References Cited

OTHER PUBLICATIONS

Musante et al., "Active focal segmental Glomerulosclerosis is Associated with Massive Oxidation of Plasma Albumin," *Journal of the American Society of Nephrology*, 18(3):799-810 (2007).
Ng et al., "Components for integrated poly(dimethylsiloxane) microfluidic systems," *Electrophoresis*, 23:3461-3473 (2002).
Ohkuma et al., "The preservative-exchange method using a sextuple-bag system for a 10-week storage period of red blood cells," *Transfusion Medicine*, 1:257-262 (1991).
Parkkinen et al., "Plasma ascorbate protects coagulation factors against photooxidation," *Thromb Haemost* 75(2):292-297 (1996).
Picker et al., "Current methods for the reduction of blood-borne pathogens: a comprehensive literature review," *Blood Transfusion* 11:343-348 (2013).
Pidcoke et al., "Primary hemostatic capacity of whole blood: a comprehensive analysis of pathogen reduction and refrigeration effects over time," *Transfusion* 53:137S-149S (2013).
Poncelet et al., "Tips and tricks for flow cytometry-based analysis and counting of microparticles," *Transfus. Apher. Sci.* 53(2):110-126 (2015).
Poxton, "Antibodies to lipopolysaccharide," *Journal of Immunological Methods*, 186:1-15 (1995).
Prefiltration before membrane filtration, hydrophobic, 25 µm 142 mm, retrieved on Aug. 26, 2014, from: www.emdmillipore.com/US/en/product/Prefiltration-before-membrane-filtration.
Pries et al., "Biophysical aspects of blood flow in the microvasculature," *Cardiovascular Research*, 32:654-667 (1996).
Ramstack et al., "Shear-induced activation of platelets," *J. Biomech.*, 12:113-125 (1979).
Reynolds et al., "S-nitrosohemoglobin deficiency: A mechanism for loss of physiological activity in banked blood," *Proceedings of the National Academy of Sciences*, vol. 104, No. 43, pp. 17058-17062 (2007).
Rock et al., "Nutricel as an additive solution for neonatal transfusion," *Transfusion Science*, 20:29-36 (1999).
Sambuceti et al., "Why should we study the coronary microcirculation?," *Am J Physiol Heart Circ Physiol*, 279:H2581-H2584 (2000).
Schubert et al., "Whole blood treated with riboflavin and ultraviolet light: Quality assessment of all blood components produced by the buffy coat method," *Transfusion* 55(4):815-823 (2014).
Sheffield et al., "Changes in coagulation factor activity and content of di(2-ethylhexyl) phthate in frozen plasma units during refrigerated storage for up to 5 days after thawing," *Transfusion*, 52:494-502 (2012).
Shevkoplyas et al., "Direct measurement of the impact of impaired erythrocyte deformability on microvascular network perfusion in a microfluidic device," *Lab Chip*, 6:914-920 (2006).
Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).
Sohmer et al., "Phosphoenolypyruvate (PEP) Effects on Fresh and Stored Red Blood Cells," *Proceedings of the Society for Experimental Biology and Medicine*, 171:24-33 (1982).
Su et al., "Impermeable barrier films and protective coatings based on reduced graphene oxide," *Nature Communications* 5 Article No. 4843 (2014).
Supplementary European Search Report dated Jan. 20, 2015 in European Patent Application No. 12822387.2.
Sutera et al., "Deformation and Fragmentation of Human Red Blood Cells in Turbulent Shear Flow," *Biophys. J.*, 15:1-10 (1975).
Sutton et al., "A Novel Instrument for Studying the Flow Behaviour of Erythrocytes through Microchannels Simulating Human Blood Capillaries," *Microvascular Research*, 53:272-281 (1997).
Szymanski et al., "Effect of rejuvenation and frozen storage on 42-day-old AS-1 RBCs," *Transfusion*, 41:550-555 (2001).
Tinmouth et al., "The Clinical Consequences of the Red Cell Storage Lesion," *Transfusion Medicine Reviews*, 15(2):91-107 (2001).

Tracey et al., "A Silicon Micromachined Device for Use in Blood Cell Deformability Studies," *IEEE Transactions on Biomedical Engineering*, 42(8):751-761 (1995).
"Transition and Turbulence," https://www.princeton.edu/~asmits/Bicycle_web/transition.html . Adapted from the Engine and the Atmosphere: An Introduction to Engineering by Z. Warhaft, Cambridge University Press, (1997).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Valeri et al., "The survival, function, and hemolysis of human RBCs stored at 4° C in additive solution (AS-1, AS-3, or AS-5) for 42 days and then biochemically modified, frozen, thawed, washed, and stored at 4° C in sodium chloride and glucose solution for 24 hours," *Transfusion*, 40:1341-1345 (2000).
Wallvik et al., "Platelet Concentrates Stored at 22° C Need Oxygen the Significance of Plastics in Platelet Preservation," *Vox Sanguinis*, 45(4):303-311 (1983).
Wallvik et al., "The platelet storage capability of different plastic containers," *Vox Sanguinis*, 58(1):40-44 (1990).
Wang et al., "Fabrication of PLGA microvessel scaffolds with circular microchannels using soft lithography," *Journal of Micromechanics and Microengineering*, 17(10):2000-2005 (2007).
Weinberg et al., "Transfusions in the Less Severely Injured: Does Age of Transfused Blood Affect Outcomes?," *The Journal of TRAUMA*, 65(4):794-798 (2008).
Wring et al., "Manipulation and Flow of Biological Fuids in Straight Channels Micromachined in Silicon," *Clinical Chemistry*, 40(1):43-47 (1994).
Wood et al., "The Viability of Human Blood Stored in Phosphate Adenine Media," *Transfusion* 7, 401-408 (1967).
Wu et al., "Polymer microchips bonded by $O_2$-plasma activation," *Electrophoresis*, 23:782-790 (2002).
Yazer et al., "Coagulation factor levels in plasma frozen within 24 hours of phlebotomy over 5 days of storage at 1 to 6° C," *Transfusion*, 48:2525-2530 (2008).
Yoshida et al., "Extended storage of red blood cells under anaerobic conditions," *Vox Sanguinis*, 92:22-31 (2007).
Yoshida et al., "Storage of red blood cells under anaerobic conditions: reply," *Vox Sanguinis*, 93:184 (2007).
Yoshida et al., "The effects of additive solution pH and metabolic rejuvenation on anaerobic storage of red cells," *Transfusion*, 48:2096-2105 (2008).
Yoshida et al., "Anaerobic storage of red blood cells," *Blood Transfus*, 8:220-236 (2010).
Zhang et al., "Modification of Si(100) surface by the grafting of poly(ethylene glycol) for reduction in protein adsorption and platelet adhesion," *J Biomed Mater Res*, 56:324-332 (2001).
Zimrin et al., "Current issues relating to the transfusion of stored red blood cells," *Vox Sanguinis*, 96:93-103 (2009).
Zimring et al., "Established and theoretical factors to consider in assessing the red cell storage lesion," *Blood*, 125:2185-2190 (2015).
Extended European Search Report dated Oct. 9, 2018, in European Patent Application No. 16784043.8.
Agarwal et al., "Effect of pre-storage gamma irradiation on red blood cells," *Indian Journal of Medical Research* 122(5):385 (2005).
Extended European Search Report dated Jun. 5, 2019, in European Patent Application No. 19158815.1.
Paillous et al. "Mechanisms of photosensitized DNA cleavage," J. Photochem. Photobiol. B: Biol. 20:203-209 (1993).
Pelletier et al., "Pathogen inactivation techniques," Best Practice & Research Clinical Haematology 19(1):205-242 (2006).
Seghatchian et al., "Pathogen-reduction systems for blood components: The current position and future trends," Transfusion and Apheresis Science 35:189-196 (2006).
Zavizion et al., "Inactivation of mycoplasma species in blood by INACTINE PENT110 process," Transfusion 44:286-293 (2004).
Cardo et al., "Pathogen inactivation of *Leishmania donovani infantum* in plasma and platelet concentrates using riboflavin and ultraviolet light," *Vox Sanguinis* 90:85-91 (2006).

(56) References Cited

OTHER PUBLICATIONS

Cardo et al., "Pathogent inactivation of *Trypanosoma cruzi* in plasma and platet concentrates using riboflavin and ultraviolet light," *Transfusion and Apheresis Science* 37:131-137 (2007).
Corbin, "Pathogen Inactivation of Blood Components: Current Status and Introduction of an Approach Using Riboflavin as a Photosensitizer," International Journal of Hematology Supplement II 76:253-257 (2002).
Erickson et al., "Evaluation of in vitro Quality of Stored RBC after Treatment with S303 Pathogen Inactivation at Varying Hematocrits," Transfusion DUP—General Collection 48(2) Supplement (2008).
Fast et al., "Inactivation of Human White Blood Cells in Red Blood Cell Products Using the MIRASOL® System for Whole Blood," Blood Abstract #2897 110(11)(pt. 1) (2007).
Goodrich, "The Use of Riboflavin for the Inactivation of Pathogens in Blood Products," Vox Sanguinis Suppl. 2 78:211-215 (2000).
International Search Report for PCT/US2016/033151 dated Oct. 13, 2016.
Janetzko et al., "Pathogen reduction technology (Mirasol®) treated singledonor platelets resuspended in a mixture of autologous plasma and PAS," Vox Sanguinis 97:234-239 (2009).
Vrielink et al., "Transfusion-transmissible infections," Current Opinion in Hematology 5:396-405 (1998).
Apstein et al., "Effect of erythrocyte storage and oxyhemoglobin affinity changes on cardiac function," *Am J. Physiol* 248: H508-15 (1985).
Aydogan et al., "Impaired erythrocytes deformability in $H(2)O(2)$-induced oxidative stress: protective effect of L-carnosine," *Clin Hemorheol Microcirc* 39:93-8 (2008).
Babic, "In vitro function and phagocytosis of galactosylated platelet concentrates after longterm refrigeration," *Transfusion* 47: 442-51 (2007).
Becker et al., "Studies of platelet concentrates stored at 22 C nad 4 C," *Transfusion* 13: 61-8 (1973).
Benesch et al., "The effect of organic phosphates from the human erythrocyte on the allosteric properties of hemoglobin," *Biochem Biophys Res Commun* 26: 162-7 (1967).
Bersin et al., "Importance of oxygen-haemoglobin binding to oxygen transport in congestive heart failure," *Br Heart J* 70: 443-7 (1993).
Bordbar et al., "Identified metabolic signature for assessing red blood cell unit quality is associated with endothelial damage markers and clinical outcomes," *Transfusion* 56: 852-62 (2016).
Browne et al., "The molecular pathobiology of cell membrane iron: the sickle red cell as a model" *Free Radic Biol Med* 24: 1040-8 (1998).
Browne et al., "Removal of erythrocyte membrane iron in vivo ameliorates the pathobiology of murine thalassemia," *J Clin Invest* 100: 1459-64 (1997).
Burns et al., "Anaerobic Storage Improves the Mechanical Properties of Stored Red Blood Cells," *Transfusion* 52: 83A (2012).
Burns et al., "Deterioration of red blood cell mechanical properties is reduced in anaerobic storage," *Blood Transfus* 14: 80-8 (2016).
Cabrales et al., "Microvascular pressure and functional capillary density in extreme hemodilution with low-and high-viscosity dextran and a low-viscosity Hb-based 02 carrier," *American Journal of Physiology-Heart and Circulatory Physiology* 287: H363-H73 (2004).
Cabrales et al., "Plasma viscosity regulates systemic and microvascular perfusion during acute extreme anemic conditions," *Am J Physiol Heart Circ Physiol* 291: H2445-52 (2006).
Cannon et al., "Damage control resuscitation in patients with severe traumatic hemorrhage: A practice management guideline from the Eastern.Association for the Surgery of Trauma," *J Trauma Acute Care Surg* 82: 605-17 (2017).
Cap et al., "Whole Blood Transfusion," *Military Medicine* 183, 9/10:44 (2018).
Chanutin et al., "Effect of organic and inorganic phosphates on the oxygen equilibrium of human erythrocytes," *Arch Biochem Biophys* 121: 96-102 (1967).

Chatpun et al., "Cardiac mechanoenergetic cost of elevated plasma viscosity after moderate hemodilution," *Biorheology* 47: 225-37 (2010).
Chatpun et al., "Cardiac systolic function recovery after hemorrhage determines during shock," *J Trauma* 70: 787-93 (2011).
Chatpun et al., "Effects of plasma viscosity modulation on cardiac function during moderate hemodilution," *Asian J Transfus* Sci 4: 102-8 (2010).
Choi et al., "Influence of storage temperature on the responsiveness of human platelets to agonists," *Ann Clin Lab Sci* 33: 79-85 (2003).
Chouchani et al., "Ischaemic accumulation of succinate controls reperfusion injury through mitochondrial ROS," *Nature* 515: 431-5 (2014).
Coene, "Paired analysis of plasma proteins and coagulant capacity after treatment with three methods of pathogen reduction," *Transfusion* 54: 1321-31 (2014).
Cotton et al., "A Randomized Controlled Pilot Trial of Modified Whole Blood Versus Component Therapy in Severely Injured Patients Requiring Large Volume Transfusions," *Annals of Surgery* 258(4) (2013).
D'Alessandro et al., "Heterogeneity of blood processing and storage additives in different centers impacts stored red blood cell metabolism as much as storage time: lessons from REDS-11I-Omics," *Transfusion* 59: 89-100 (2019).
D'Alessandro et al., "Time-course investigation of SAGM-stored leukocyte-filtered red bood cell concentrates: from metabolism to proteomics," *Haematologica* 97: 107-15 (2012).
D'Alessandro et al., "Red blood cell metabolism under prolonged anaerobic storage," *Mol Biosyst* 9: 1196-209 (2013).
D'Alessandro et al., "Red blood cell metabolic responses to refrigerated storage, rejuvenation, and frozen storage," *Transfusion* 57: 1019-30 (2017).
D'Alessandro et al., "Metabolomics of AS-5 RBC supernatants following routine storage," *Vox Sang* (2014).
D'Alessandro et al., "An update on red blood cell storage lesions, as gleaned through biochemistry and omics technologies," *Transfusion* 55: 205-19 (2015).
D'Alessandro et al., "Red blood cell storage and clinical outcomes: new insights," *Blood Transfus* 15: 101-3 (2017).
D'Alessandro et al., "Plasma succinate is a predictor of mortality in critically injured patients," *Journal of Trauma and Acute Care Surgery* 83: 491-5 (2017).
D'Alessandro et al., "Plasma First Resuscitation Reduces Lactate Acidosis, Enhances Redox Homeostasis, Amino Acid and Purine Catabolism in a Rat Model of Profound Hemorrhagic Shock," *Shock* 46: 173-82 (2016).
D'Alessandro et al., "Anaerobic storage Condition enhances GSH Levels while Maintaining Pentose Phosphate Pathway Activity," *Transfusion* 56: 51A (2016).
D'Alessandro et al., "Red blood cell storage in additive solution-7 preserves energy and redox metabolism: a metabolomics approach," *Transfusion* 55: 2955-66 (2015).
D'Alessandro et al., "Routine storage of red blood cell (RBC) units in additive solution-3: a comprehensive investigation of the RBC metabolome," *Transfusion* 55: 1155-68 (2015).
D'Alessandro et al., "Omics markers of the red cell storage lesion and metabolic linkage," *Blood Transfus* 15: 137-44 (2017).
D'Alessandro et al., "AltitudeOmics: Red Blood Cell Metabolic Adaptation to High Altitude Hypoxia," *J Proteome Res* 15: 3883-95 (2016).
D'Alessandro et al., "Citrate metabolism in red blood cells stored in additive solution-3," *Transfusion* 57: 325-36 (2017).
D'Alessandro et al., "Metabolic effect of alkaline additives and guanosine/gluconate in storage solutions for red blood cells," *Transfusion* 58: 1992-2002 (2018).
D'Alessandro et al., "Effects of aged stored autologous red blood cells on human plasma metabolome," *Blood Adv* 3: 884-96 (2019).
D'Alessandro et al., "Hitchhiker's guide to the red cell storage galaxy: Omics technologies and the quality issue," *Transfits Apher Sci* 56: 248-53 (2017).

(56) References Cited

OTHER PUBLICATIONS

D'Amici, et al., "Red blood cell storage in SAGM and AS3: a comparison through the membrane two-dimensional electrophoresis proteome," *Blood Transfusion=Transfusione del sangue* 10 Suppl 2: s46-54 (2012).
Delgado et al., "Platelet Function in Stored Whole Blood Measured by a Shear-and Von Willebrand Factor-Dependent Methodology is Retained During Storage at 4° C for up to 7 Days," *Transfusion* 51: 65A (2011).
Dennis et al., "Transfusion of 2,3 DPG-enriched red blood cells to improve cardiac function," *Ann Thorac Surg* 26: 17-6 (1978).
Dennis et al., "Improved myocardial performance following high 2-3 diphosphoglycerate red cell transfusions," *Surgery* 77: 741-7 (1975).
De Wolski et al., "Metabolic pathways that correlate with post-Transfusion circulation of stored murine red blood cells," *Haematologica* 101: 578-86 (2016).
Dumont et al., "Performance of Anaerobic Stored Red Blood Cells Prepared Using a Prototype O2 & CO2 Depletion and Storage System," *Transfusion* 51s: SP89 (2011).
Dumont et al., "Randomized cross-over in vitro and in vivo evaluation of a prototype anaerobic conditioning and storage system vs. standard aerobic storage," *Vox Sang* 103: 123 (2012).
European Search Report dated Jun. 18, 2019, in European Patent Application No. 19163305.6.
Ezuki et al., "Survival and recoery of apheresis platelets stored in a polyolefin container with high oxygen permeability," *Vox Sanguinis* 94:292-298 (2008).
Farber et al., "Effect of decreased O2 affinity of hemoglobin on work performance during exercise in healthy humans," *J Lab Clin Med* 104: 166-75 (1984).
Feys, "Oxygen removal during pathogen inactivation with riboflavin and UV light preserves protein function in plasma for Transfusion," *Vox Sang* 106: 307-15 (2013).
Friesenecker et al., "Arteriolar vasoconstrictive response: comparing the effects of arginine vasopressin and norepinephrine," *Crit Care* 10: R75 (2006).
Gehrke et al., "Metabolomics evaluation of early-storage red blood cell rejuvenation at 4 degrees C and 37 degrees C," *Transfusion* 58: 1980-91 (2018).
Gevi et al., "Alterations of red blood cell metabolome during cold liquid storage of erythrocyte concentrates in CPD-SAGM," *J Proteomics* 76 Spec No. 168-80 (2012).
Golan et al., "Transfusion of fresh whole blood stored (4 degrees C) for short period fails to improve platelet aggregation on extracellular matrix and clinical hemostasis after cardiopulmonary bypass," *J Thorac Cardiovasc Surg* 99: 354-60 (1990).
Haddaway et al., "Hemostatic properties of cold-stored whole blood leukoreduced using a platelet-sparing versus a non-platelet-sparing filter," *Transfusion* (2019).
Hebbel, et al., Oxidation-induced changes in microrheologic properties of the red blood cell membrane. *Blood* 1990;76: 1015-20.
Hebbel, "Auto-oxidation and a membrane-associated 'Fenton reagent': a possible explanation for development of membrane lesions in sickle erythrocytes," *Clin Haematol* 14: 129-40 (1985).
Hershko, "Mechanism of iron toxicity and its possible role in red cell membrane damage," *Semin Hematol* 26: 277-85 (1989).
Hess et al., "Advances in military, field, and austere Transfusion medicine in the last decade," *Transfus Apher Sci* 49: 380-6 (2013).
Hornsey et al., "Cold storage of pooled, buffy-coat-derived, leucoreduced platelets in plasma," *Vox Sang* 95 26-32 (2008).
Jagannathan et al., "Oxidative stress under ambient and physiological oxygen tension in tissue culture," *Curr Pharmacol Rep* 2: 64-72 (2016).
Jarman et al., "Rural risk: Geographic disparities in trauma mortality," *Surgery* 160: 1551-9 (2016).
Jarolim et al., "Effect of hemoglobin oxidation products on the stability of red cell membrane skeletons and the associations of skeletal proteins: correlation with a release of them in," *Blood* 76: 2125-31 (1990).

Jenkins et al., "Trauma hemostasis and oxygenation research position paper on remote damage control resuscitation: definitions, current practice, and knowledge gaps," *Shock* 41 Suppl 1: 3-12 (2014).
Jeseth et al., "Oxygen dissociation after Transfusion of blood stored in ACD or CPD solution," *J Thorac Cardiovasc Surg* 70: 35-9 (1975).
Jobes et al., "Toward a definition of "fresh" whole blood: an in vitro characerization of coagulation properties in refrigerated whole blood for Transfusion," *Transfusion* 51: 43-51 (2011).
Jy et al., "Release of Microparticles During Blood Storage Is Influenced by Residual Platelets, Leukocytes and Oxygen Levels," *Blood* 120: 3435 (2012).
Kerger et al., "Systemic and subcutaneous microvascular pO2 dissociation during 4-h hemorrhagic shock in conscious hamsters," *Am J. Physiol* 270: H827-H36 (1996).
Khorana et al., "Blood Transfusions, thrombosis, and mortality in hospitalized patients with cancer," *Arch Intern Med* 168: 2377-81 (2008).
Kohli et al., "Packed red cells versus whole blood transfusion for severe paediatric anaemia, pregnancy-related anaemia and obstetric bleeding: an analysis of clinical proactice buidelines from sub-Saharan Africa and evidence underpinning recommendments," *Tropical Medicine and International Health* 24(1):11-22 (2019).
Korsten et al., "Determination of %5O2 in More Than 1300 Fresh Erythrocyte Concentrates by Resonance Raman Spectroscopy," *Transfusion* 58: 215A (2018).
Korwal et al., "The Effect of a Golden Hour Policy on the Morbidity and Mortality of Combat Casualties," *JAMA Surg* 151: 15-24 (2016).
Kreuger et al., "A clinical evaluation of citrate-phosphate-dextrose-adenine blood," *Vox Sang* 29: 81-9 (1975).
Kwan et al., "Microfluidic analysis of cellular deformability of normal and oxidatively damaged redd blood cells," *Am J Hematol* 88: 682-9 (2013).
Liu et al., "Beneficial Role of Erythrocyte Adenosine A2B Receptor-Mediated AMP-Activated Protein Kinase Activation in High-Altitude Hypoxia," *Circulation* 134: 405-21 (2016).
Manno et al., "Comparison of the hemostatic effects of fresh whole blood, stored whole blood, and components after open heart surgery in children," *Blood* 77: 930-6 (1991).
Miller, "New evidence in trauma resuscitation-is 1: 1: 1 the answer?" *Perioperative medicine* 2: 13 (2013).
Mollison, "The Introduction of Citrate as an Anticoagulant for Transfusion and of Glucose as a Red Cell Preservative," *British Journal of Haematology* 108:1318 (2000).
Mussano et al., "Cytokine, chemokine and growth factor profile of Platelet Rich Plasma," *Universita Degli Studi Di Tornio* 2016.
Nair et al., "Cold-Stored Platelets in PAS Exhibit Superior Hemostatic Potential" *Blood* 126: 772 (2015) Abstract.
Nemkov et al., "Metabolomics in Transfusion medicine," *Transfusion* 56: 980-93 (2015).
Nemkov et al., "Hypoxia modulates the purine salvage pathway and decreases red blood cell and supernatant levels of hypoxanthine during refrigerated storage," *Haematologica* 103: 361-72 (2018).
Nemkov et al., "Metabolism of Citrate and Other Carboxylic Acids in Erythrocytes as a Function of Oxygen Saturation and Refrigerated Storage," *Front Med (Lausanne)* 4: 175 (2017).
Nessen et al., "Fresh whole blood use by forward surgical teams in Afghanistan is associated with improved survival compared to component therapy without platelets," *Transfusion* 53:107S-113S (2013).
Nilsson et al., "Association between venous thromboembolism and perioperative allogeneic Transfusion," *Arch Surg* 142: 126-32; discussion 33 (2007).
Paglia et al., "Biomarkers defining the metabolic age of red blood cells during cold storage," *Blood* 128: e43-50 (2016).
Pallotta et al., "Storing red blood cells with vitamin C and N-acetylcysteine prevents oxidative stress-related lesions: a metabolomics overview," *Blood Transfus* 12: 376-87 (2014).

(56) References Cited

OTHER PUBLICATIONS

Pallotta et al., "Supplementation of anti-oxidants in leucofiltered erythrocyte concentrates: assessment of morphological changes through scanning electron microscopy," *Blood Transfus* 12: 421-4 (2014).
Pidcoke et al., "Tenyear analysis of Transfusion in Operation Iraqi Freedom and Operation Enduring Freedom: increased plasma and platelet use correlates with improved survival," *Journal of Trauma and Acute Care Surgery*;73: S445-S52 (2012).
Prudent, et al., "Oxygen in Red Blood Cell Concentrates Influence of Donor's Characteristics, Location and Blood Processing," *Vox Sang* 113: 116 (2018).
Reisz et al., "Red blood cells in hemorrhagic shock: a critical role for glutaminolysis in fueling alanine transamination in rats," *Blood Advances* 1:1296-305 (2017).
Reisz et al., "Methylation of protein aspartates and deamidated asparagines as a function of blood bank storage and oxidative stress in human red blood cells," *Transfusion* 58: 2978-91 (2018).
Reisz et al., "Metabolic Linkage and Correlations to Storage Capacity in Erythrocytes from Glucose 6-Phosphate Dehydrogenase-Deficient Donors," *Front Med (Lausanne)* 4: 248 (2017).
Reisz et al., "Oxidative modifications of glyceraldehyde 3-phosphate dehydrogenase regulate metabolic reprogramming of stored red blood cells," *Blood* 128: e32-42 (2016).
Risbano et al., "Effects of Aged Stored Autologous Red Blood Cells on Human Endothelial Function," *Am J Respir Crit Care Med* 192: 1223-33 (2015).
Rolfsson et al., "Metabolomics comparison of red cells stored in four additive solutions reveals differences in citrate anticoagulant permeability and metabolism," *Vox Sang* (2017).
Scott et al., "Effect of excess alpha-hemoglobin chains on cellular and membrane oxidation in model beta-thalassemic erythrocytes," *J Clin Invest* 91: 1706-12 (1993).
Seok et al., "Genomic responses in mouse models poorly mimic human inflammatory diseases," *Proceedings of the National Academy of Sciences* 110: 3507-12 (2013).
Sivertsen et al., "Preparation of leukoreduced whole blood for Transfusion in austere environments; effects of forced filtration, storage agitation, and high temperatures on hemostatic function," *J Trauma Acute Care Surg* 84: S93-S103 (2018).
Shalev et al., "Extremely high avidity association of Fe(III) with the sickle red cell membrane," *Blood* 88: 349-52 (1996).
Shapiro, "To filter blood or universal leukoreduction: what is the answer?," *Critical Care* 8(Suppl 2): S27-draftS30 (2004).
Snyder et al., "In vitro and in vivo evaluation of a whole blood platelet-sparing leukoreduction filtration system," *Transfusion* 50: 2145-51 (2010).
Spinella et al., "Prehospital hemostatic resuscitation to achieve zero preventable deaths after traumatic injury," *Curr Opin Hematol* (2017).
Spinella et al., "Whole blood: back to the future," *Curr Opin Hematol* 23: 536-42 (2016).
Spinella et al., "Whole blood for hemostatic resuscitation of major bleeding," *Transfusion* 56:S190-S202 (2016).
Strandenes et al., "Emergency Whole-Blood Use in the Field: a Simplified Protocol for Collection and Transfusion," *SHOCK* 41(Suppl 1):76-83 (2014).
Strandenes et al., "Low Titer Group O Whole Blood in Emergency Situations," *SCHOCK* 41(Suppl 1): 70-75 (2014).
Sun et al., "Purinergic control of red blood cell metabolism: novel strategies to improve red cell storage quality," *Blood Transfus* 15: 535-42 (2017).
Sun, et al., "Sphingosine-1-phosphate promotes erythrocyte glycolysis and oxygen release for adaptation to high-altitude hypoxia," *Nat Commun* 7: 12086 (2016).
Tannahill et al., "Succinate is an inflammatory signal that induces IL-Ibeta through HIF-Ialpha" *Nature* 496: 238-42 (2013).
Teisseire et al., "Induced low P50 in anesthetized rats: blood gas, circulatory and metabolic adjustments," *Respir Physiol* 58: 335-44 (1984).
Tolinski, "Getting the Most out of Polypropylene, Polythylene and TPO," *Additives for Polyolefins*, Second Edition 2015.
Tsai et al., "Microvascular perfusion upon exchange Transfusion with stored red blood cells in normovolemic anemic conditions," *Transfusion* 44: 1626-34 (2004).
Tsantes et al., "Redox imbalance, macrocytosis, and RBC homeostasis," *Antioxid Redox Signal* 8: 1205-16 (2006).
Valeri et al., "Improved oxygen delivery to the myocardium during hypothermia by perfusion with 2,3 DPG-enriched red blood cells," *Am Thorac Surg* 30: 527-35 (1980).
Valeri, "Circulation and hemostatic effectiveness of platelets stored at 4 C or 22 C: studies in aspirintreated normal volunteers," *Transfusion* 16: 20-3 (1976).
Valeri, "Hemostatic effectiveness of liquid-preserved and previously frozen human platelets," *N Engl J Med* 290: 353-8 (1974).
Van Buskirk et al., "Comparison of Cytokine, Cell-free Hemoglobin, and Isoprostane Accumulations in Packed Red Blood Cells During Novel Anaerobic and Conventional Cold Storage," Transfusion 54S: SP53 (2014).
Van Buskirk et al., "Comparison of microparticles production in packed red blood cells stored under anaerobic and conventional cold storage condition," *Vox Sang* 105 (S1): 150 (2007).
Van Buskirk et al., "Evaluation of Select Red Blood Cell Biochemical and Coagulation Properties in Whole Blood Stored Using a Novel Anaerobic Storage Platform," *Transfusion* 56: 54A (2016).
Van Slyke, "An Apparatus for Determination of the Gases in Blood and Other Solutions," *Chemistry* 7:229-231 _1921.
Voigt et al., "Effects of a restrictive Blood Transfusion protocol on acute pediatric burn care: Transfusion threshold in pediatric burns," *J Trauma Acute Care Surg* 85: 1048-54 (2018).
Williams, "Blood Transfusion on Cruise Ships; A 36 Month Review of Preliminary Data," *THOR Trauma Hemostasis & Oxygenation Research Network, RDCR Symposium, Bergen* (2013).
Williams et al., "Transfusion of Anaerobically Stored Red Blood Cells Improves Recovery in Experimental Rat Hemorrhagic Shock Model," *Transfusion* 57: 33A (2017).
Williams et al., "Transfusion of Anaerobically Stored Red Blood Cells Improves Recovery in Experimental Rat Hemorrhagic Shock Model," *Shock Abstract* (2019).
Wolfe et al., "Molecular defect in the membrane skeleton of blood bank-stored red cells. Abnormal spectrin-protein 4.1-actin complex formation," *J Chu Invest* 78:1681-6 (1986).
Wolfe, "Oxidative injuries to the red cell membrane during conventional blood preservation," *Semin Hematol* 26: 307-12 (1989).
Woodson, "Functional consequences of altered blood oxygen affinity," *Acta Biol Med Ger* 40: 733-6 (1981).
Yalcin et al., "Increased hemoglobin 02 affinity protects during acute hypoxia," *Am J. Physiol Heart Circ Physiol* 303: H271-81 (2012).
Yhap et al., "Decreased oxygen uptake with stored blood in the isolated hindlimb" *J Appl Physiol* 38: 882-885 (1975).
Yoshida et al., "Oxygen content—uncontrolled and overlooked parameter associated with stored red cell concentrate: Unexpectedly wide distribution," *Vox Sang* 112: P-244 (2017) Abstract.
Yoshida et al., "Enhancing uniformity and overall quality of red cell concentrate with anaerobic storage," *Blood Transfus* 15: 172-81 (2017).
Yoshida et al., "Toward a comprehensive biochemical model of human erythrocyte: relationship between metabolic and osmotic state of the cell and the state of hemoglobin," *Prog Clin Biol Res* 319: 179-93; discussion 94-6 (1989).
Yoshida et al., "Unexpected Variability of Hemoglobin Oxygen Saturation in Packed Red Blood Cells upon Donation Suggests Uncontrolled and Overlooked Parameter Associated with the Development of the Storage Lesion," *Transfusion* 57 (2017).
Yoshida et al., "Red blood cell storage lesion: causes and potential clinical consequences" *Blood Transfus* 17: 27-52 (2019).
Yoshida et al., "Reduction of Microparticle Generation During Anaerobic Storage of Red Blood Cells," *Transfusion* 52: 83A (2012).
Yuasa et al., "Improved extension of platelet storage in a polyolefin container with higher oxygen permeability," *British Journal of Hematology* 126:153-159 (2004).

(56) References Cited

OTHER PUBLICATIONS

Zaroulis, et al., "Lactic acidemia in baboons after Transfusion of red blood cells with improved oxygen transport function and exposure to severe arterial hypoxemia," *Transfusion* 19: 420-5 (1979).

Zeilinski et al., "Back to the future: The renaissance of whole-blood transfusions for massively hemorrhaging patients," *Surgery* 155(5) 883-886 (2014).

Zielinski, et al., "Prehospital Blood Transfusion programs: Capabilities and lessons learned," *J Trauma Acute Care Surg* 82: S70-s8 (2017).

Zingarelli et al., "Part I: Minimum Quality Threshold in Preclinical Sepsis Studies (MQTiPSS) for study design and humane modeling endpoints," *Shock* 51:10-22 (2019).

Zink et al., "Noninvasive Evaluation of Active Lower Gastrointestinal Bleeding: Comparison Between Contrast-Enhanced MDCT and 99mTcLabeled RBC Scintigraphy," *American Journal of Roentgenology* 191: 1107-14 (2008).

Zinkham et al., "Carboxyhemoglobin levels in an unstable hemoglobin disorder (Hb Zurich): effect on phenotypic expression," *Science* 209: 406-8 (1980).

\* cited by examiner

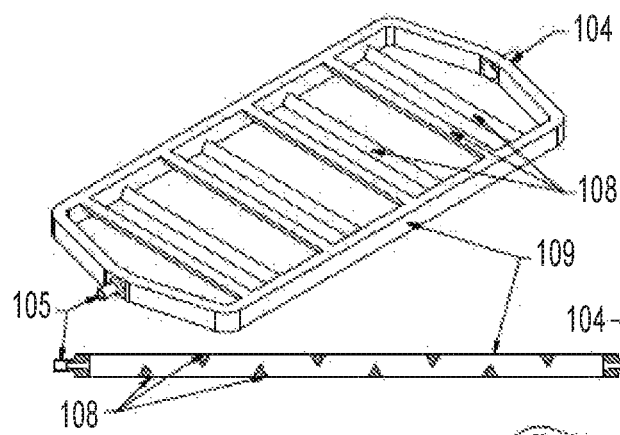
FIG. 2A
FIG. 2B
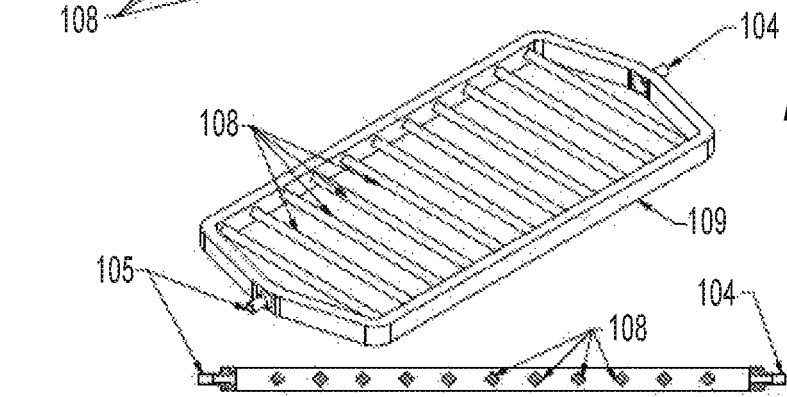
FIG. 2C
FIG. 2D
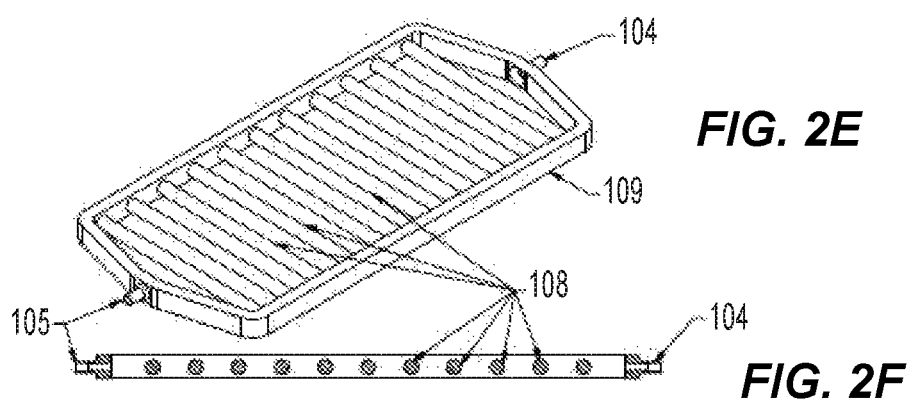
FIG. 2E
FIG. 2F

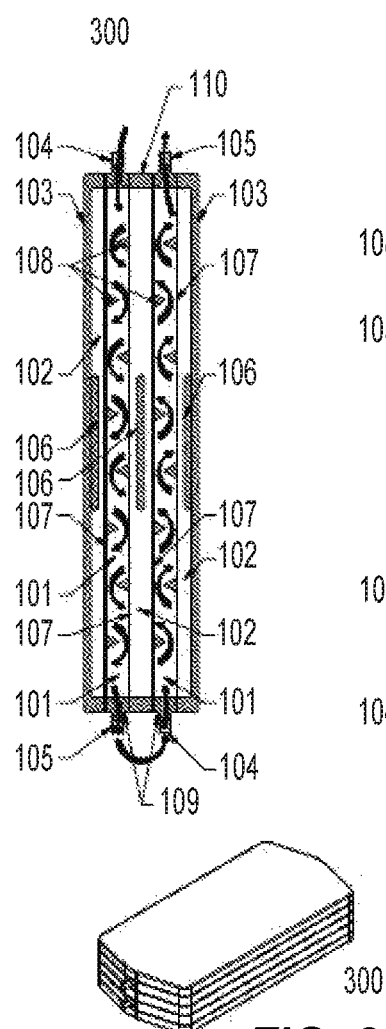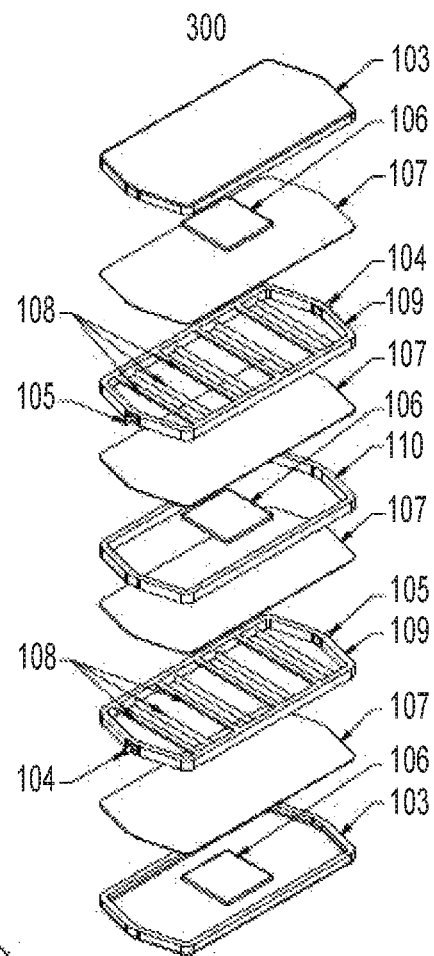
FIG. 3A
FIG. 3B
FIG. 3C

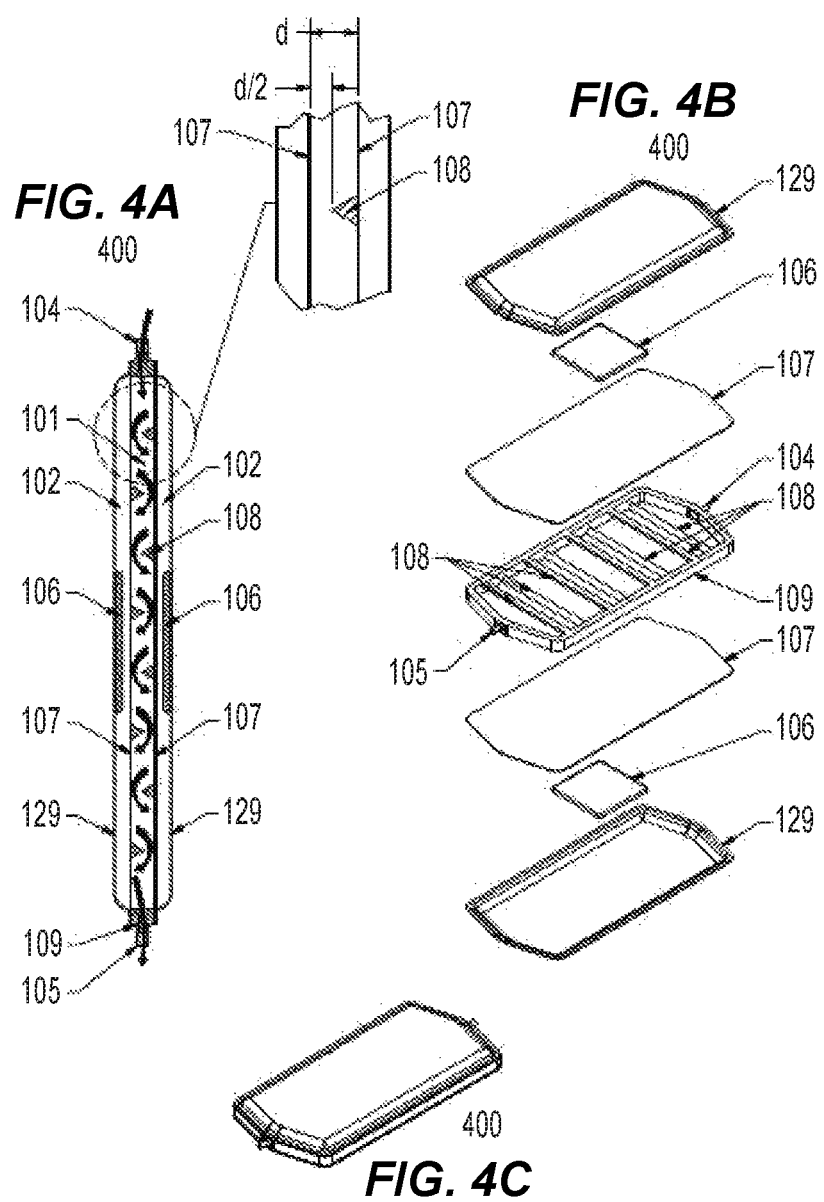

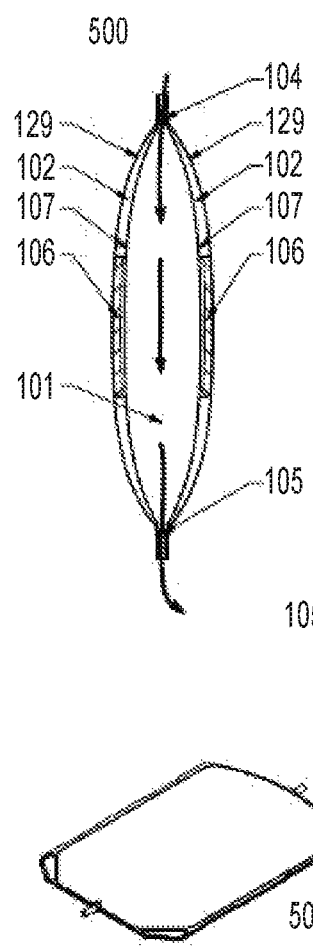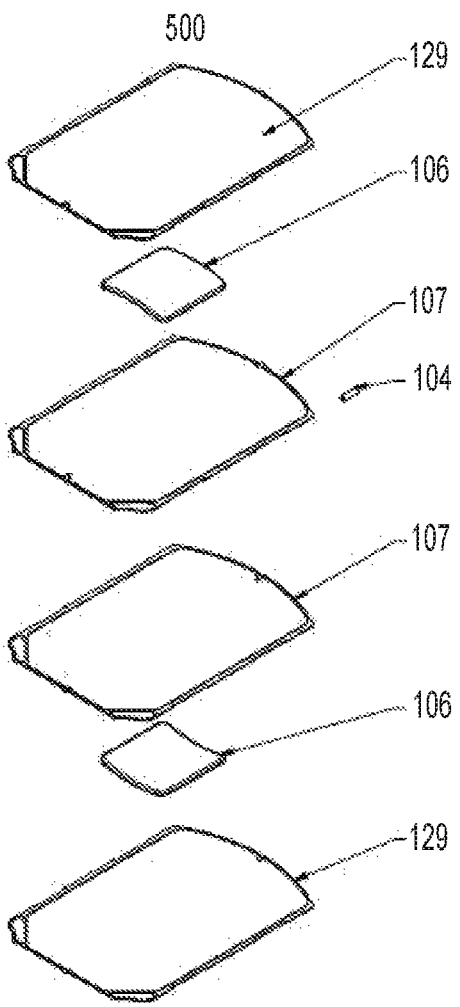
FIG. 5A
FIG. 5B
FIG. 5C

600

600

600

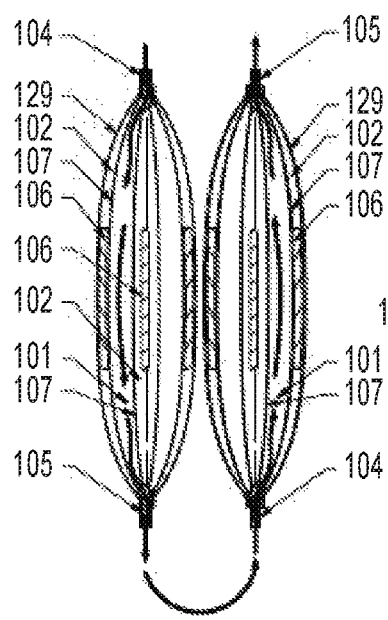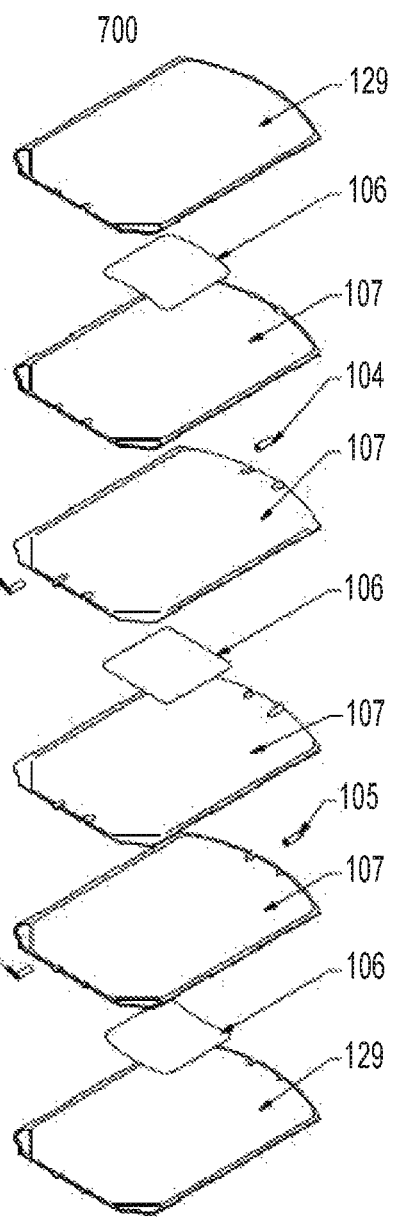

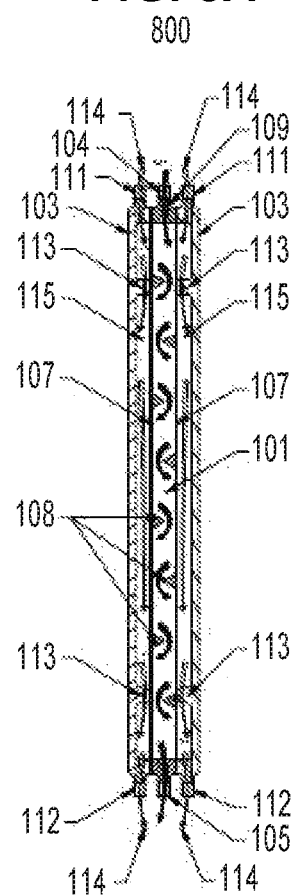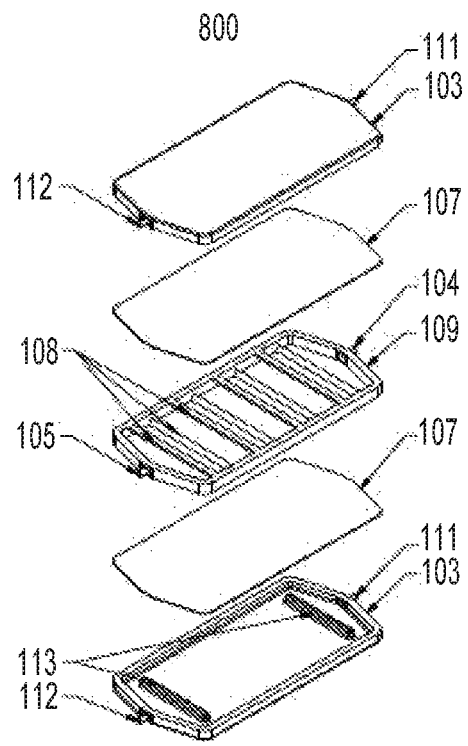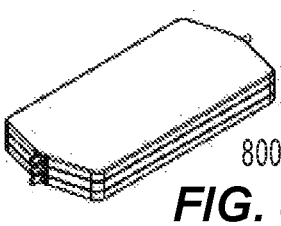
FIG. 8A
800
FIG. 8B
800
FIG. 8C
800

900

900

900

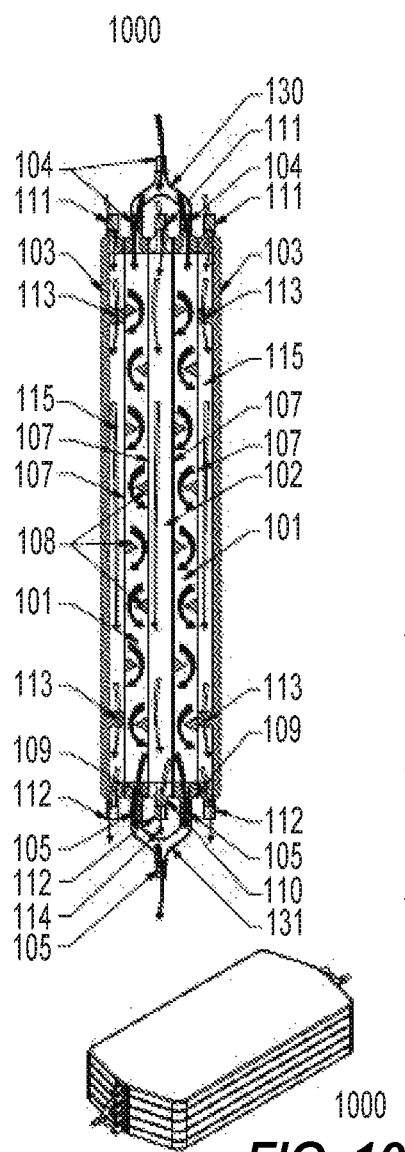
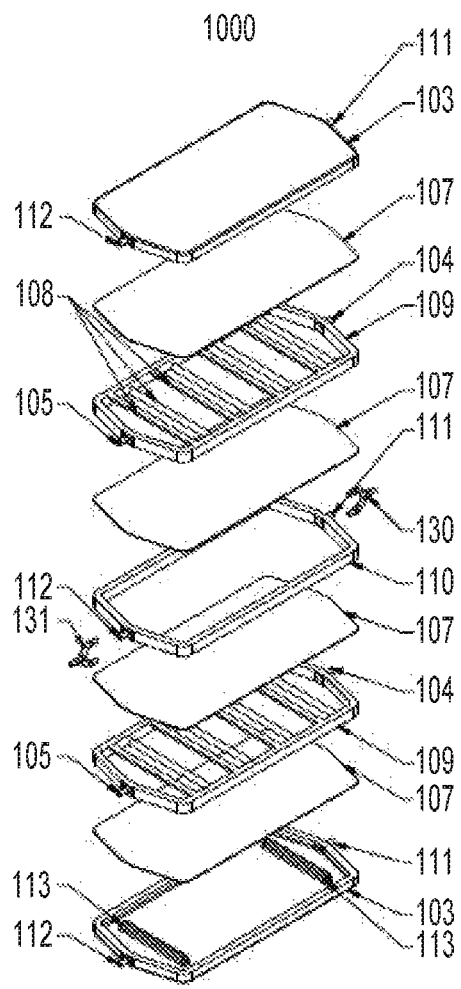
FIG. 10A
1000
FIG. 10B
1000
FIG. 10C
1000

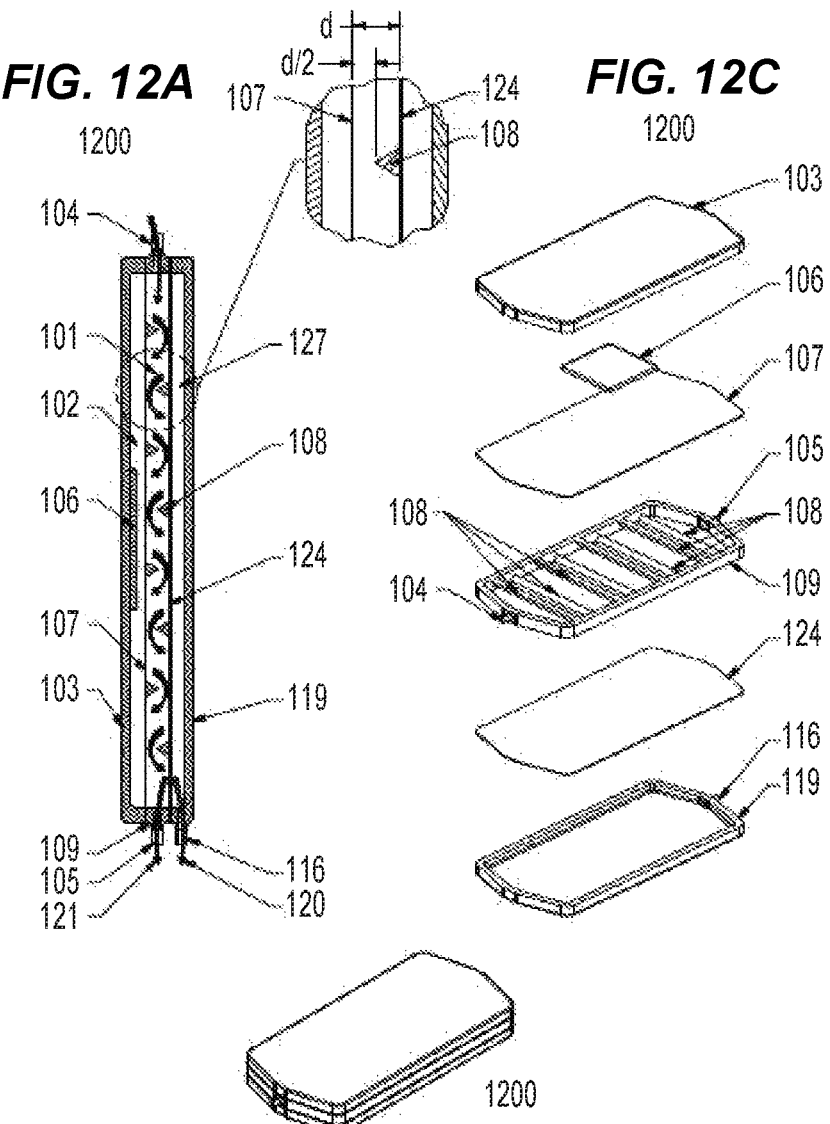

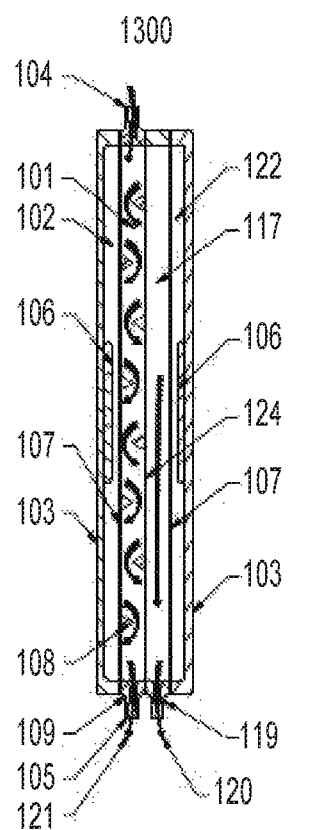
FIG. 13A
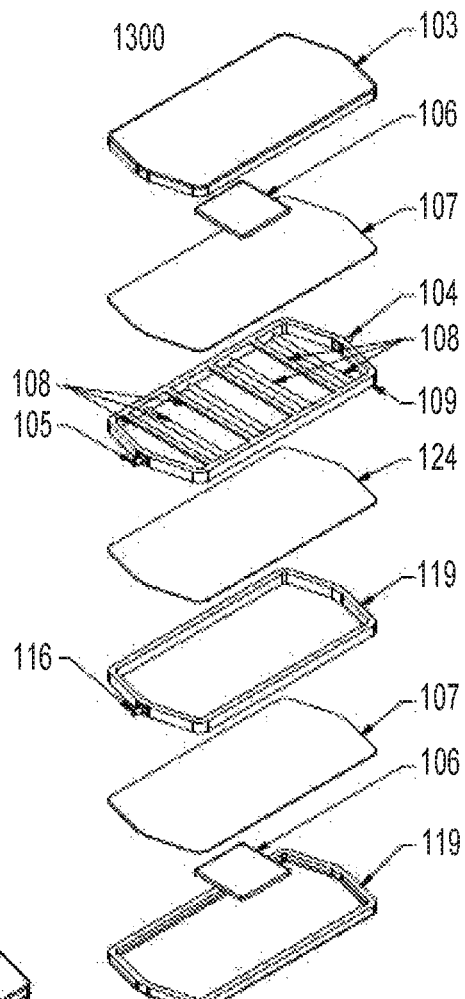
FIG. 13B
FIG. 13C

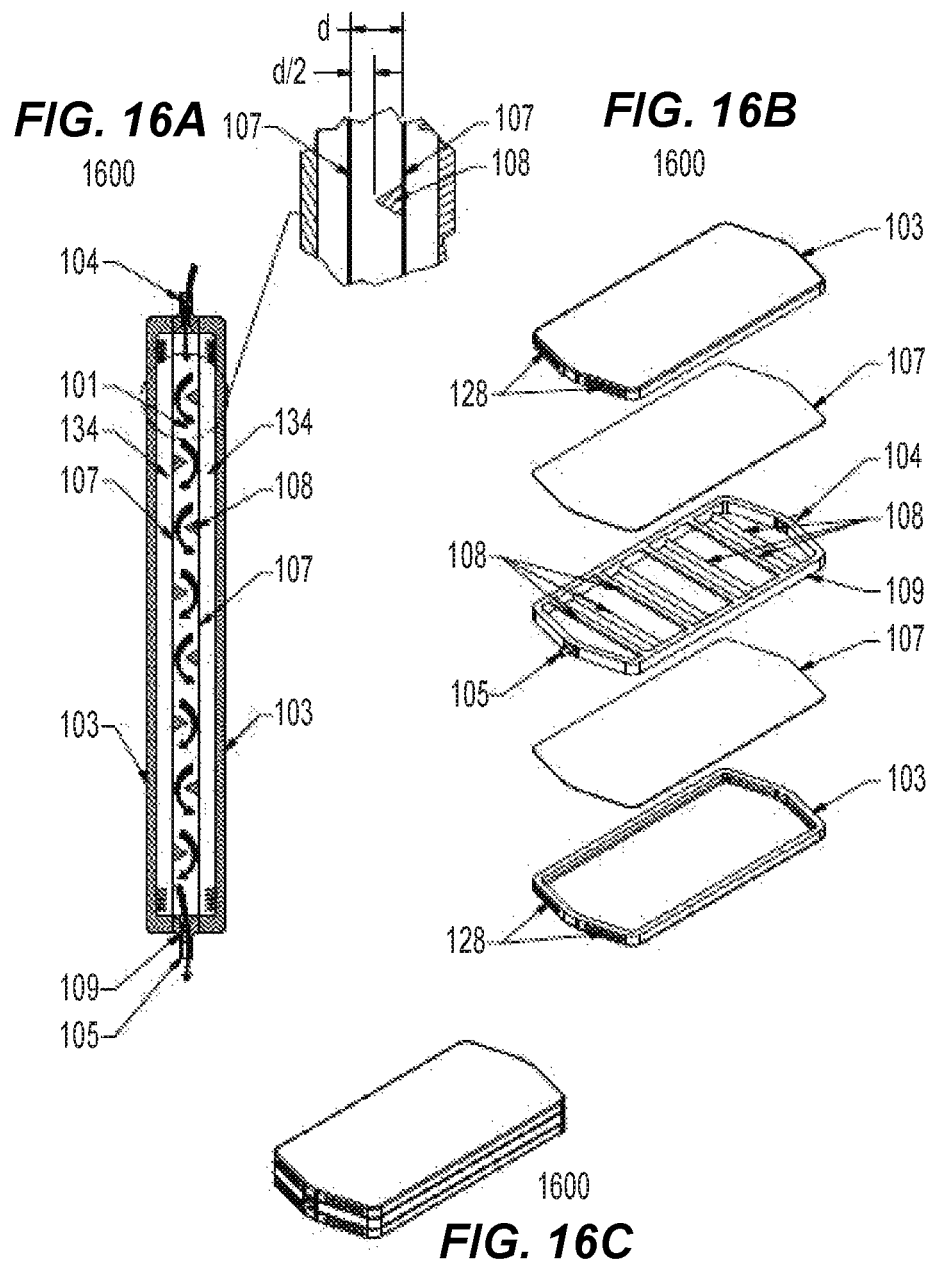

GAS DEPLETION AND GAS ADDITION DEVICES FOR BLOOD TREATMENT

CROSS-REFERENCE TO RELATED APPLICATIONS

This application is a continuation of U.S. application Ser. No. 14/771,438 filed Aug. 28, 2015, which is a 371 of International Application Serial No. PCT/US2014/019537, filed on Feb. 28, 2014, which claims the benefit of U.S. Provisional Application Ser. No. 61/770,516, filed Feb. 28, 2013. All of the foregoing applications are incorporated by reference in their entirety.

BACKGROUND OF THE INVENTION

Field of the Invention

The present disclosure includes to the devices, methods and systems for the preservation of blood products and red blood cells. More particularly, the disclosure includes devices for the removal of gases from the systems and methods for the prolonged anaerobic storage of red blood cells from blood products and the restoration of gases to blood products prior to transfusion. The disclosure also provides for devices to restore gases prior to transfusion.

Background of the Invention

Supplies of liquid blood are currently limited by storage systems used in conventional blood storage practice. Using current systems, stored blood expires after a period of about 42 days of refrigerated storage at a temperature above freezing (i.e., 4° C.) as packed blood cell preparations. Deterioration occurs even before day 42. Expired blood cannot be used and must be discarded because it will harm the ultimate recipient. One of the primary reasons for blood spoilage is its continued metabolic activity after it is stored. For example, in 2007, more than 45 million units of red blood cells (RBCs) were collected and stored globally (15.6 million in the US). During refrigerated storage, RBCs become progressively damaged by storage lesions. When transfused within the current 6-week limit, stored RBCs have lower quality (fraction of RBC removed; compromised $O_2$ delivery capacity) as well as potential toxicity, often manifested as side effects of transfusion therapy. These storage lesions are observed as altered biochemical and physical parameters associated with stored cells. Examples of these include in vitro measured parameters such as reduced metabolite levels (ATP and 2,3-DPG), reduced surface area, echinocytosis, phosphatidylserine exposure, and reduced deformability.

Stored blood undergoes steady deterioration which is partly caused by hemolysis, hemoglobin degradation and reduced adenosine triphosphate (ATP) concentration that occur during the storage period. These reasons and others limit the amount of readily available high quality blood needed for transfusions.

As discussed above, when RBCs are stored under refrigeration at temperatures above freezing (e.g., 1-6° C., standard storage conditions) in a blood storage bag, away from mechanical stress and the constantly cycling environment of the circulation, the senescence process is partially suspended. However, with the lack of constant nutrient replenishment and waste removal under refrigerated storage, RBCs are gradually damaged, resulting in compromised physiological functions. By way of example, the following problems occur during extended storage:

When RBCs are stored for an extended period, storage lesions accumulate and deteriorate RBCs and cause the up to 1% of RBCs to be hemolyzed during storage and up to 25% to be removed shortly after transfusion.

Non-viable RBCs cause iron overload in chronically transfused patients.

Transfusion does not always achieve the intended outcome of increased tissue perfusion.

Hemoglobin in RBCs do not release oxygen efficiently at tissues due to loss of 2,3-DPG.

RBCs are not able to enter and perfuse capillary beds due to loss of deformability.

Transfusing RBCs stored for longer periods may result in higher morbidity and longer hospital stays compared to transfusing "fresher" red cells. Higher morbidity and longer hospital stays result with RBCs that are stored longer than 6 weeks, in comparison to fresher red cells. For example, negative clinical outcomes in cardiac surgery occur when using "older" blood; multiple organ failure in surgical patients reflecting the age of transfused red cells; correlation between older units and increased mortality in severe sepsis; failure to improve $O_2$ utilization attributed to decreased 2,3-DPG and decreased cardiac index associated with increased blood viscosity.

The ineffectiveness and negative consequences of transfusion are attributed at least in part to the compromising effects of extended storage of RBCs. In addition to immediate removal by the recipient of certain RBCs, consequences of RBC storage lesions include: (i) depletion of ATP (loss of RBC's ability to dilate the pre-capillary arteriole); (ii) depletion of 2,3-DPG; (iii) accumulation of oxidative damage caused by reactive oxygen species (ROS) formed by the reaction of denatured hemoglobin with $O_2$; and (iv) decreased RBC deformability and increased RBC viscosity caused in part by oxidative damage to membrane and cytoskeleton. Less deformable RBCs are excluded from capillary channels resulting in low capillary occupancy and reduced tissue perfusion. Massive transfusion of undeformable cells may also contribute to multiple organ failure by blocking the organs' capillary beds. After transfusion, 2,3-DPG is synthesized relatively quickly in vivo to ~50% of the normal level in as little as 7 hours and to ~95% of the normal level in 2-3 days. However, since 2,3-DPG-depleted cells do not recover their levels immediately, $O_2$-carrying capacity is compromised to the detriment of critically ill patients requiring immediate $O_2$ delivery and tissue perfusion. There are numerous reports that emphasize the importance of RBCs with high oxygen carrying capacity in such clinical situations.

Storage of frozen blood is known in the art, but such frozen blood has limitations. For a number of years, frozen blood has been used by blood banks and the military for certain high-demand and rare types of blood. However, frozen blood is difficult to handle. It must be thawed which makes it impractical for emergency situations. Once blood is thawed, it must be used within 48 hours. U.S. Pat. No. 6,413,713 to Serebrennikov is directed to a method of storing blood at temperatures below 0° C.

U.S. Pat. No. 4,769,318 to Hamasaki et al. and U.S. Pat. No. 4,880,786 to Sasakawa et al. are directed to additive solutions for blood preservation and activation. U.S. Pat. No. 5,624,794 to Bitensky et al., U.S. Pat. No. 6,162,396 to Bitensky et al., and U.S. Pat. No. 5,476,764 to Bitensky are directed to the storage of red blood cells under oxygen-depleted conditions. U.S. Pat. No. 5,789,151 to Bitensky et al. is directed to blood storage additive solutions.

Additive solutions for blood preservation and activation are known in the art. For example, Rejuvesol™ (available from enCyte Corp., Braintree, Mass.) is added to blood after cold storage (i.e., 4° C.) just prior to transfusion or prior to freezing (i.e., at −80° C. with glycerol) for extended storage. U.S. Pat. No. 6,447,987 to Hess et al. is directed to additive solutions for the refrigerated storage of human red blood cells.

The effects of elevation and preservation of ATP levels in blood storage situations has been studied. For example, in "Studies In Red Blood Cell Preservation-7. In Vivo and in Vitro Studies with a Modified Phosphate-Ammonium Additive Solution," by Greenwalt et al., Vox Sang 65, 87-94 (1993), the authors determined that the experimental additive solution (EAS-2) containing in mM: 20 $NH_4Cl$, 30 $Na_2HPO_4$, 2 adenine, 110 dextrose, 55 mannitol, pH 7.15, is useful in extending the storage shelf-life of human RBCs from the current standard of 5-6 weeks to an improved standard of 8-9 weeks. Packed RBCs are suitable for transfusion following the removal of the supernatant with a single washing step. Greenwalt et al. also conclude that factors other than ATP concentration appear to play an increasingly important role in determining RBC viability after 50 days of storage. They cite the results of L. Wood and E. Beutler in "The Viability of Human Blood Stored in Phosphate Adenine Media," Transfusion 7, 401-408 (1967), and find in their own experiments that the relationship between ATP concentration and 24-hour RBC survival measurements appears to become less clear after about 8 weeks of storage. E. Beutler and C. West restate that the relationship between red cell ATP concentration and viability is a weak one after prolonged periods of storage in "Storage of Red Cell Concentrates in CPD-A2 for 42 and 49 Days," J. Lab. Clin. Med. 102, 53-62 (1983).

Certain patents have addressed different aspects of blood storage. One such patent is U.S. Pat. No. 4,837,047 to Sato et al. which relates to a container for storing blood for a long period of time to keep the quality of the blood in good condition. Sato et al. is directed at improving the storage life of the stored blood by maintaining a partial pressure of carbon dioxide gas in the blood at a low level. Such partial pressure is apparently obtained through normalization with the outside atmosphere. The container is made of a synthetic resin film which has a high permeability to carbon dioxide gas for the purpose of making it possible for the carbon dioxide gas to easily diffuse from the blood to outside. However, the problems caused by the interaction of the oxygen and hemoglobin in the blood are not addressed.

Another patent, U.S. Pat. No. 5,529,821 to Ishikawa et al. relates to a container and a method for the storage of blood to prevent adhesion of the blood to the container. Blood is stored in containers composed of a sheet material having a plurality of layers where a first sheet which contacts the blood substantially prevents the activation and adhesion of blood platelets to the layer. Again, however, the problems caused by the interaction of the oxygen and hemoglobin in the blood are not addressed.

In light of current technology, there is a need to improve the quality of red blood cells that are to be stored and to extend the storage life of such red blood cells in advance of transfusion to minimize morbidity associated with transfusions.

SUMMARY OF THE INVENTION

The present disclosure includes and provides a depletion device for removing a gas from a liquid including an enclosure having one or more liquid chambers, one or more depletion chambers, at least one gas permeable barrier separating the one or more liquid chambers from the one or more depletion chambers, at least one liquid inlet and at least one liquid outlet.

The present disclosure includes and provides a gas addition device including an enclosure, one or more liquid chambers, one or more gas addition chambers, at least one gas permeable barrier separating at least one of the liquid chambers from a gas addition chamber, at least one liquid inlet and at least one liquid outlet.

The present disclosure further includes and provides for a method of preparing a blood product for transfusion including flowing a blood product liquid through a depletion device to prepare a blood product having a increased level of gas.

Additionally, the present disclosure includes and provides a method for extended storage of red blood cells including obtaining whole blood, passing the whole blood through a depletion device to prepare a depleted blood product, storing the depleted blood product in a gas impermeable storage bag for a period of time to prepare a stored depleted blood product, and passing the stored depleted blood product through a gas addition device to prepare a transfusion blood product.

In embodiments according to the present disclosure, the method for extended storage of red blood cells may further include editing the transfusion blood product, irradiating the transfusion blood product, performing a buffer exchange of the transfusion blood product, collecting the gas restored blood product in a transfusion bag and combinations thereof.

The present disclosure also includes and provides for a system for extended storage of red blood cells including a phlebotomy needle, a blood collection bag, an additive solution, a depletion device, a device for leukocyte reduction, a device for editing red blood cells, a device for inactivating pathogens, a device for reducing the volume of a blood product, a device for exchanging the buffer of a blood product, a gas impermeable storage bag for storing a blood product, a device for adding a gas to the stored blood product prior to transfusion, and tubing connecting the devices, the collection bag, and the storage bag.

BRIEF DESCRIPTION OF THE DRAWINGS

FIG. 1A illustrates a cross-sectional view of a single liquid chamber depletion device. FIG. 1B illustrates a magnified view of a cross-section of a single liquid chamber depletion device. FIG. 1C illustrates separated components of a single liquid chamber depletion device. FIG. 1D illustrates an exemplary single liquid chamber depletion device.

FIGS. 2A-F illustrate exemplary flow control features according to the present disclosure. FIG. 2A illustrates an exemplary top view of triangular flow control features. FIG. 2B illustrates an exemplary cross-sectional view of triangular flow control features. FIG. 2C illustrates an exemplary top view of square shaped flow control features. FIG. 2D illustrates a exemplary cross-sectional view of square shaped flow control features. FIG. 2E illustrates an exemplary top view of circular flow control features. FIG. 2F illustrates an exemplary cross-sectional view of circular flow control features.

FIGS. 3A-C illustrate an exemplary depletion device having more than one liquid chamber according to the present disclosure. FIG. 3A illustrates an exemplary cross-sectional view of a depletion device having more than one liquid chamber. FIG. 3B illustrates separated components of a depletion device having more than one liquid chamber. FIG. 3C illustrates an exemplary depletion device having more than one liquid chamber.

FIGS. 4A-C illustrate an exemplary single liquid chamber depletion device with a rigid internal liquid chamber and flexible external enclosure. FIG. 4A illustrates a cross-sectional view and a magnified view of a cross-section of a single liquid chamber depletion device. FIG. 4B illustrates separated components of a single liquid chamber depletion device. FIG. 4C illustrates an exemplary single liquid chamber depletion device.

FIGS. 5A-C illustrate an exemplary single liquid chamber depletion device having a flexible enclosure, flexible liquid chamber, and a flexible depletion chamber according to the present disclosure. FIG. 5A illustrates a cross-sectional view of a single liquid chamber depletion device having a flexible enclosure, flexible liquid chamber, and a flexible depletion chamber according to the present disclosure. FIG. 5B illustrates separated components of a single liquid chamber depletion device having a flexible enclosure, flexible liquid chamber, and a flexible depletion chamber. FIG. 5C illustrates an exemplary single liquid chamber depletion device.

FIG. 6A illustrates a cross-sectional view of a single liquid chamber depletion device. FIG. 6B illustrates separated components of a single liquid chamber depletion device. FIG. 6C illustrates a single liquid chamber depletions device.

FIGS. 7A-C illustrate an exemplary multi chamber depletion device having a flexible enclosure, two flexible liquid chambers, and three flexible depletion chambers according to the present disclosure. FIG. 7A illustrates a cross-sectional view of a multi chamber depletion device having a flexible enclosure, two flexible liquid chambers, and three flexible depletion chambers according to the present disclosure. FIG. 7B illustrates separated components of a multi chamber depletion device. FIG. 7C illustrates a multi chamber depletion device.

FIGS. 8A-C illustrate an exemplary single chamber depletion device having a single liquid chamber and two gas depletion chambers according to the present disclosure. FIG. 8A illustrates a cross-sectional view of a single chamber depletion device having a single liquid chamber and two gas depletion chambers. FIG. 8B illustrates separated components of a single chamber depletion device. FIG. 8C illustrates a single chamber depletion device.

FIG. 9A illustrates a cross-sectional view of a multi chamber depletion device. FIG. 9B illustrates separated components of a multi chamber depletion device. FIG. 9C illustrates a multi chamber depletion device.

FIGS. 10A-C illustrate an exemplary multi chamber depletion device having two liquid chambers in a parallel configuration and three gas depletion chambers according to the present disclosure. FIG. 10A illustrates a cross-sectional view of a multi chamber depletion device according to the present disclosure. FIG. 10B illustrates separated components of a multi chamber depletion device. FIG. 10C illustrates a multi chamber depletion device.

FIG. 11A illustrates an exemplary geometry of gas flow control features. FIG. 11B illustrates an exemplary geometry of gas flow control features. FIG. 11C illustrates an exemplary geometry of gas flow control features.

FIGS. 12A-D illustrate an exemplary single chamber depletion and plasma separation device having a single liquid chamber, single depletion chamber and a single plasma chamber according to the present disclosure. FIG. 12A illustrates a cross-sectional view of a single chamber depletion and plasma separation device. FIG. 12B illustrates a magnified view of a cross-section of a single chamber depletion and plasma separation device. FIG. 12C illustrates separated components of a single chamber depletion and plasma separation device. FIG. 12D illustrates an exemplary single chamber depletion and plasma separation device.

FIGS. 13A-C illustrate an exemplary depletion and plasma separation device having a single liquid chamber, two depletion chambers and a plasma chamber according to the present disclosure. FIG. 13A illustrates a cross-sectional view of a depletion and plasma separation device according to the present disclosure. FIG. 13B illustrates separated components of a depletion and plasma separation device. FIG. 13C illustrates a depletion and plasma separation device.

FIG. 14A illustrates a cross-sectional view of a depletion device. FIG. 14B illustrates separated components of a depletion device. FIG. 14C illustrates a depletion device.

FIG. 15A illustrates a cross-sectional view of a depletion device. FIG. 15B illustrates separated components of a depletion device. FIG. 15C illustrates a depletion device.

FIGS. 16A-C illustrate an exemplary re-oxygenation device having a single fluid chamber and two oxygenation chambers according to the present disclosure. FIG. 16A illustrates a cross-sectional view and magnified cross-sectional view of a re-oxygenation device. FIG. 16B illustrates separated components of a re-oxygenation device. FIG. 16C illustrates a re-oxygenation device.

DETAILED DESCRIPTION OF THE INVENTION

Figure 1B:
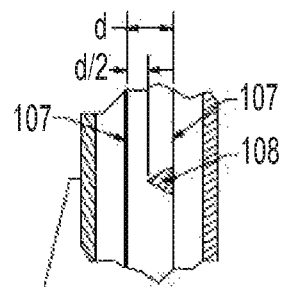
FIGS. 1A-D illustrate an exemplary single liquid chamber depletion device according to the present disclosure.

The transfusion of red blood cells (RBCs) is a life-saving therapy aimed at improving oxygenation of the tissues and vital end organs in patients. A majority of RBC units used for transfusion are stored at 1-6° C. for up to 42 days in an oxygen-permeable polyvinylchloride blood bag that contains additive/preservative solution.

Blood Donor: Whole blood is preferably donated from a healthy individual or donor and held in a blood bank for later use to be ultimately used by a recipient. Subjects who are scheduled for surgery or other treatment may donate blood for themselves in a process known as autologous blood donation. Alternatively, blood is donated for use by another in a process known as heterologous transfusion. The collection of a whole blood sample drawn from a donor, or in the case of an autologous transfusion from a patient, may be accomplished by techniques known in the art, such as through donation or apheresis.

Whole Blood: Whole blood is a suspension of blood cells that contains red blood cells, white blood cells, platelets suspended in plasma, including electrolytes, hormones, vitamins, and antibodies.

Blood products: As used herein, "blood product" or "blood products" refers to, and includes, whole blood, red blood cells, plasma, leukocytes, and platelets. "Blood product" also refers to depleted blood products including packed red blood cells, leukocyte reduced red blood cells, platelet reduced red blood cells. Blood products further include blood products having one or more additive solutions including, but not limited to, anticoagulants, antioxidants, storage additives, and buffers. Depleted blood products, as used herein, refer to blood products depleted of $O_2$, $CO_2$ or both, particularly after treatment with, or passage through a device of the present disclosure. Reoxgenated blood products are depleted blood products that have had oxygen levels restored to in vivo levels, or higher, usually in preparation for transfusion.

Red Blood Cells (RBCs): As used herein, "red blood cells" (RBCs), "packed red blood cells" (pRBCs), and "red blood cell suspensions" refer to and include blood products having red blood cells or erythrocytes. Red blood cells further include red blood cell products having one or more additive solutions. Red blood cells as used herein, may be depleted or reduced of leukocytes and other non-erythrocytes. As used herein, red blood cells include compositions depleted of plasma (plasma reduced). Red blood cells, as used herein, may further include red blood cell products having reduced or depleted platelets.

White blood cells: White blood cells or leukocytes as used herein include granulocytes also known as polymorphonuclear leukocytes. Granulocytes include neutrophils, basophils, and eosinophils. White blood cells also include agranulocytes, also known as mononuclear leukocytes, and include monocytes, and macrophages. Blood products according the present disclosure include leukoreduced and leukodepleted blood.

Platelets: Platelets are small cellular components of blood that facilitate the clotting process by sticking to the lining of the blood vessels. The platelets like the red blood cells are made by the bone marrow and survive in the circulatory system for 9 to 10 days before they are removed by the spleen. Platelets are typically prepared using a centrifuge to separate the platelets from the plasma. Platelets, unlike RBCs, require $O_2$ for the generation of ATP.

Plasma: Plasma is a protein-salt solution and the liquid portion of the blood in which red and white blood cells and platelets are suspended. Plasma is 90% water and constitutes about 55 percent of the blood volume. One of the primary functions of plasma is to assist in blood clotting and immunity. Plasma is obtained by separating the liquid portion of the blood from the cells. Typically, plasma is separated from the cells by centrifugation. Centrifugation is the process used to separate the components of the whole blood into the plasma, the white blood cells, the platelets and the packed red blood cells. During centrifugation, the plasma will initially migrate to the top of a vessel during a light spin. The plasma is then removed from the vessel. The white blood cells and platelets are removed during a second centrifugation cycle to produce the packed red blood cells.

As used herein and in the appended claims, the singular forms "a," "an," and "the" include plural references unless the content clearly dictates otherwise. Thus, for example, reference to "a sorbent" includes a plurality of such sorbents and equivalents thereof known to those skilled in the art, and so forth, and reference to "the sorbent" is a reference to one or more such sorbents and equivalents thereof known to those skilled in the art, and so forth.

Human red blood cells in vivo are in a dynamic state. In whole blood, white blood cells are normally present in the range between 4,300 and 10,800 cells/µL and the normal RBC range at sea level is 5.4 million/µL (+0.8) for men and 4.8 million µL (+0.6) for women. The red blood cells contain hemoglobin, the iron-containing protein that carries oxygen throughout the body and gives red blood its color. The percentage of blood volume composed of red blood cells is called the hematocrit. Packed red blood cells are prepared from whole blood using centrifugation techniques commonly known in the art. The packed red blood cells are the blood component that will be stored in the unique storage system of this invention for later transfusion.

The normal life span of a red blood cell (RBC) is 120 days. Approximately 0.875% of the RBCs are retired every 24 hours by the spleen and new RBCs are made by the bone marrow. Consequently, when blood is drawn from a donor, there are a percentage of white blood cells and a spectrum of cells of different ages.

The main function of RBCs is to exchange oxygen and carbon dioxide at lung and tissues, and unlike other cells in body, it does not rely on oxygen in oxidative phosphorylation but entirely on glycolysis for ATP production. ATP is critical for viability of RBCs and, together with 2,3-DPG, their free cytosolic concentrations are tightly regulated by their function on feedback inhibition to key enzymes in glycolytic pathway. Under refrigerated storage condition, dis-inhibition of glycolytic pathway is desirable to overcome the gradual depletion of ATP and 2,3-DPG over several weeks of storage. Hemoglobin concentration in RBCs is similar to 2,3-DPG and ATP, and its deoxygenated state has a binding pocked with high affinities for 2,3-DPG and ATP compared to oxy-hemoglobin. Thus, stripping this oxygen to few % occupancy (~60% occupied when collected and processed) will cause uptake of 2,3-DPG and ATP, resulting in reduced concentration of free molecules, stimulating glycolytic flux. In a healthy individual, the percent saturation of hemoglobin in RBCs ($sO_2$) in the lungs is 100%. As the RBCs circulate through the body, $O_2$ is released and the $sO_2$ can reach less than 10% $sO_2$ in hypoxic tissues.

As used herein, a liquid may be provided to a device of the present disclosure either by gravity flow or by a pump, including but not limited to a peristaltic pump. The flow rate may be controlled by adjusting the head height in the case of a gravity driven flow, change in pump velocity or by restricting the flow. It is understood that blood products, particularly cellular components of blood products may be damaged by high pressures or high velocity liquid flows. Accordingly, flows are controlled to minimize or eliminate cellular damage. In an aspect, the pressure drop of a liquid flowing through the device should not exceed 2 lbs/in². In another aspect, the pressure drop of a liquid flowing through the device should not exceed 1.5 lbs/in². In another aspect, the pressure drop of a liquid flowing through the device should not exceed 1.0 lbs/in².

Figure 1A:
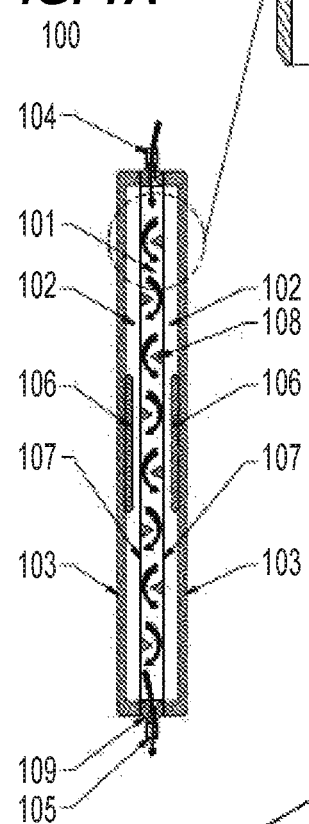
Figure 1C:
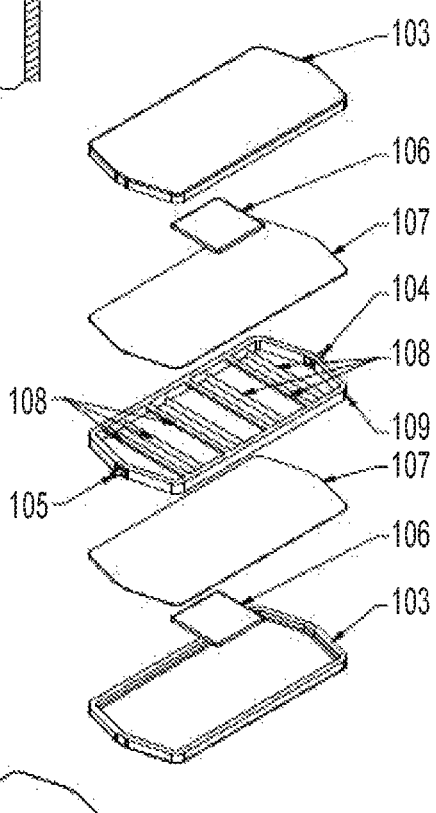

The present disclosure provides for and includes a depletion device for removing a gas from a liquid comprising an enclosure. In certain embodiments according the present disclosure, the enclosure may be a rigid enclosure as shown for example in FIGS. 1A-D, 2A-C, 5A-C, and 6A-C. Referring to FIGS. 1A-C, a rigid enclosure according to the present disclosure may be prepared from an outer shell 103 and may include inner shell 109 which may further incorporate flow control features 108. In certain embodiments, two outer shells 103 and inner shell 109 may be joined using any suitable manner known in the art including adhesive and bonding materials, e.g., glues, epoxies, bonding agents, and adhesives such as loctite 409 or other suitable super glue, welding and bonding processing, e.g., ultrasonic or thermosonic bonding, thermal bonding, diffusion bonding, or press-fit, etc.

Referring to FIGS. 3A-C, a rigid enclosure may include two outer shells 103, one or more inner shells 109 and one or more enclosure shells 110 to form two or more liquid chambers 101 and two or more depletion chambers 102 where liquid chambers 101 and depletion chambers 102 are separated from, and formed by gas permeable barriers 107. In certain embodiments, liquid chambers 101 and depletion chambers 102 may be separated from, and formed by gas impermeable to prepare divided and isolated liquid chambers 101 and depletion chambers 102. Enclosures comprising two outer shells 103, one or more inner shells 109, gas permeable barriers 107 and one or more gas impermeable barriers may be joined in any known manner as provided above including adhesives, glues, epoxies, bonding agents, welding, ultrasonic or thermosonic bonding, or thermal bonding.

In another embodiment, the enclosure may be a flexible material divided into one or more liquid chambers, one or more depletion chambers, and combinations thereof. In some embodiments, the enclosure may be a flexible bag enclosing one or more liquid chambers or one or more depletion chambers that are rigid, and combinations thereof. In some embodiments according to the present disclosure, an enclosure may be gas impermeable, gas permeable, or gas permeable and coated with a gas impermeable barrier or film. In other embodiments, the flexible material may be formed into a bag. In some embodiments, the flexible material may also be elastic.

According to the present disclosure, a flexible enclosure may be an enclosure that is capable of being bent or flexed. A flexible enclosure may be pliant, pliable, flexile, or elastic. A flexible enclosure may expand either through a change in shape due to flexibility or through an elastic expansion to contain a total volume. A flexible enclosure expands and contains a volume under ambient pressure. An elastic enclosure expands when the internal pressure of the enclosure is greater than the ambient pressure. According to the present disclosure, the ambient pressure corresponds to atmospheric pressure (typically 760 Torr) without consideration to changes in pressure due to weather or altitude.

The volume of a flexible enclosure may be described by the following equation $$V_t = V_v + V_l + V_d + V_c$$

where $V_t$ is the total expanded volume, whether by elastic or inelastic expansion, $V_v$ is the initial volume comprising a void volume, $V_l$ is the volume of liquid contained in one or more liquid chambers, $V_d$ is the volume contained in one or more gas depletion chambers 115 or depletion chamber 102 when the depletion device is fully expanded, and $V_c$ is the volume of the internal components of the bags including the unfilled gas depletion chambers 115 and unfilled liquid chambers 101. $V_c$ includes the volume of any depletion media 106 contained in a depletion device. An unused, unexpanded flexible bag of the current disclosure would have an initial volume $V_i = V_v + V_c$.

In an embodiment of the present disclosure, $V_l$ equals the volume of a standard unit of blood. In another embodiment, $V_l$ equals about 500 mls. In a further embodiment, $V_l$ does not exceed 600 ml. In another embodiment, $V_l$ may be between 100 and 550 ml. In a further embodiment the volume $V_l$ may be 300 to 500 ml or 300 to 550 ml.

In embodiments according to the present disclosure, the flexible enclosure further includes features to prevent the plastic from sticking together. In an embodiment, the feature may be textured to prevent the plastic from sticking together. In embodiments according the present disclosure, a texture may be ridges, bumps, threads, strands or other features to make the surface of the enclosure rough. In an embodiment, the textured surface may be on the inside of the enclosure. In an embodiment, the textured surface contacts the liquid.

In certain embodiments, an flexible enclosure may enclose an initial volume ($V_v$) corresponding to the unexpanded enclosure volume which may also be termed a dead or void volume. A void volume $V_v$ may be minimized by applying a vacuum to remove any air present during manufacture to provide a decreased initial volume $V_i$. In other embodiments, the air present during manufacture may be flushed with a flushing gas before applying a vacuum to minimize $V_v$. In some embodiments, a flushing gas may be used to replace the air present during the manufacturing process. Several gases suitable for a flushing gas include, but are not limited to, argon, helium, and nitrogen. A flushing gas may be used to decrease the amounts of oxygen, carbon dioxide, or both in the depletion device. In an embodiment, the flushing gas has a partial pressure of oxygen of less than 1 Torr. In another embodiment, the flushing gas has a partial pressure of oxygen and carbon dioxide of less than 1 Torr.

In embodiments according the present disclosure, a volume contained by a flexible depletion device may increase to a total volume ($V_t$) as a liquid for depletion is provided through at least one liquid inlet 104. A flexible depletion device containing a liquid will have a liquid volume $V_l$. In some embodiments, the liquid volume may displace any air or flushing gas present so that $V_v$=zero. In some embodiments, the total volume ($V_t$) may include a volume corresponding to the volume of a depletion gas ($V_d$) provided through at least one gas inlet 111. In embodiments of a depletion device having a depletion media 106, $V_d$ will be near zero as the volume of the depletion media is included in $V_c$. In another embodiment, the volume of the depletion media will be less that 50 cm$^3$.

According the present disclosure, a flexible enclosure may be able to adjust in volume as a liquid or a gas is provided through at least one gas inlet 111. Liquid or gas that does not immediately exit through at least one liquid outlet 105 or at least one gas outlet 112 may accumulate in a flexible enclosure causing an increase in contained volume of a flexible enclosure by $V_d$. In embodiments according the present disclosure, the flow rate of a gas through gas inlet 111 and gas outlet 112 is less than 20 liters per hour. In other embodiments, the maximum gas flow rate is less than 18 liters per hour. In yet another embodiment, the flow rate is less than 15 liters per hour. In further embodiments, the flow rate of a gas through gas inlet 111 and gas outlet 112 is less than 10 liters per hour or less than 5 liters per hour.

Referring to FIGS. 4A-C, a depletion device 400 according to the present disclosure may be prepared from both flexible and rigid materials. In an embodiment, the enclosure of a depletion device may be prepared from a flexible shell 129 and a rigid inner shell 109 having flow control features 108. Flexible shell 129 may be prepared from a gas impermeable material or coated with a gas impermeable material.

In certain embodiments, flexible shell 129 may also be expandable. In some embodiments, a flexible shell 129 may be expandable and elastic. In other embodiments, flexible shell 129 may be a laminated material that is gas impermeable. In certain embodiments, the combination of flexible shell 129 and one or more inner shells 109 provide for a gas impermeable enclosure. In certain embodiments, an enclosure may have a flexible shell 129 combined with a outer shell 103 and one or more inner shells 109.

As illustrated in FIGS. 5A-C, 6A-C, and 7A-C, enclosures according the present disclosure may be prepared as a flexible or expandable enclosure. Referring to FIGS. 5A-C, the enclosure of device 500 may formed of two gas barrier film flexible shells 129 separated from an inner liquid chamber by two gas permeable barriers 107 to prepare a single liquid chamber 101.

Figure 6A:
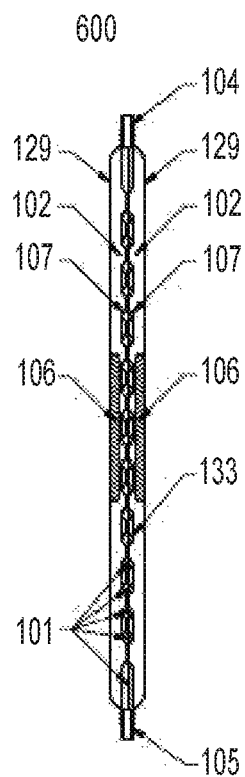
FIGS. 6A-C illustrate an exemplary single liquid chamber depletion device having a flexible enclosure, a flexible liquid chamber with an indirect liquid path, and two flexible depletion chambers.
Figure 6B:
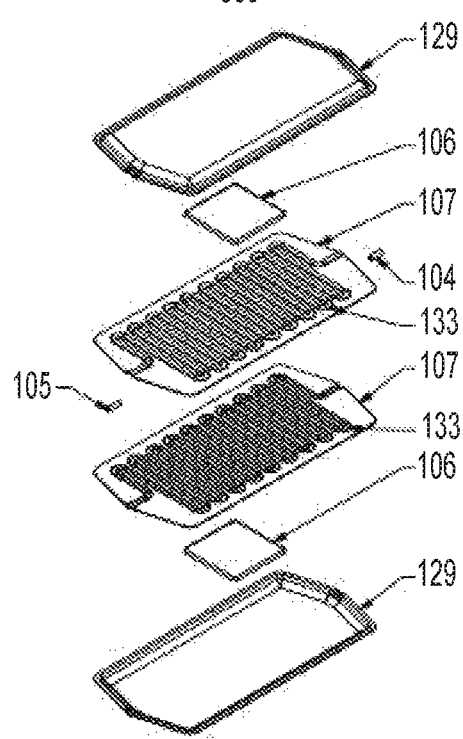
Figure 6C:

Referring to FIGS. 6A-C, a device 600 may include a flexible shell 129 housing a liquid chamber 101 formed from two gas permeable barriers 107. As illustrated in FIGS. 6A-C, the two gas permeable barriers 107 may be joined together to prepare a liquid chamber 101 having an indirect path 133. As shown in exemplary device 600, the liquid chamber 101 may have a zig-zag path for liquid flow to provide for mixing, thickness control, and flow control. In other embodiments, liquid path 133 of liquid chamber 101 may be bifurcated and rejoined one or more times. In some embodiments, liquid path 133 may be divided into three or more paths that are rejoined prior to liquid outlet 105. In some embodiments, liquid path 133 may be divided into four or more paths that are rejoined prior to liquid outlet 105. In some embodiments, liquid path 133 may be divided into five or more paths that are rejoined prior to liquid outlet 105. In other embodiments, liquid path 133 may have 6, 7, 8, 9, 10, or more branches that rejoin prior to liquid outlet 105. The liquid path 133 of device 600 may increase the path length traveled by the liquid and may increase the residence time of the fluid flowing in liquid chamber 101. A liquid path 133 may provide for increased mixing of the liquid and increase the exposure of the liquid to the gas permeable barrier 107 and an adjacent depletion chamber 102. Depletion chambers 102 may include depletion media 106.

In an embodiment, liquid path 133 may have a cross-sectional shape selected from the group consisting of rectangular, circular, and irregular shape. In certain embodiments, liquid path 133 may have more than one cross-sectional shape along its longitudinal path, selected from one or more of the group consisting of rectangular, circular, and irregular shape. In an embodiment, liquid path 133 may have a uniform cross-sectional area along its longitudinal path. In certain embodiments, liquid path 133 may have a changing cross-sectional area along its longitudinal path.

In some embodiments, a rectangular cross-section of liquid path 133 may have a depth of 0.01 mm or more. In an embodiment, a rectangular cross-section of liquid path 133 may have a depth of 0.1 mm or more. In an embodiment, a rectangular cross-section of liquid path 133 may have a depth of 0.2 mm or more. In an embodiment, a rectangular cross-section of liquid path 133 may have a depth of 0.3 mm or more. In an embodiment, a rectangular cross-section of liquid path 133 may have a depth of 0.4 mm or more. In an embodiment, a rectangular cross-section of liquid path 133 may have a depth of 0.5 mm or more. In other embodiments, a rectangular cross-section of liquid path 133 may have a depth of up to 0.6 mm. In another embodiment, a rectangular cross-section of liquid path 133 may have a depth of up to 0.7 mm. In yet other embodiments, a rectangular cross-section of liquid path 133 may have a depth of up to 0.8 mm, 0.9 mm, or 1.0 mm. In other embodiments, a rectangular cross-section of liquid path 133 may have a depth of between 1.0 and 2.0 mm. In other embodiments, a rectangular cross-section of liquid path 133 may have a depth of between 1.5 and 2.0 mm. In other embodiments, a rectangular cross-section of liquid path 133 may have a depth of between 1.75 and 2.0 mm. In certain other embodiments, a rectangular cross-section of liquid path 133 may have a depth of between 2.0 mm and 3.0 mm. In certain embodiments, a rectangular cross-section of liquid path 133 may have a depth of between 2.5 mm and 3.0 mm. In some embodiments, the rectangular cross-section of liquid path 133 may vary and have one or more depths.

In some embodiments, liquid path 133 may be a micro channel. In some embodiments, a circular cross-section of liquid path 133 may have a diameter of between 100 µm and 500 µm. In some embodiments a circular cross-section of liquid path 133 may have a diameter of 100 µm or more. In some embodiments a circular cross-section of liquid path 133 may have a diameter of 150 µm, or more. In some embodiments a circular cross-section of liquid path 133 may have a diameter of 200 µm. In some embodiments a circular cross-section of liquid path 133 may have a diameter of 250 µm. In some embodiments a circular cross-section of liquid path 133 may have a diameter of 300 µm. In some embodiments a circular cross-section of liquid path 133 may have a diameter of 350 µm. In some embodiments a circular cross-section of liquid path 133 may have a diameter of 400 µm. In yet other embodiments a circular cross-section of liquid path 133 may have a diameter of 450 µm or 500 µm.

In some embodiments, an irregular cross-section of liquid path 133 may have an area in the range of 0.01 to 10 mm$^2$. In an embodiment, an irregular cross-section of liquid path 133 may have an area in the range of 0.01 to 0.1 mm$^2$. In an embodiment, an irregular cross-section of liquid path 133 may have an area in the range of 0.1 to 1 mm$^2$. In an embodiment, an irregular cross-section of liquid path 133 may have an area in the range of 1 to 5 mm$^2$. In an embodiment, an irregular cross-section of liquid path 133 may have an area in the range of 5 to 10 mm$^2$.

According to the present disclosure, liquid path 133 may have longitudinal paths selected from the group consisting of meandering, sinuous, undulating, sinusoidal, spiral, partially spiral, and zig-zag. In an embodiment, the path length of a liquid path 133 may be at least 10 fold or more of the length of flexible shell 129. In another embodiment, the path length of a liquid path 133 may be at least 15 fold or more of the length of flexible shell 129. In another embodiment, the path length of a liquid path 133 may be at least 20 fold or more of the length of flexible shell 129. In another embodiment, the path length of a liquid path 133 may be at least 30 fold or more of the length of flexible shell 129. In another embodiment, the path length of a liquid path 133 may be at least 40 fold or more of the length of flexible shell 129. In another embodiment, the path length of a liquid path 133 may be at least 50 fold or more of the length of flexible shell 129.

Referring to FIGS. 7A-C, a flexible or expandable enclosure may be formed of two flexible shells 129 separated from and inner liquid chamber by two gas permeable barriers 107 and further divided into chambers by additional gas permeable barriers 107. As illustrated in FIG. 7B, two flexible shells 129 separated by four gas permeable barriers 107 may result in two liquid chambers 101 and three depletion chambers 102. In certain embodiments according to the present disclosure, the addition of a further gas permeable barrier 107 results in the formation of one added liquid chamber 101 and one added depletion chamber 102. According to the present disclosure, a depletion device may include three depletion chambers and two liquid chambers. In an embodiment, a depletion device may include four depletion chambers and three liquid chambers. In an embodiment, a depletion device may include five depletion chambers and four liquid chambers. In other embodiments, a depletion device may include six depletion chambers and five liquid chambers.

In embodiments according to the present disclosure, a flexible shell 129 (e.g., a flexible shell 129, which can also be expandable), may be prepared from a gas impermeable plastic. In an embodiment, the gas impermeable plastic may be a laminate. In certain embodiments, the laminate may be a transparent barrier film, for example a nylon polymer. In an embodiment, the laminate may be a polyester film. In an embodiment, the laminate may be Mylar®. In certain embodiments, the laminate may be a metalized film. In an embodiment, the metalized film may be coated with aluminum. In another embodiment, the coating may be aluminum oxide.

Flexible shell 129 according to the present disclosure may be joined in any known manner including fixing by adhesive or otherwise bonding using any suitable manner known in the art including adhesive and bonding materials, e.g., glues, epoxies, bonding agents, and adhesives such as loctite 409 or other suitable super glue, welding and bonding processing, e.g., ultrasonic or thermosonic bonding, thermal bonding, diffusion bonding, or press-fit, etc.

In certain embodiments, an enclosure may have both flexible and rigid aspects where the flexible aspect provides for expansion to accommodate the liquid flowing through one or more chambers. In some embodiments, an enclosure may include a combination of rigid outer shells 103, flexible shells 129, inner shells 109, enclosure shells 110, and gas permeable barriers 107 thereby providing a bag or container that expands as a liquid flows through the enclosure, liquid chambers and depletion chambers.

An enclosure according the present disclosure may be formed of one or more parts prepared from a gas impermeable material including a plastic or other durable lightweight material. In some embodiments, an enclosure may be formed of more than one material. In an embodiment, an enclosure may be formed of a material and coated with a gas impermeable material to prepare a gas impermeable enclosure. In an embodiment, a rigid or flexible enclosure may be prepared from a plastic that may be injection molded. In embodiments according the instant disclosure, the plastic may be selected from polystyrene, polyvinyl chloride, or nylon. In an embodiment, enclosure materials may be selected from the group consisting of polyester (PES), polyethylene terephthalate (PET), polyethylene (PE), high-density polyethylene (HDPE), polyvinyl chloride (PVC), polyvinylidene chloride (PVDC), low-density polyethylene (LDPE), polypropylene (PP), polystyrene (PS), high impact polystyrene (HIPS), polyamides (PA) (e.g., nylon), acrylonitrile butadiene styrene (ABS), polycarbonate (PC), polycarbonate/acrylonitrile butadiene styrene (PC/ABS), polyurethanes (PU), melamine formaldehyde (MF), plastarch material, phenolics (PF), polyetheretherketone (PEEK), polyetherimide (PEI) (Ultem), polylactic acid (PLA), polymethyl methacrylate (PMMA), polytetrafluoroethylene (PTFE), and urea-formaldehyde. In certain embodiments, the enclosure may be polyethylene. In some embodiments, the polyethylene enclosure may comprise one or more polyethylene components that are welded together.

The present disclosure further provides for and includes a depletion device having one or more liquid chambers or cavities. In some embodiments, a liquid chamber may be a rigid chamber or cavity as provided above. In other embodiments, a liquid chamber may be a flexible chamber or cavity as provided above. In an embodiment, one or more liquid chambers may be a chamber, cavity or space through which a liquid flowing through the depletion device may flow. In embodiments according the present disclosure, one or more liquid chambers may be in liquid communication with each other and in liquid communication with at least one liquid inlet and at least one liquid outlet.

As illustrated in FIGS. 1A-D, a rigid liquid chamber 101 may be formed by a combination of an inner shell 109 and two gas permeable barriers 107. Similarly, as illustrated in FIGS. 3A-C, 9A-C and 10A-C, embodiments of depletion devices of the present disclosure may have two or more rigid liquid chambers 101 formed by a combination of two or more outer inner shells 109 each combined with two gas permeable barriers 107. In other embodiments, for example as illustrated in FIGS. 5A-C, 6A-C, and 7A-C, a liquid chamber 101 may be formed by a combination of two flexible gas permeable barriers 107. In certain embodiments according the present disclosure, the outer enclosure is 5 inches×8 inches. In certain embodiments, the gas permeable barrier is between 35 to 175 µm thick.

In certain embodiments according to the present disclosure, a liquid chamber 101 may further comprise flow control features 108 as provided below to direct the flow of liquid and provide for mixing of a liquid flowing through the liquid chambers by, for example, disrupting laminar flow of the liquid. In other embodiments, a liquid chamber 101 may include flow control features that provide for an indirect path 133. Though not limited by theory, mixing of the liquid in the liquid chambers may ensure efficient diffusion and depletion of oxygen and carbon dioxide gases to the depletion chambers.

Similarly, in certain embodiments including a flexible enclosure, in whole or in part, gas permeable barriers 107 forming liquid chamber 101 may further include flow control features to direct the flow of liquid and to provide for mixing by, for example, disrupting laminar flow of the liquid. As illustrated in FIGS. 5A-C and 7A-C, liquid chamber 101 is depicted without flow control features. As illustrated in FIG. 6A-C, liquid chamber 101 includes an indirect path 133 that provides flow control features. Flow control features may be formed, for example, by bonding the gas permeable barriers 107 together in a manner that would direct the flow of blood along a controlled path or indirect path 133, in the gas permeable barriers 107. This directed flow would both mix and minimize the distance between individual red cells and the gas permeable barriers 107. The number and position of flow control features may also be altered to optimize the process for specific configuration. In an embodiment according the present disclosure, gas permeable barriers 107 may include ridges that are oriented perpendicular to the flow of the liquid. In other embodiments, gas permeable barriers 107 may include ridges oriented at an angle relative to the flow of liquid. Flow control features according the present enclosure are provided in greater detail below.

As illustrated in FIGS. 12A-C and 13A-C, a liquid chamber 101 may provide for the depletion of plasma from a liquid flowing in the liquid chamber 101. As illustrated in FIGS. 12A-C, one of the gas permeable barriers 107 may be replaced with a plasma porous hydrophilic membrane 124 which is capable of retaining red blood cells and allowing for the passage of anaerobic plasma through the hydrophilic membrane 124 and into plasma chamber 117. Anaerobic plasma may then flow from plasma chamber 117 out through anaerobic plasma port 116. As illustrated in FIGS. 13A-C, a second depletion chamber 122 may be included in a combined plasma and gas depletion device. As shown in FIGS. 13A-C, depletion chamber 122 is separated from plasma chamber 117 by a gas permeable barrier 107. Additional configurations of gas permeable barriers 107, plasma porous hydrophilic membrane 124, plasma outer shell 119, outer shell 103, and other described components can provide for additional depletion chambers 102 or 122, additional plasma chambers 117, and additional liquid chambers 101. It should be understood that such additional chambers may be arranged in series or parallel with the appropriate connections.

In accordance with the present disclosure, the surfaces of a liquid chamber 101 in contact with the liquid can be a biocompatible material. Similarly, other surfaces and components of the gas depletion device in liquid communication with the liquid are prepared from biocompatible materials. In an embodiment, a biocompatible material is a compatible blood product of the present disclosure. Biocompatible materials of the present disclosure include those defined and provided in International Standard ISO 10993.

The present disclosure further provides for and includes depletion devices having one or more depletion chambers or cavities. In certain embodiments according to the present disclosure, depletion chamber 102 has lower concentrations or partial pressures of a gas than the concentration or partial pressure of a gas present in liquid chamber 101 separated from the depletion chamber 102 by a gas permeable barrier 107. Accordingly, a gas flows from a liquid chamber 101 having a higher concentration to a depletion chamber 102, thus depleting the liquid in liquid chamber 101 of a gas. In certain embodiments, a depletion device may have two depletion chambers. In some embodiments, a depletion device may have three depletion chambers. In other embodiments, a depletion device may have four depletion chambers. In further embodiments, a depletion device may have five or six depletion chambers. In yet further embodiments, a depletion device may have seven, eight or more depletion chambers.

In embodiments according to the present disclosure, a depletion device may have from two to five, two to seven, two to nine, or two to eleven depletion chambers. In other embodiments, a depletion device may have from three to six, three to eight, three to ten, or three to twelve depletion chambers. In other embodiments, the number of depletion chambers may be up to 10, up to 12, up to 14, up to 16, or more than 16 depletion chambers.

In embodiments according the present disclosure, a gas having a lower concentration or partial pressure in depletion chamber 102 than in liquid chamber 101 may be oxygen. Depletion chamber 102 having a lower concentration or partial pressure of oxygen is an oxygen depletion chamber 102. In certain embodiments, an oxygen depletion chamber 102 may contain little or no oxygen. In another embodiment, an oxygen depletion chamber 102 may have a partial pressure of oxygen of less than 1 mmHg (less than 1 Torr) prior to use as a depletion device. In another embodiment, an oxygen depletion chamber 102 may have a partial pressure of oxygen of less than 0.1 mmHg prior to use as a depletion device. In a further embodiment, an oxygen depletion chamber 102 may have a partial pressure of oxygen of less than 0.05 mmHg prior to use as a depletion device. In yet another embodiment, an oxygen depletion chamber 102 may have a partial pressure of oxygen of less than 0.08 mmHg prior to use as a depletion device. In embodiments according to the present disclosure, an oxygen depletion chamber 102 may have a partial pressure of oxygen of between 0.01 mmHg and 0.1 mmHg prior to use as a depletion device. In an embodiment, an oxygen depletion chamber 102 may have a partial pressure of oxygen of between 0.05 mmHg and 0.5 mmHg prior to use as a depletion device.

In embodiments according the present disclosure, depletion chamber 102 may have a lower concentration or partial pressure of oxygen and carbon dioxide than compared to a liquid in liquid chamber 102. A depletion chamber 102 having a lower concentration or partial pressure of oxygen and carbon dioxide is an oxygen and carbon dioxide depletion chamber 102. In certain embodiments, an oxygen and carbon dioxide depletion chamber 102 may contain little or no oxygen and carbon dioxide prior to use as a depletion device. In other embodiments, an oxygen and carbon dioxide depletion chamber 102 may have a partial pressure of oxygen and carbon dioxide of less than 1 mmHg each (less than 1 Torr) prior to use as a depletion device. In another embodiment, an oxygen and carbon dioxide depletion chamber 102 may have a partial pressure of oxygen and carbon dioxide of less than 0.1 mmHg each prior to use as a depletion device. In a further embodiment, an oxygen and carbon dioxide depletion chamber 102 may have a partial pressure of oxygen and carbon dioxide of less than 0.05 mmHg each prior to use as a depletion device. In yet another embodiment, an oxygen and carbon dioxide depletion chamber 102 may have a partial pressure of oxygen and carbon dioxide of less than 0.08 mmHg each prior to use as a depletion device. In embodiments according to the present disclosure, an oxygen and carbon dioxide depletion chamber 102 may have a partial pressure of oxygen and carbon dioxide of between 0.01 mmHg and 0.1 mmHg each prior to use as a depletion device. In an embodiment, an oxygen and carbon dioxide depletion chamber 102 may have a partial pressure of oxygen and carbon dioxide of between 0.05 mmHg and 0.5 mmHg each prior to use as a depletion device.

In embodiments according the present disclosure, a gas having a lower concentration or partial pressure in depletion chamber 102 than in liquid chamber 101 may be carbon dioxide. Depletion chamber 102 having a lower concentration or partial pressure of carbon dioxide is a carbon dioxide depletion chamber 102. In certain embodiments, a carbon dioxide depletion chamber 102 may contain little or no carbon dioxide. In another embodiment, a carbon dioxide depletion chamber 102 may have a partial pressure of carbon dioxide of less than 1 mmHg (less than 1 Torr) prior to use as a depletion device. In another embodiment, a carbon dioxide depletion chamber 102 may have a partial pressure of carbon dioxide of less than 0.1 mmHg prior to use as a depletion device. In a further embodiment, a carbon dioxide depletion chamber 102 may have a partial pressure of carbon dioxide of less than 0.05 mmHg prior to use as a depletion device. In yet another embodiment, a carbon dioxide depletion chamber 102 may have a partial pressure of carbon dioxide of less than 0.08 mmHg prior to use as a depletion device. In embodiments according to the present disclosure, a carbon dioxide depletion chamber 102 may have a partial pressure of carbon dioxide of between 0.01 mmHg and 0.1 mmHg prior to use as a depletion device. In an embodiment, a carbon dioxide depletion chamber 102 may have a partial pressure of carbon dioxide of between 0.05 mmHg and 0.5 mmHg prior to use as a depletion device.

In embodiments according to the present disclosure, a lower concentration or partial pressure of a gas of depletion chamber 102 may be achieved by providing a depletion media 106. In an embodiment, a depletion media 106 may be an oxygen sorbent material. In another embodiment, a depletion media 106 may be a carbon dioxide sorbent material. In yet another embodiment, a depletion media 106 may be a combined oxygen and carbon dioxide sorbent material.

A depletion media 106 may be an oxygen sorbent material and an oxygen depletion media 106 is a depletion media 106 having an oxygen sorbent material. As used herein, "oxygen sorbent" is a material that irreversibly binds to or combines with oxygen under the conditions of use. As used herein, "oxygen sorbent" is a material capable of binding to, or combining with, oxygen irreversibly under the conditions of use. The term "oxygen scavenger" may be used interchangeably herein with "oxygen sorbent." In certain embodiments according to the present disclosure, a material may bind to or combine with oxygen irreversibly. In embodiments according to the present disclosure, a material binds oxygen with higher affinity than hemoglobin. In embodiments according to the present disclosure, $O_2$ depletion media may be materials that remove oxygen from RBCs or strip oxygen from the blood prior to storage. An oxygen scavenger can be used to remove the oxygen from the RBCs prior to storage in a blood bag. In other embodiments, oxygen may bind to a sorbent material and have a very slow rate of release, $k_{off}$. In an embodiment, the oxygen may chemically react with some component of the material and be converted into another compound. Any material where the off-rate of bound oxygen is less than the residence time of the blood can serve as an oxygen scavenger. In certain embodiments, a depletion media 106 may of an oxygen sorbent material that can deplete a unit of blood to less than 3% $sO_2$ in thirty minutes. A depletion media 106, of an oxygen sorbent material that can deplete 34 ml of blood to 3% $sO_2$ in two minutes. Oxygen sorbent materials may be formed into or incorporated in fibers, microspheres, gels and foams.

In embodiments according to the present disclosure, an oxygen depletion media 106 may be a mixture of non-toxic inorganic and/or organic salts and ferrous iron or other materials with high reactivity toward oxygen. In certain embodiments, an oxygen depletion media 106 may be made from particles that have significant absorbing capacity for $O_2$ (more than 5 ml $O_2$/g) and can maintain the inside of a depletion chamber 102 to less than 0.01%, which corresponds to $pO_2$ less than 0.08 mmHg. An oxygen depletion media 106 may be either free or contained in an oxygen permeable envelope as described below. A gas depletion device according the present disclosure can deplete approximately 100 mL of oxygen from a unit of blood.

Examples of oxygen scavengers include iron powders, for example ferrous ion containing powders, and organic compounds. For example, oxygen sorbents are provided by Multi sorb Technologies (Buffalo, N.Y.). Such materials can be blended to a desired ratio to achieve desired results. Non-limiting examples of oxygen scavengers include iron powders and organic compounds. Examples of $O_2$ sorbents include chelates of cobalt, iron, and Schiff bases. Additional non-limiting examples for $O_2$ sorbents may be found in Bulow et al., U.S. Pat. No. 7,347,887, issued Mar. 25, 2008, entitled "Oxygen sorbent compositions and methods of using same"; Ramprasad et al., U.S. Pat. No. 5,208,335, issued May 4, 1993, entitled "Reversible oxygen sorbent compositions"; and Sievers et al., U.S. Pat. No. 4,654,053, issued Mar. 31, 1987, entitled "Oxygen Sorbent," each of which is hereby incorporated by reference in its entirety.

In embodiments according to the present disclosure, a sorbent may be an oxidizable organic polymer having a polymeric backbone and a plurality of pendant groups. Examples of sorbents with a polymeric backbone include a saturated hydrocarbon (<0.01% carbon-carbon double bonds). In some embodiments, the backbone can contain monomers of ethylene or styrene. In an embodiment, a polymeric backbone may be ethylenic. In another embodiment, an oxidizable organic compound may be ethylene/vinyl cyclohexene copolymer (EVCH). Additional examples of substituted moieties and catalysts are provided in Yang et al., U.S. Patent Publication No. 2003/0183801, hereby incorporated by reference in its entirety. In additional embodiments, an oxidizable organic polymer can also comprise substituted hydrocarbon moieties. Examples of oxygen scavenging polymers include those described by Ching et al., International Patent Publication WO99/48963, hereby incorporated by reference in its entirety. Oxygen scavenging materials may include those provided in Ebner et al., U.S. Pat. No. 7,754,798, issued Jul. 13, 2010, entitled "Oxygen scavenger block copolymers and compositions"; Ebner et al., U.S. Pat. No. 7,452,601, issued Nov. 18, 2008, entitled "Oxygen scavenger compositions derived from isophthalic acid/or terephthalic acid monomer or derivatives thereof"; Ebner et al., U.S. Pat. No. 6,387,461, issued May 14, 2002, entitled "Oxygen scavenger compositions," each of which is hereby incorporated by reference in its entirety.

A depletion media 106 may be a carbon dioxide sorbent material and a carbon dioxide depletion media 106 is a depletion media 106 having a carbon dioxide sorbent material. As used herein, "carbon dioxide sorbent" is a material that irreversibly binds to or combines with carbon dioxide under the conditions of use. As used herein, "carbon dioxide sorbent" is a material capable of binding to or combining with carbon dioxide irreversibly under the conditions of use. The term "carbon dioxide scavenger" may be used interchangeably herein with "carbon dioxide sorbent." In certain embodiments according to the present disclosure, a material may bind to or combine with carbon dioxide irreversibly. In embodiments according to the present disclosure, a material binds carbon dioxide with higher affinity than hemoglobin. In other embodiments, a sorbent material may bind carbon dioxide with high affinity such that the carbonic acid present in the blood or RBC cytoplasm is released and absorbed by the sorbent.

In embodiments according to the present disclosure, carbon dioxide depletion media may be materials that remove carbon dioxide from RBCs or strip carbon dioxide from the blood prior to storage. A carbon dioxide scavenger can be used to remove the carbon dioxide from the RBCs prior to storage in a blood bag. In other embodiments, carbon dioxide may bind to a sorbent material and have a very slow rate of release, $k_{off}$. In an embodiment, the carbon dioxide may chemically react with some component of the material and be converted into another compound. Any material where the off-rate of bound carbon dioxide is less than the residence time of the blood can serve as a carbon dioxide scavenger. In certain embodiments, carbon dioxide depletion media 106 can deplete a unit of blood of carbon dioxide in 2 minutes. Carbon dioxide sorbent materials may be formed into or incorporated in fibers, microspheres, gels and foams.

Carbon dioxide scavengers include metal oxides and metal hydroxides. Metal oxides react with water to produce metal hydroxides. The metal hydroxide reacts with carbon dioxide to form water and a metal carbonate. In an embodiment, the carbon dioxide scavenger may be calcium oxide. For example, if calcium oxide is used, the calcium oxide will react with water that is added to the sorbent to produce calcium hydroxide.

$$CaO + H_2O \rightarrow Ca(OH)_2.$$

The calcium hydroxide will react with carbon dioxide to form calcium carbonate and water.

$$Ca(OH)_2 + CO_2 \rightarrow CaCO_3 + H_2O$$

In certain embodiments of the present disclosure, a depletion media 106 may combine both $O_2$ and $CO_2$ depletion or scavenging activity. A depletion media 106 may be an oxygen and carbon dioxide sorbent material or a mixture of an oxygen sorbent and a carbon dioxide sorbent. An oxygen and carbon dioxide depletion media 106 is a depletion media 106 having an oxygen and carbon dioxide sorbent material or a mixture of the two. As used herein, "oxygen and carbon dioxide sorbent" is a material that irreversibly binds to or combines with oxygen and carbon dioxide under the conditions of use. The term "oxygen and carbon dioxide scavenger" may be used interchangeably herein with "oxygen and carbon dioxide sorbent." In certain embodiments according to the present disclosure, a material may bind to or combine with oxygen and carbon dioxide irreversibly. In embodiments according to the present disclosure, a material binds oxygen and carbon dioxide with higher affinity than hemoglobin. In other embodiments, a sorbent material may bind oxygen and carbon dioxide with high affinity such that the carbonic acid present in the blood or RBC cytoplasm is released and absorbed by the sorbent.

Non-limiting examples of $CO_2$ scavengers include oxygen scavengers and carbon dioxide scavengers provided by Multisorb Technologies (Buffalo, N.Y.). Oxygen scavengers may exhibit a secondary functionality of carbon dioxide scavenging. In embodiments according to the present disclosure, $O_2$ depletion media and $CO_2$ depletion media may be blended to a desired ratio to achieve desired results.

In embodiments according to the present disclosure, depletion media 106 may be incorporated into, or provided to, a depletion chamber 102 in various forms. As used herein, depletion media 106 provides for, and includes, depletion media comprising oxygen sorbents, carbon dioxide sorbents and combined oxygen and carbon dioxide sorbents. It will be appreciated that sorbents can be incorporated into storage receptacles and bags in any known form, such as in sachets, patches, coatings, pockets, and packets.

According to some non-limiting embodiments of the present disclosure, storage receptacles for depletion media 106 may include small sachets, pockets, bags, receptacles or packets (each may be used interchangeably). The configurations of the packet and the chemistry contained in depletion media 106 may be different for each depletion chamber 102 to optimize performance. Referring to FIGS. 1A-D, 2A-C, 3A-C, and 4A-C, depletion media 106 may be provided to a depletion chamber 102 as one or more packets of a depletion media 106. In some embodiments, several packets of oxygen and carbon dioxide depletion media 106 could be placed in each depletion chamber 102, or a single longer, or larger, packet of oxygen and carbon dioxide depletion media 106 could be used. In other embodiments, oxygen depletion media 106 and carbon dioxide depletion media 106 could be included as separate packets. In certain embodiments having more than one depletion chamber 102, the configuration of the packet and the chemistry contained in the depletion media 106 could be different for each depletion chamber 102 to optimize performance. Similarly, in certain embodiments, one or more depletion chambers 102 may be configured to deplete $O_2$, and another one or more depletion chambers 102 may be configured to deplete $CO_2$.

In some embodiments, depletion media 106 may be contained within a gas permeable membrane, film or material. In certain embodiments, a small sachet or packet may be made of a silicone or siloxane material with high oxygen permeability. In some embodiments, the sachet or packet may be prepared from a biocompatible material. In an embodiment, a sachet or packet may have a wall thickness of less than 0.13 mm thickness to ensure that $O_2$ permeability ceases to become the rate-limiting step. In other embodiments, a sachet or packet may be made from materials such as 0.15 mm thick silicone membrane. In further embodiments, a sachet or packet for receiving a depletion media 106 may be made from materials such as PTFE or other fluoropolymer. Included and provide for in the present disclosure are sachets or packets that are prepared using the gas permeable membranes as provided below. In certain embodiments, the gas permeable membrane is an olefin fiber. In other embodiments, the gas permeable membrane is a flash-spun high-density polyethylene fiber.

In embodiments according to the present disclosure, sachets, pockets, bags, packets or receptacle for holding a depletion media 106 may be shaped or formed to increase the surface area. In an embodiment, a sachet or packet may be formed with a surface texture to increase the surface area. In other embodiments, a sachet may be a molded element with surface texture to increase the surface area. In an embodiment, a sachet or packet may have a comb-like geometry for rapid gas depletion. A sachet having a depletion media 106 may have a rectangular shape such as, for example, a 4"×6" rectangle, although other sizes are possible. In an embodiment, the depletion media may be in a sachet that is 6 cm×6 cm (e.g., 36 cm$^2$).

In embodiments according to the present disclosure, depletion media 106 may be prepared as a macroporous structure. In some embodiments, the macroporous structure may be a fibrous material, a foam or a microsphere. As used herein, a macroporous structure is a material or materials that is porous to particles of about 5 to 10 microns. A macroporous structure may be a weaved fiber, random fiber or a packed bed having layers, a packed bed having a heterogeneous mix of particles. Macroporous structures may include micro or macroparticles embedded or entrapped in a fibrous or foam structure. Macroporous structures may include micro or macroparticles contained in a sachet or packet as provided above. Macroporous structures of depletion media 106 may be incorporated into the sachets, packets and pockets as provided above.

Porous or micro-void structures also have increased surface areas available for reaction with oxygen or oxygen and carbon dioxide. In some embodiments, the surface area of the macroporous structure may be a fiber having a surface area capable of removing $O_2$, $CO_2$, or a combination thereof. In some embodiments the surface area may be at least $5 \times 10^3$ cm$^2$/g media. In an embodiment, the surface area may be from 10 cm$^2$ to 2000 cm$^2$. In another embodiment, the surface area may be from 20 cm$^2$ to 1000 cm$^2$. For fibers, the surface area may be determined based on the diameter of the fiber.

In an embodiment, a depletion media 106 may have a bulk density of from 0.01 g/cm$^3$ to 0.7 g/cm$^3$ and has an average distance between adjacent fibers of between 7 gm to 300 gm.

In an embodiment, the bulk density of a depletion media 106 may be from 0.001 g/cm$^3$ to 0.7 g/cm$^3$. In another embodiment, the bulk density of the depletion media 106 may be from 0.10 g/cm$^3$ to 0.5 g/cm$^3$. As used herein, the term "bulk density" means a numerical value expressed in g/cm$^3$ obtained by dividing the weight (in gram) of the mass of fibers by the volume (in cm$^3$) of the mass of fibers.

Removal of oxygen from a blood product involves a number of steps. Given the majority of the oxygen is bound to hemoglobin within the red blood cells, in order to remove the O$_2$, the oxygen needs to be released to the plasma. Oxygen in the plasma then has to diffuse to the surface of the depletion media 106 by passing through gas permeable barrier 107. At the depletion media 106 surface the oxygen can either react immediately with reactive groups on the surface, or dissolve in the polymer matrix (e.g., a fiber or microparticle). Once dissolved in the polymer matrix, O$_2$ can react with groups present within the polymer matrix.

In embodiments according to the present disclosure, depletion media 106 can be formed inside the pores of porous micro glass fibers. The encapsulation of transition-metal complexes within the pores of a porous material may be achieved by using a ship-in-a-bottle synthesis in which the final molecule is prepared inside the pores by reacting smaller precursors. After the synthesis, the large molecule may remain "mechanically entrapped" and encapsulated inside the pores with some restricted conformation and arrangement. A cobalt phthalocyanine/porous glass composite fiber for oxygen separation can be prepared by ship-in-a-bottle synthesis where encapsulation of cobalt phthalocyanine into pores of porous glass fibers is achieved by chemical vapor deposition using 1,2-dicyanobenzene. See, Kuraoka et al., "Ship-in-a-bottle synthesis of a cobalt phthalocyanine/porous glass composite membrane for oxygen separation," Journal of Membrane Science, 286(1-2):12-14 (2006), herein incorporated by reference in its entirety. In some embodiments, porous glass fibers may be manufactured as provided in Beaver et al., U.S. Pat. No. 4,748,121, issued May 31, 1988, entitled "Porous Glass Fibers with Immobilized Biochemically Active Material," herein incorporated by reference in its entirety. In another embodiment, a depletion media 106 can be formed as a porous sheet product using papermaking/non-woven wet-laid equipment. Sheets with O$_2$ scavenging formulations such as those described in Inoue, U.S. Pat. No. 4,769,175, issued Sep. 6, 1988, entitled "Sheet-like, Oxygen-Scavenging Agent," herein incorporated by reference in its entirety, can be formed and then encapsulated with a silicone film.

In embodiments according to the present disclosure, depletion media 106 may be encapsulated into microspheres. For example, silicones can form self-leveling, adhesive films. Silicone elastomers based on dimethyl silicone polymers that contain polar moieties (polyethylene oxide substituents, e.g., Dow Corning® 9011 Silicone Elastomer Blend) and low cross-link density make effective emulsifiers for preparing water-in-silicone emulsions. By modifying the water-in-silicone emulsion, depletion media 106 can be incorporated into aqueous emulsions of ultra-high molecular weight silicones (Dow Corning® HMW 2220 Non Ionic Emulsion). In certain embodiments, the addition of ethylene oxide or propylene oxide polymer chains can aid emulsification during formulation and improve compatibility with polar materials. In other embodiments, the depletion media 106 as microspheres may be incorporated into the sachets, packets and bags as provided above.

In embodiments according to the present disclosure, mono-dispersed micro-beads of polydimethylsiloxane (PDMS) can be created in a microfluidic system using flow-focusing. A PDMS precursor solution may be dispersed into micro-droplets within an aqueous continuous phase. These droplets may then be collected and thermally cured into solid micro-beads. These techniques allow incorporation of depletion media 106 into the PDMS micro-beads. The flow-focusing mechanism creates droplets of PDMS precursors in an aqueous continuous phase bearing the surfactant, sodium dodecyl sulfate (SDS). See, for example, Jiang et al., "Microfluidic synthesis of monodisperse PDMS microbeads as discrete oxygen sensors," Soft Matter, 8:923-926 (2006), herein incorporated by reference in its entirety.

In an embodiment of the present disclosure, the silicone elastomer may be Sylgard® 184. Sylgard® 184, a common PDMS elastomer kit from Dow Corning®, can be used as the dispersed phase. Sylgard® 184 is composed of two fluids, Part A (base, consisting of vinyl-terminated siloxane oligomers) and Part B (curing agent, consisting of siloxane oligomers and catalyst), that have to be mixed and thermally cured to form the final PDMS polymer. The ratios of Part A and Part B may be adjusted to decrease the viscosity for generating stable droplets. In embodiments according to the present disclosure, depletion media 106 can be directly added to the PDMS precursor solution.

In other embodiments, microspheres may be created with coaxial cicctrohydrodynamic atomization (CEHDA). This process can generate droplets down to 1 to 2 mm (see, Ganan-Calvo et al., "Current and droplet size in the electrospraying of liquids. Scaling laws," J. Aerosol Sci., 28:249-275 (1997); and Jayasinghe et al., "Controlled deposition of nano-particle clusters by electrohydrodynamic atomization," Nanotechnology, 15:1519-1523 (2004)). An aqueous solution of depletion media 106 may be created and pumped through an inner capillary while a PDMS solution is pumped through the outer capillary. A several kilovolt potential difference is applied between the capillary and ground electrode to develop a Taylor Cone (conical shaped liquid meniscus at the capillary outlet). The high charge density creates a thin jet which breaks down into droplets creating the microsphere particles. The resulting microspheres may then be collected and thermally cured.

In other embodiments, microspheres can also be formed as taught in Ziemelis, U.S. Pat. No. 4,370,160, issued Jan. 25, 1983, entitled "Process for Preparing Silicone Micro-Particles," or inorganic sorbent can be incorporated into microspheres as described in Morita et al., U.S. Pat. No. 5,387,624, issued Feb. 7, 1997, entitled "Method for the Preparation of a Powder Mixture Composed of Cured Silicone Microparticles and Inorganic Microparticles." The inorganic sorbent can also be blended into the silicone as described in Hottle et al., U.S. Pat. No. 6,210,601, issued Apr. 3, 2001, entitled "Method of Making an Oxygen Scavenging Sealant Composition." Each of these patents is hereby incorporated by reference in its entirety.

In other embodiments according to the present disclosure, a lower concentration or partial pressure of a gas of depletion chamber 115 may be achieved by providing a depletion gas 114. A depletion gas 114 is an oxygen free gas, a carbon dioxide free gas, or an oxygen and carbon dioxide free gas. Several gases including, but not limited to, argon, helium, and nitrogen may be used as a depletion gas 114. In certain embodiments, a depletion gas 114 may be a mixture. In some embodiments, a depletion gas 114 may include CO$_2$.

In embodiments according to the present disclosure, a depletion device may combine one or more depletion chambers 102 that have either a depletion media 106 or depletion gas 114. In an embodiment, a depletion device may have a depletion chamber 102 with a depletion media 106 and a depletion chamber 115 having a depletion gas 114. In another embodiment, a depletion device may have two depletion chambers 102 having a depletion media 106 and a depletion chamber 115 having a depletion gas 114. In other embodiments, a depletion device may have a depletion chamber 102 with a depletion media 106 and two depletion chambers 115 having a depletion gas 114.

In certain embodiments, a depletion gas 114 may be oxygen free and have a non-zero partial pressure of carbon dioxide. In an embodiment, the partial pressure of oxygen is at or near zero mmHg and the partial pressure of carbon dioxide is 5 mmHg (5 Torr). In another embodiment, the partial pressure of oxygen is at or near zero mmHG and carbon dioxide is less than 5 mmHg. In a further embodiment, the partial pressure of oxygen is at or near zero mmHG and carbon dioxide is at or near zero mmHg. In an embodiment, a $pCO_2$ is about 5 mmHg and a $pO_2$ is about 10 mmHg. In another embodiment, $O_2$ may be depleted to a level of about 1 part per billion (ppb) and $CO_2$ may be depleted to at least 1 part per million (ppm). In another embodiment, an oxygen free gas may have $CO_2$ at about 10 mmHg. In another embodiment, an oxygen free gas may have $CO_2$ at about 20 mmHg or more. In embodiments according to the present disclosure, an oxygen free gas may have 5, 10, 15, 20, 25, 30, 35, 40 or 45 mmHg of $CO_2$. In yet another embodiment, an oxygen free gas may have $CO_2$ at about zero to 50 mmHg. In an embodiment, an oxygen free, carbon dioxide reduced gas may be argon having about 5 mmHg $CO_2$.

By way of non-limiting illustration, FIGS. 8A-C and 9A-C provide exemplary embodiments of gas depletion devices having at least one gas depletion chamber 115 having one or more gas inlets 111 and one or more gas outlets 112. In some embodiments, a gas depletion device may have two, three or four gas inlets 111 and two, three or four gas outlets 112. Referring to FIG. 8A, a gas depletion device may have two gas inlets 111 and two gas outlets 112. It should be readily understood that gas inlets 111 and gas outlets 112 may be arranged to provide a countercurrent flow of a depletion gas 114 relative to the flow of liquid through a liquid chamber 101. In other embodiments, the flow of depletion gas 114 relative to the flow of liquid in liquid chamber 101 may alternate between a counter-current flow and a concurrent flow.

In an embodiment according to the present disclosure, gas inlets 111 and gas outlets 112 may be arranged in parallel such that each gas depletion chamber 115 is provided a separate stream of depletion gas 114. In some embodiments, one or more gas depletion chambers 115 may be connected in series by connecting a first gas outlet 112 to a second gas inlet 111, either directly or through a connecting tube. Similarly, in some embodiments, a second gas outlet 112 may be connected to a third gas inlet 111, either directly or through a connecting tube. According to embodiments of the present disclosure, the number of gas depletion chambers 115 that may be connected in series may be two or more. In another embodiment, three or more gas depletion chambers 115 may be connected in series. In another embodiment, four or more gas depletion chambers 115 may be connected in series. In another embodiment, five or more gas depletion chambers 115 may be connected in series. It should be apparent that the number of gas depletion chambers that may be connected in series depends on the flow of depletion gas 114 such that the concentration or partial pressure of oxygen, carbon dioxide, or both is less than the concentration or partial pressure of oxygen, carbon dioxide, or both in the liquid chamber.

Figure 9A:
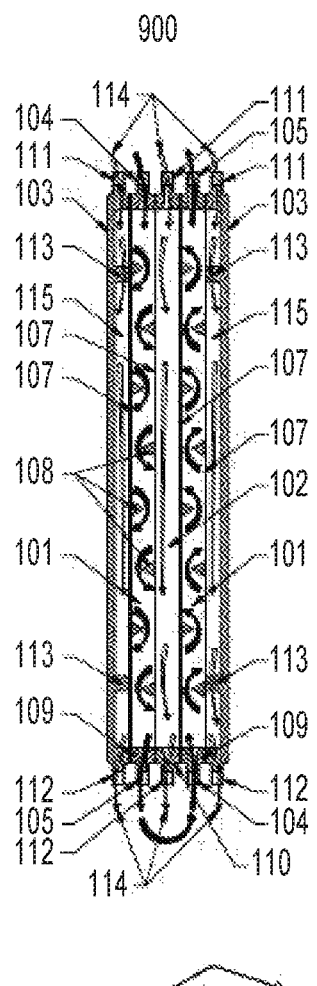
FIGS. 9A-C illustrate an exemplary multi chamber depletion device having two liquid chambers in a series configuration and three gas depletion chambers according to the present disclosure.
Figure 9B:
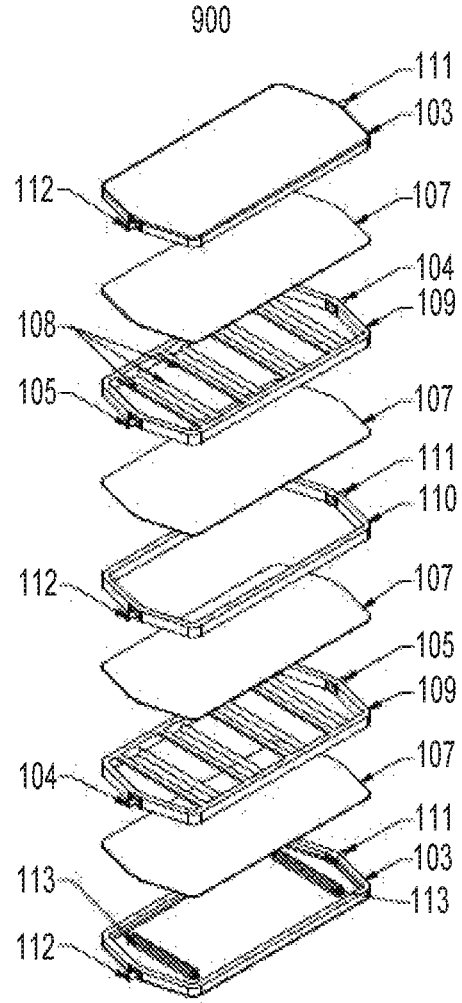
Figure 9C:
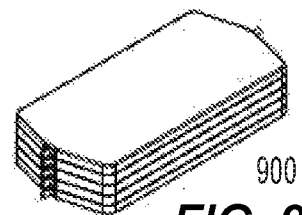

Referring to FIGS. 9A-C, a gas depletion device of the present disclosure may have three or more depletion chambers 115. As shown, a device having three depletion chambers 115 may be supplied with three streams of depletion gas 114 in parallel through separate gas inlets 111. In some embodiments, depletion gas 114 may be provided in series as described above such that a first gas outlet 112 is connected directly or through tubing to a second gas inlet 111. In other embodiments, depletion gas 114 may be provided as a countercurrent flow of depletion gas relative to the flow of liquid in liquid chambers 101. In further embodiments, the flow of depletion gas relative to the flow of liquid in liquid chamber 101 may alternate between a countercurrent flow and a concurrent flow. In embodiments according the present disclosure, a gas depletion device having more than one gas depletion chamber 115 may be supplied with a single source of depletion gas 114. Accordingly, each gas inlet 111 for each depletion chamber 115 would be supplied through a manifold which splits and divides the flow of depletion gas 114 to each separate depletion chamber 115. Similarly, a gas depletion device of the present disclosure having a single source of depletion gas may further include an outlet manifold which combines the exhaust gas flow from one or more gas outlets 112.

Figure 11A:
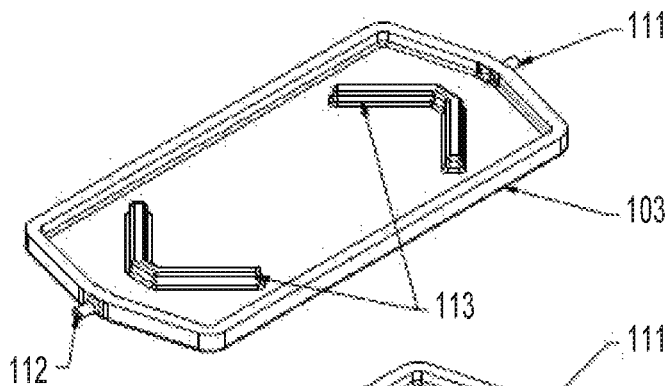
FIGS. 11A-C illustrate exemplary gas flow control features according to the present disclosure.
Figure 11B:
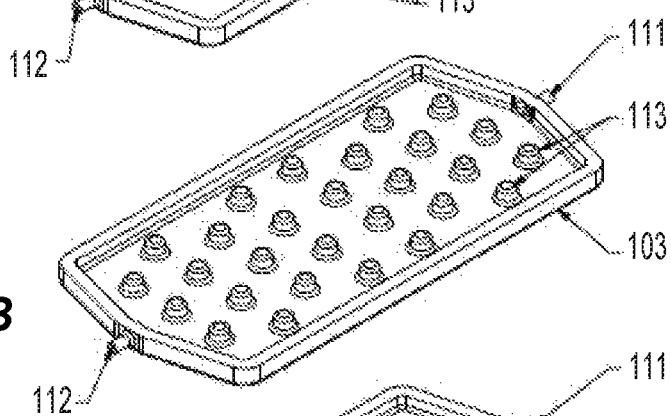
Figure 11C:
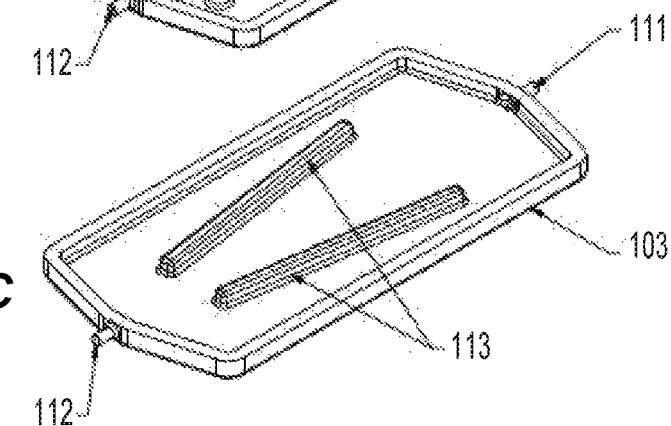

As illustrated in FIGS. 8A-C, 9A-C, and 10A-C, a gas depletion chamber 115 may include one or more gas flow control features 113. As provided in the illustrations, two gas flow control features 113 (shown as horizontal bars) provide for the mixing of depletion gas 114 to maximize the concentration or partial pressure difference between the gas depletion chamber 115 and liquid chambers 101 thereby increasing the efficiency and rate of gas diffusion across one or more gas permeable barriers 107. In yet other embodiments, the geometry of a gas flow control feature 113 may be modified, as illustrated in FIGS. 11A-C. In further embodiments, a gas depletion device of the present disclosure may include a combination of gas flow control features 113. In embodiments according the present disclosure, flow control features may be modified to adjust for gas flow (see below). In another embodiment, the gas flow control features 113 may be modified to achieve a desired partial pressure and to avoid desiccating the liquid. In certain embodiments, the gas flow control features 113 are designed to eliminate bubble formation. In some embodiments, the gas flow control features 113 are designed to eliminate any pressure that will displace the liquid.

According to the present disclosure, gas permeable barriers 107 are barriers that are impermeable to a liquid and are porous to one or more gases. Gas permeable barriers 107 may be formed as a membrane, film, fiber, or mesh. In some embodiments, a gas permeable barrier 107 may be a hydrophobic porous structure. In certain embodiments, a gas permeable barrier 107 may be a low liquid permeability barrier that allows one or more gases to pass through. In some embodiments, a gas permeable barrier 107 may be impermeable to liquid through their operation at a liquid-side pressure that is below the intrusion pressure of the membrane.

In embodiments according to the present disclosure, a gas permeable barrier 107 may be a non porous material that is capable of high gas permeability rates. In some embodiments, a gas permeable barrier 107 may be capable of high oxygen permeability rates. In some embodiments, a gas permeable barrier 107 may be capable of high carbon dioxide permeability rates. In further embodiments, a gas permeable barrier 107 may be capable of high oxygen and carbon dioxide permeability rates.

Gas permeable barriers 107 according to the present disclosure include membranes, films, fibers or meshes that are constructed of polymers. Non-limiting examples of polymers suitable for the preparation of gas permeable barriers 107 of the present disclosure include polyolefins, silicones, epoxies, and polyesters. In other embodiments, the gas permeable barriers 107 may be constructed from Teflon, PVDF, or polysulfone, inorganic materials including ceramics, and combinations of each. Suitable materials for gas permeable barriers 107 according to the present disclosure include polysulfone, cellulose acetate, polypropylene, polyvinylidene difluoride, polyether sulfone, polyvinyl alcohol, polymethylmethacrylate, and combinations thereof. Non-limiting examples of gas permeable barriers 107 include PVDF membranes manufactured by EMD Millipore having membrane codes VVHP, GVHP, HVHP, DVHP, HAWP, DAWP, AAWP, RAWP, SSWP, SMWP, SCWP, SVPP, VEPP, GEPP, EIMF, HEMF, HEPP, VVSP, GVSP, HVSP, DVSP, BVSP and SVSP.

In embodiments according to the present disclosure, gas permeable barriers 107 have an average surface pore size that may be characterized by methods known in the art such as scanning electron microscopy. In some embodiments, a gas permeable barrier 107 may have an area-average surface pore size of about 8 µm or less, or less than 3 µm. By porometry or bubble point test, the average pore size of gas permeable barriers 107 may be between about 0.1 and 1 µm. In certain embodiments, the average pore size is less than 4 µm.

According to the present disclosure, gas permeable barriers 107 may be formed from at least one material selected from the group consisting of PVDF rendered hydrophilic, nylon, cellulose esters, polysulfone, polyethersulfone, polypropylene rendered hydrophilic, and polyacrylonitrile. In embodiments according to the present disclosure, a hydrophilic microporous membrane may be a multilayered membrane. In an embodiment, a gas permeable barrier 107 may be a multilayered membrane having two or more materials selected from the group consisting of: PVDF rendered hydrophilic, nylon, cellulose esters, polysulfone, polyethersulfone, polypropylene rendered hydrophilic, and polyacrylonitrile. Gas permeable barriers 107 of the present disclosure may be further surface modified to control cell adhesion, protein binding and fouling. In some embodiments, a gas permeable barrier 107 may be modified to increase the hydrophilicity. In an embodiment, a polysulfone material may be combined with PVP to prepare membranes with increased hydrophilicity. In an embodiment, the gas permeable barrier 107 may be prepared from polysulfone. In an embodiment according the present disclosure, a gas permeable barrier 107 may be hydrophilic microporous membrane. In other embodiments, a gas permeable barrier 107 may be formed from more than one hydrophilic microporous membrane. In some embodiments, more than one membrane may be fused together to prepare a gas permeable barrier 107. In other embodiments, more than one membrane may be layered to prepare a gas permeable barrier 107. In some embodiments, a layered membrane may be separated by a media. In an embodiment, the media may be a depletion media as provided above.

In embodiments according to the present disclosure, a gas permeable barrier 107 may be less than 250 microns thick. In an embodiment, a gas permeable barrier 107 may be greater than 25 microns thick. In some embodiments, a gas permeable barrier 107 may be between 25 and 250 microns thick. In other embodiments, a gas permeable barrier 107 may be between 25 and 100 or 25 and 150 microns thick. In an embodiment, a gas permeable barrier 107 may be between 50 and 100 microns thick, 75 and 100 microns thick, 50 and 150 microns thick, 75 and 150 microns thick, 100 and 250 microns thick, 150 and 250 microns thick, or between 25 and 150 microns thick.

The lowest oxygen saturation may be achieved by using devices in which depletion media 106 is placed close to gas permeable barrier 107 and, in turn, a liquid in liquid chamber 101 to enable rapid diffusion time. Additional factors that increase gas diffusion are larger active surface area of gas permeable barrier 107. The scavenging rates of depletion media 106 may be limited by the surface area available for reaction with oxygen or oxygen and carbon dioxide and how readily the oxygen or oxygen and carbon dioxide diffuses into depletion media 106. Surface area availability can be increased by incorporating the depletion media 106 into microparticles or microfibers as provided above.

In certain embodiments according to the present disclosure, a gas permeable barrier 107 may include a biocompatible leukocyte binding surface chemistry on the surface of the gas permeable barrier 107 in liquid contact with a liquid chamber 101. In certain embodiments, a liquid chamber 101 may include one or more leukocyte binding materials to reduce the number of leukocytes in a liquid flowing in a liquid chamber 101. In an embodiment, a gas permeable barrier 107 may further comprise one or more additional layers having a biocompatible leukocyte binding surface chemistry. In other embodiments according the present disclosure, a device may include a separate biocompatible leukocyte binding material. In certain embodiments, a biocompatible leukocyte binding material may be a membrane with a binding surface chemistry. In some embodiments, the leukocyte binding material may be a binding matrix. In other embodiments, a biocompatible leukocyte binding material may be a leukoreduction material 123.

Leukoreduction materials suitable for methods of the present disclosure may be prepared as either filters, fibers, microspheres or microparticles. In an embodiment, leukocyte reduction filters may be formed as described in Lee et al., U.S. Pat. No. 6,337,026, issued Jan. 8, 2002, entitled "Leukocyte reduction filtration media," using micro-glass fibers. Gas permeable barriers as described above can be used as a base and then grafted PVA or Silicone can be used to coat the gas permeable barrier 107 and promote leukocyte adhesion. In another embodiment, melt blown fibers as described in Pall, U.S. Pat. No. 4,925,572, issued May 15, 1990, entitled "Device and method for depletion of the leukocyte content of blood and blood components," can be formed from PBT or PET and then incorporated into filter devices as taught in Pall et al., U.S. Pat. No. 5,229,012, issued Jul. 20, 1993, entitled "Method for depletion of the leucocyte content of blood and blood components," and surface modified as described in Gsell, U.S. Pat. No. 5,443,743, issued Aug. 22, 1995, entitled "Gas plasma treated porous medium and method of separation using same." All of which are herein incorporated by reference in their entireties.

In another embodiment, gas permeable barriers 107 as described above can also be surface modified as described in Bonaguidi et al., U.S. Pat. No. 7,775,376, issued Aug. 17, 2010, entitled "Filter for the separation of leukocytes from whole blood or blood preparations, method for production of said filter, corresponding device and use thereof," hereby incorporated by reference in its entirety. In another embodiment, the monomers of Bonaguidi et al. may be grated onto a silicone coating instead of polymerized. Gas permeable barriers 107 can be included into conventional leukoreduction fibers made of PBT or PET as taught in Clauberg et al., U.S. Pat. No. 6,610,772, issued Aug. 26, 2003, entitled "Platelet Particle Polymer Composite with Oxygen Scavenging Organic Cations," hereby incorporated by reference in its entirety. Additional limitations and requirements of leukocyte reduction filters may be found in Watanabe et al., U.S. Pat. No. 4,701,267, issued Oct. 20, 1987, entitled "Method for Removing Leukocytes," hereby incorporated by reference in its entirety.

Depletion devices of the present disclosure having leukoreduction capabilities include and provide for the preparation of leukoreduced blood products including packed red blood cells. In an embodiment, the number of leukocytes is reduced to a level below 1000 cells/µl. In another embodiment, the number of leukocytes is reduced to a level below 100 cells/µl. In yet another embodiment, the number of leukocytes is reduced to a level below 10 cells/µl. In an embodiment according to the present disclosure, the number of leukocytes remaining after leukoreduction may be from 1 cell to 10 cells/µl. In another embodiment, the number of leukocytes remaining may be from 5 to 20 cells/µl. In another embodiment, the number of leukocytes remaining may be from 5 to 10 cells/µl, 5 to 50 cells/µl, 5 to 100 cells/µl, 10 to 20 cells/µl, or 5 to 100 cells/µl. In certain embodiments according the present disclosure, the number of leukocytes is determined by flow cytometry.

In embodiments according to the present disclosure liquid chambers 101 and gas depletion chambers 102 may contain flow control features 108 and 113. The number, position, size and shape of the flow control features 108 and 113 may be altered to optimize the gas depletion devices of the present disclosure. In an embodiment, a flow control feature 108 may be configured to direct the flow of liquid against the gas permeable barrier 107. In other embodiments, a flow control feature 113 may be configured to direct the flow of depletion gas 114 along a gas permeable barrier 107.

Figure 1D:
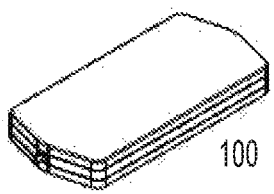

Flow control features 108 according the present disclosure may be of different shapes and sizes. As illustrated in FIG. 1D, flow control feature 108 are depicted as approximately one-half the height of the liquid chamber 101 (see, e.g., FIG. 1B). This ratio may be altered for different flow rates. Also as illustrated in the figures, flow control features 108 may be triangular (see, e.g., FIGS. 1A, 1B, 2A, 2B, 3A, 4A, 8A, 9A, 10A, 12A, 13A, 14A, and 15A). In other embodiments, flow control features may be semi-circular, ovoid, square or any combination of thereof (see, e.g., FIGS. 2A-F). As illustrated in, for example, FIGS. 1C, 2B, 8C and 9B, flow control features 108 may extend across the width of liquid chamber 101. In other embodiments, flow control features 108 may include openings or gaps.

Referring to FIGS. 2A-F, flow control features 108 include a variety of shapes, position and number. In certain embodiments, the flow control features 108 may be positioned flush with the outside surface of inner shell 109 as shown in FIGS. 2A and 2B. In other embodiments, the flow control features 108 may be offset from the surface of the inner shell 109 and illustrated in FIGS. 2C to 2F. In certain embodiments according to the present disclosure, flow control features 108 may be triangular, rectangular or circular as illustrated in FIGS. 2A to 2F. In other embodiments, the flow control features 108 may be combinations of triangular, rectangular or circular shapes. In an embodiment, a flow control feature 108 may be semicircular. The flow control features 108 according to the present disclosure may be present in varying numbers. For example as illustrated in FIGS. 2A and 2B, there may be eight flow control figures. In other embodiments, there may be more than eight flow control features 108, for example, 9, 10 or 11 flow control features 108. In some embodiments, there may be fewer than eight flow control features 108. For example there may be 1 or more flow control features 108. In some embodiments, there may be fewer than eight flow control features 108. In certain other embodiments, there may be 2 or more flow control features 108. In other embodiments, there may be 3 or more flow control features 108. In yet other embodiments, there may be 4 or more flow control features 108. In further embodiments, there may be 5 or 6 flow control features 108.

The number and position of flow control features 108 can also be altered to optimize the process for a specific configuration. As illustrated in FIGS. 1A-D, the flow features may be incorporated as flow control features 108 on alternate sides of a liquid chamber 101 and may further include an offset such that the liquid flows in a zig-zag direction as it proceeds through the liquid chamber 101 (see, e.g., FIGS. 1A, 2A-B, 3A, 4A, 6A, 8A, 9A, 10A, 12A, 13A, and 14A). Flow control features 108 included on opposing sides of a liquid chamber 101 provide for both directing the flow of liquid against gas permeable barrier 107 and for mixing the flowing liquid to maintain disequilibrium between the concentration or partial pressure of the gas in the liquid and the concentration or partial pressure in the depletion chamber 102.

The number and position of flow control features 108 can also be altered to optimize the process for a specific configuration. A gas depletion device may have one or more flow control features 108. In an embodiment, a gas depletion device may have two or more flow control features 108. In another embodiment, a gas depletion device may have three or more flow control features 108. In other embodiments, a gas depletion device may have four or more flow control features 108. In another embodiment, a gas depletion device may have five or more flow control features 108. In some embodiments there may be six, seven or eight or more flow control features 108.

Flow control features 113 according the present disclosure may be of different shapes and sizes. As illustrated in FIGS. 8A, 9A, and 10A, gas flow control features 113 are depicted that direct the flow of gas around the outside of the device so that the flow runs parallel to the gas permeable membrane 107. Gas flow control features 113 may introduce turbulence in the gas flow to ensure mixing and maintain the rate of diffusion across a gas permeable membrane 107. Also as illustrated in the figures, gas flow control features 113 may be triangular. In other embodiments, flow control features may be semi-circular, ovoid, square or any combination of thereof (see also, FIGS. 2A-F and FIGS. 11A-C). As illustrated in FIGS. 8B, 9B and 10B, gas flow control features 113 may extend across less than the width of gas depletion chamber 115. In other embodiments, gas flow control features 113 may include openings or gaps to provide for branching and joining of the gas flow.

The number and position of gas flow control features 113 can also be altered to optimize the process for a specific configuration. As illustrated for flow control features 108, gas flow features 113 may be incorporated on alternate sides of a gas depletion chamber 102 and may further include an offset such that the gas flows in a zig-zag direction as it proceeds through the gas depletion chamber 102. Gas flow control features 113 may be included on opposing sides of a gas depletion chamber 102 to provide for both directing the flow of liquid against gas permeable barrier 107 and for mixing the flowing gas to maintain disequilibrium between the concentration or partial pressure of the gas in the liquid and the concentration or partial pressure in the depletion gas.

The number and position of gas flow control features 113 can also be altered to optimize the process for a specific configuration. A gas depletion device may have one or more flow control features 113. In an embodiment, a gas depletion device may have two or more flow control features 113. In another embodiment, a gas depletion device may have three or more flow control features 113. In other embodiments, a gas depletion device may have four or more flow control features 113. In another embodiment, a gas depletion device may have five or more flow control features 113. In some embodiments, there may be six, seven or eight or more flow control features 113.

Referring to FIGS. 5A-C and 7A-C, a depletion device according to the present disclosure may include one or more flexible or expandable depletion chambers 102 and one or more flexible or expandable liquid chambers 101. To provide for mixing and efficient diffusion of a gas from a liquid chamber 101 to a depletion chamber 102, a depletion chamber 102 of a flexible depletion device may include one or more flow control features 108. In certain embodiments, flow control features are provided to direct the liquid flow in a pattern with corners set at variable angles. Referring to FIGS. 6A-C, flow control features may include an indirect path 133. In certain embodiments, the liquid flow would proceed in a zig-zag manner. In some embodiments, the flow may follow a regular pattern, branching and rejoining prior to exiting through liquid outlet 105. In other embodiments, the flow may follow an irregular pattern. In some embodiments, the liquid flow may be divided into two or more individual flows. In other embodiments, the liquid flow may be divided 2, 4, 6 or more times. In certain embodiments with divided flows, the flows may be recombined before exiting through an outlet 105.

Depletion devices according to the present disclosure include at least one inlet 104 and at least one outlet 105. Although depicted in the illustrations with inlets 104 at the top and outlets 105 at the bottom, the flow of liquids and gases may be reversed. In some embodiments, the flows are arranged to provide for a countercurrent flow. In some embodiments, an outlet 105 may be connected to an inlet 104, for example as illustrated in FIGS. 9A-C, device 900. In an embodiment, the liquid chambers 101 may be connected via inlets 104 and outlets 105 to provide for parallel flow.

Depletion devices according to the present disclosure may comprise one or more liquid chambers 101 and one or more depletion chambers 102. In some embodiments, chambers 101 and 102 may be stacked and combined into a single depletion device. In a stacked configuration, a depletion device may arrange the liquid chambers 101 in a serial or parallel configuration in liquid communication with each other. According to the present disclosure, stacking the depletion chambers 102 and liquid chambers 101 combined with altering the internal features and ratios of the liquid chamber 109 and the control features 108 may be continued to create as many layers as required to meet the gas depletion process requirements. In certain embodiments, a depletion device may provide for the parallel flow of the fluid through two or more liquid chambers 101 by dividing the fluid flow using a splitter 130 as illustrated in FIG. 10A. In a parallel chambered depletion device, the fluid flow through liquid outlet 105 is rejoined with joiner 131. In an embodiment, for example as illustrated in FIGS. 10A-C, a device 1000 may have two parallel liquid chambers 101 and three gas depletion chambers 114. In other embodiments, three or more parallel liquid chambers 101 may be provided. In yet other embodiments, a combination of parallel and serial liquid chambers 101 may be provided.

In other embodiments, depletion devices according to the present disclosure may further include an anaerobic plasma port 116 as illustrated in FIGS. 7A-C and 8A-C.

Included and provided for in the present disclosure are gas addition devices having a structure similar to the structure of a depletion device similar to those illustrated in FIGS. 8A-C and 9A-C provided above. A gas addition device may supply one or more gases to an oxygen or oxygen and carbon dioxide depleted blood product prior to transfusion. A gas addition device according to the present disclosure may have one or more streams of an addition gas. For example, a gas addition device may have an oxygen addition gas and a nitric oxide addition gas provided separately to a single gas addition device similar to one illustrated in FIGS. 9A-C.

Referring to FIGS. 16A-C, a gas addition device may provide for the reoxygenation of an anaerobic liquid, such as anaerobic stored red blood cells, prior to transfusion into a patient in need. For example, anaerobic packed red blood cells enter through liquid inlet 104 and flow through liquid chamber 101 having flow control features 108. As the packed red blood cells pass through the device, oxygen provided through gas addition ports 128 diffuse through gas permeable barriers 107 and are bound by hemoglobin in the red blood cells. As illustrated in device 1600, the gas addition gas ports 128 provide for the passage of ambient air through outer shell 103. In other embodiments, addition ports 128 may further comprise inlets capable of connecting to a gas supply to provide an oxygen rich gas.

Gas addition devices according to the present disclosure may provide a gas to a gas depleted blood product prior to transfusion. A gas addition device of the present disclosure includes devices as described above wherein a depletion gas 114 is replaced by an addition gas and a depletion chamber 102 is replaced by an addition chamber. In an addition device, a gas flows through one or more gas addition chambers, thereby providing a source of addition gas at a higher concentration or partial pressure than a liquid flowing in a liquid chamber 101. As provided above, a gas addition chamber is separated from a liquid chamber by a gas permeable barrier. In embodiments of a gas addition device, a liquid chamber is provided with one of more flow control features 108 to ensure mixing of the liquid and maintenance of a strong diffusive force provided by the difference in concentration or partial pressure of the gas. Similarly, a gas addition chamber may also include flow control features 113 to ensure mixing and gas equilibration.

In embodiments according to the present disclosure, an addition gas may be an oxygen containing gas. In an embodiment, an oxygen containing gas may comprise ambient air having about 20% oxygen. In another embodiment, an addition gas may have an increased oxygen percentage compared to ambient air. In an embodiment, the percent oxygen may be more than 20%. In another embodiment, the percent oxygen may be more than 30%. In another embodiment, the percent oxygen may be 40%, 50% or more. In yet another embodiment, the addition gas may be pure oxygen. In other embodiments, the oxygen containing gas may have less than 20% oxygen. In an embodiment, the addition gas may have 15% oxygen or 10% oxygen, or less.

In embodiments according to the present disclosure, an addition gas may be a nitric oxide containing gas. In some embodiments, the addition of NO may occur prior to the addition of oxygen in preparation for transfusion due to the inherent instability of NO in the presence of oxygen. In certain embodiments, an addition gas having nitric oxide is provided to an anaerobic blood product using a gas addition device prior to the addition of $O_2$ by a gas addition device. In other embodiments, an integrated $NO/O_2$ addition device maintains a first stream of NO addition gas in a gas addition chamber 134 thus supplying an adjacent liquid chamber 101 with NO. A second oxygen addition gas, provided to a second gas addition chamber provides a source of oxygen to a second liquid chamber in liquid communication with a first NO gas supplied liquid chamber. One or more NO addition steps and one or more $O_2$ addition steps may be provided by stacking gas addition chambers and liquid chambers as provided above. In some embodiments, an addition gas may comprise carbon dioxide together with or in a separate gas stream. In an embodiment, an addition gas may include 5% $CO_2$. In another embodiment, an addition gas may include 2.5% $CO_2$. In a further embodiment, an addition gas may include from 1 to 5% $CO_2$. In other embodiments, an addition gas may include from 2 to 4% or 2 to 5% $CO_2$. Other embodiments may include more than 5% $CO_2$ in an addition gas.

Depletion devices according the present disclosure may be used with anaerobic storage bags that are capable of storing red blood cells or a blood product anaerobically and in a $CO_2$ depleted state.

Storage bags compatible with methods and systems of the present disclosure may be a laminated bag having an oxygen and carbon dioxide sorbent or a secondary bag containing an oxygen and carbon dioxide sorbent. In other embodiments, a compatible storage bag may comprise an inner blood storage bag having DEHP-plasticized PVC in contact with RBCs or blood product. A compatible storage bag may further comprise an outer transparent oxygen barrier film (e.g., nylon polymer) laminated to the outer surface inner blood bag. In other compatible embodiments, a storage bag may be a bag within a bag, wherein the outermost bag comprises an oxygen barrier film. Storage bags compatible with blood products produced by the depletion devices according to the present disclosure include storage bags that include one or more sorbents, including oxygen sorbents.

Exemplary storage bags may be found, for example, in U.S. application Ser. No. 12/901,350, filed Oct. 8, 2010, entitled "Blood Storage Bag System and Depletion Devices with Oxygen and Carbon Dioxide Depletion Capabilities," and herein incorporated by reference in its entirety.

Blood products suitable for use in a depletion device of the present disclosure include platelet depleted blood products. In an embodiment, a suitable blood product is a platelet depleted packed red blood cell blood product. Platelets, in contrast to red blood cells, require $O_2$ for metabolism. Thus, platelets may be damaged by depletion of oxygen and storage under anaerobic conditions. Accordingly, removal of platelets prior to, or after treatment with a device of the present disclosure may avoid the release of substances that may compromise the quality of a stored depleted blood product. Exemplary platelet depletion coatings are provided in, for example, in U.S. Pat. No. 4,880,548, entitled "Device and method for separating leucocytes from platelet concentrate," issued Nov. 14, 1989, U.S. Pat. No. 5,783,094, entitled "Whole blood and platelet leukocyte filtration method," issued Jul. 21, 1998, U.S. Pat. No. 7,721,898, entitled "Coating material for leukocyte removal filter and the filter," issued May 25, 2012, and U.S. Pat. No. 7,775,376, entitled "Filter for the separation of leukocytes from whole blood or blood preparations, method for production of said filter, corresponding device and use thereof," issued Aug. 17, 2010, each of which is incorporated herein in its entirety.

The present disclosure provides for, and includes methods for the use of a device or devices disclosed herein and described below. Provided for and included are methods for preparing an oxygen or oxygen and carbon dioxide depleted blood product using a device or devices of the present disclosure. The present disclosure further provides for, and includes, methods for the extended storage of a blood product using a disclosed depletion device. A method may be designed using a device or devices disclosed herein that adopts a combination of the steps described herein. Blood products suitable for depletion methods using a disclosed device include, for example, whole blood, packed red blood cells, platelet depleted whole blood, platelet depleted packed red blood cells, edited whole blood, and edited packed red blood cells.

The present disclosure provides for and includes a depletion device having an enclosure, one or more liquid chambers, one or more depletion chambers, at least one gas permeable barrier, at least one liquid inlet and at least one liquid outlet. Methods according to the present disclosure may include collection of blood, passage through a described depletion device, storage in an anaerobic storage bag, re-oxygenation using a device of the present disclosure, and transfusion into a patient. Methods may further include leukoreduction steps, platelet reduction or separation steps, red blood cell editing steps, pathogen inactivation steps and volume reduction steps. As provided in the present disclosure, method steps may be included in various combinations to provide a blood product suitable for transfusion into a patient in need thereof. The methods of the present disclosure also provide and include methods to enhance the long term storage of blood products.

The present disclosure provides for, and includes, a method for preparing red blood cells (RBCs) including obtaining whole blood, separating the RBCs from the whole blood to form packed RBCs, depleting oxygen to form oxygen depleted RBCs or depleting oxygen and carbon dioxide to form oxygen and carbon dioxide depleted RBCs using a device of the present disclosure and storing the oxygen depleted or oxygen and carbon dioxide depleted RBCs in an anaerobic storage environment to maintain an oxygen depleted or oxygen and carbon dioxide depleted condition.

A method according to the present disclosure provides for the preparation of a depleted blood product using a disclosed device. In an embodiment, the method may include a device that includes an oxygen depletion media 106 or a depletion gas 114 to prepare an oxygen depleted whole blood product. In an embodiment, the method may include a device that includes an oxygen and carbon dioxide depletion media 106 or a depletion gas 114 to prepare an oxygen and carbon dioxide depleted whole blood product.

Methods of the present invention include methods of preparing a blood product for depletion using a disclosed device. In an embodiment, whole blood may be obtained from a donor and applied directly to a device of the present invention. In another embodiment, packed red blood cells may be prepared from whole blood or whole donor blood. Packed red blood cells (pRBC) may be prepared from whole blood using centrifugation techniques commonly known in the art. Packed red blood cells may also be prepared using filtration methods. Packed red blood cells may contain an additive solution. Packed red blood cells can also be collected by aphaeresis techniques such that components are separated during collection. Packed red blood cells may be depleted of oxygen or oxygen and carbon dioxide using a depletion device of the present disclosure.

A device of the present disclosure may be used with methods to prepare leukoreduced, depleted blood products. In an embodiment, a blood product may be passed through a leukoreduction filter to remove leukocytes prior to flowing through a depletion device of the present disclosure. In other embodiments, a depletion device of the present invention may be prepared to include leukoreduction as discussed above. In an embodiment, a device of the claimed invention includes a leukoreduction coating on a gas permeable barrier 107. In another embodiment, a leukoreduction prefilter may be incorporated into a disclosed depletion device. In a further embodiment, a leukoreduction post-filter may be incorporated into a disclosed depletion device.

The present disclosure provides for, and includes, methods for preparing depleted blood products having edited red blood cell populations using a device of the present disclosure. Editing can include removing RBCs that exhibit indications of being compromised. Editing RBCs is the process of identifying and removing blood cells that have a poor likelihood of surviving the transfusion process or will likely die shortly after transfusion. Editing moribund RBCs, or dead or dying red blood cells, may occur before or after processing a blood product using a device, or devices of the present disclosure. For example, editing can be performed immediately before transfusion after storage in an anaerobic storage bag.

Editing can be important because a leading cause of morbidity and mortality to transfused patients is the non-viable portion of the blood that is transfused independent of any pathogen transmission. RBCs that are compromised or that will be removed by the spleen by the reticuloendothelial system shortly after transfusion may threaten to overwhelm the already compromised recipient. Up to 25% of transfused cells are removed by recipient in the first twenty four hours after transfusion. These removed cells are harmful because they contribute immediately to the excess iron burden of the recipient, which may be a critical parameter for chronically or massively transfused patients. Also, these cells may cause capillary blockage due to reduced deformability or aggregate formation, leading to poor tissue perfusion and even organ failure. Thus, substantial benefits are expected if one can remove these less viable RBCs prior to transfusion.

There are several techniques that may be used to edit the red blood cells. The first technique is a centrifugation process to separate old and young RBCs before storage based on characteristic buoyancies of young and old RBCs.

A second technique applies a biomechanical stress, such as an osmotic shock, to hemolyze weak cells before or after storage in combination with a buffer exchange step. The applied biomechanical stress immediately identifies those cells that are weak to rapidly contrast with the stronger RBCs to enable mechanical separation. The weak RBCs are those that contribute to recipient morbidity and mortality, particularly with individuals with already compromised or overloaded immune systems. Up to 25% of RBCs that arrive to a recipient are already dead and can have deleterious effects on the recipient. By editing the RBCs, that number can be reduce by 50% to 75%.

A third technique applies to the deformability of the RBCs. Bump array microfluidic devices containing staggered pillars (Huang, L. R., et al., "Continuous particle separation through deterministic lateral displacement," Science, 304(5673): 987-90 (2004), herein incorporated by reference in its entirety), allow deformable RBCs to pass through the pillars while deformable RBCs cannot pass through the pillars and are bumped into separate channels.

A further technique for editing the RBCs uses a filter system to remove RBC exhibiting a specific surface marker. RBCs exhibiting known surface markers such as phosphatidylserine or aggregated protein 3 can be trapped by a filter surface modified with high affinity ligand (e.g., Annexin IV or antibodies against specific surface marker protein).

An additional technique uses the same high affinity ligands (e.g., specific surface markers) in the second technique, conjugated to make a multimeric molecule such that RBCs exhibiting target surface markers form aggregates. This can then be separated by filtration or centrifugation.

Method of preparing blood products using the devices of the present disclosure may include one or more steps of lymphocyte inactivation and pathogen elimination using gamma- or X-ray irradiation (irradiation generally).

Gamma-irradiation abrogates proliferation of T-lymphocytes by damaging the DNA directly and via reactive oxygen species (ROS), namely hydroxyl radicals produced during gamma-radiolysis of water. Although red blood cells (RBC) do not contain DNA, ROS generated by gamma-irradiation have been shown to cause significant damage to the RBC. The major damage observed includes: i) increased hemolysis; ii) increased $K^+$ leak; iii) reduction in post-transfusion survival; and iv) reduced deformability. Such damage is similar to, but an exaggerated form of storage-induced damage of RBC. The compromised status of RBC is well known to the physicians who administer such compromised RBC. The FDA mandates restricted use of such RBC in terms of shortened shelf life after gamma-irradiation (14 days) and/or 28 days total shelf life for irradiated units.

The irradiation of blood components has received increased attention due to increasing categories of patients eligible to receive such blood to prevent transfusion-associated graft versus host disease. However, irradiation leads enhancement of storage lesions, which could have deleterious effects when such blood is transfused. It is well known in the field that the main deleterious side-effect of radiation on RBC is oxidative damage caused by ROS.

In methods of the present disclosure, a blood product depleted using a device or devices may be irradiated so that it may be transfused to patients requiring irradiated blood products. In an embodiment, a red blood cell composition may be depleted of oxygen or oxygen and carbon dioxide using a described depletion device and then irradiated prior to storage in a gas impermeable storage bag. In another embodiment, a blood product may be depleted of oxygen or oxygen and carbon dioxide using a described depletion device, stored in an anaerobic environment, and irradiate prior to transfusion.

Exemplary methods for irradiation of blood products are illustrated in U.S. patent application Ser. No. 13/289,722, filed Nov. 4, 2011, hereby incorporated by reference in its entirety.

Methods of preparing blood products using the devices of the present disclosure may include one or more buffer exchange steps. In an embodiment, a buffer may be exchanged by centrifugation to sediment the cells, removal of the supernatant and replacement of the liquid with a buffer. In an embodiment, the buffer may be an isotonic buffer. In yet another embodiment, buffer replacement may be accomplished by filtration of the cells and addition of a replacement buffer.

As provided above, devices of the present disclosure provide for the introduction of one or more gases to a depleted blood product. In an embodiment, an oxygen or oxygen and carbon dioxide depleted blood product prepared using a device of the present disclosure may be prepared for transfusion by a method using a gas addition device as described above. In an embodiment, the gas addition device restores O₂ to a blood product such that oxygen saturation is at, or near, 100%. In a method according to the present disclosure, a storage bag containing a depleted blood product is connected to a liquid inlet 104 using a tube, the blood product is allowed to flow through the liquid chamber 101 while an oxygen containing addition gas is provided to gas addition chamber 134 through gas addition ports 128. As a liquid, for example anaerobic stored red blood cells, flows through liquid chamber 101, it absorbs oxygen from a gas flowing through gas addition chamber 134 that diffuses across gas permeable barrier 107. In certain embodiments, the addition ports provide for the flow of ambient air through the device. In other embodiments, addition ports 128 may provide for an oxygen rich gas source to be provided. Any suitable gas may be provided to a gas addition device through addition port 128 including ambient air, pure oxygen and mixtures of oxygen and carbon dioxide. In other embodiments, an addition gas may include NO, either together with O₂ or provided separately. In an embodiment, NO may be provided to an addition device having two gas addition streams and two or more addition chambers, where one gas stream and addition chamber provides O₂, and a second gas stream and addition chamber provides NO.

Methods according to the present disclosure may include collection of blood, passage through a described depletion device, storage in an anaerobic storage bag, re-oxygenation using a device of the present disclosure, and transfusion into a patient. Methods may further include leukoreduction steps, platelet reduction or separation steps, red blood cell editing steps, pathogen inactivation steps and volume reduction steps.

Figure 17:
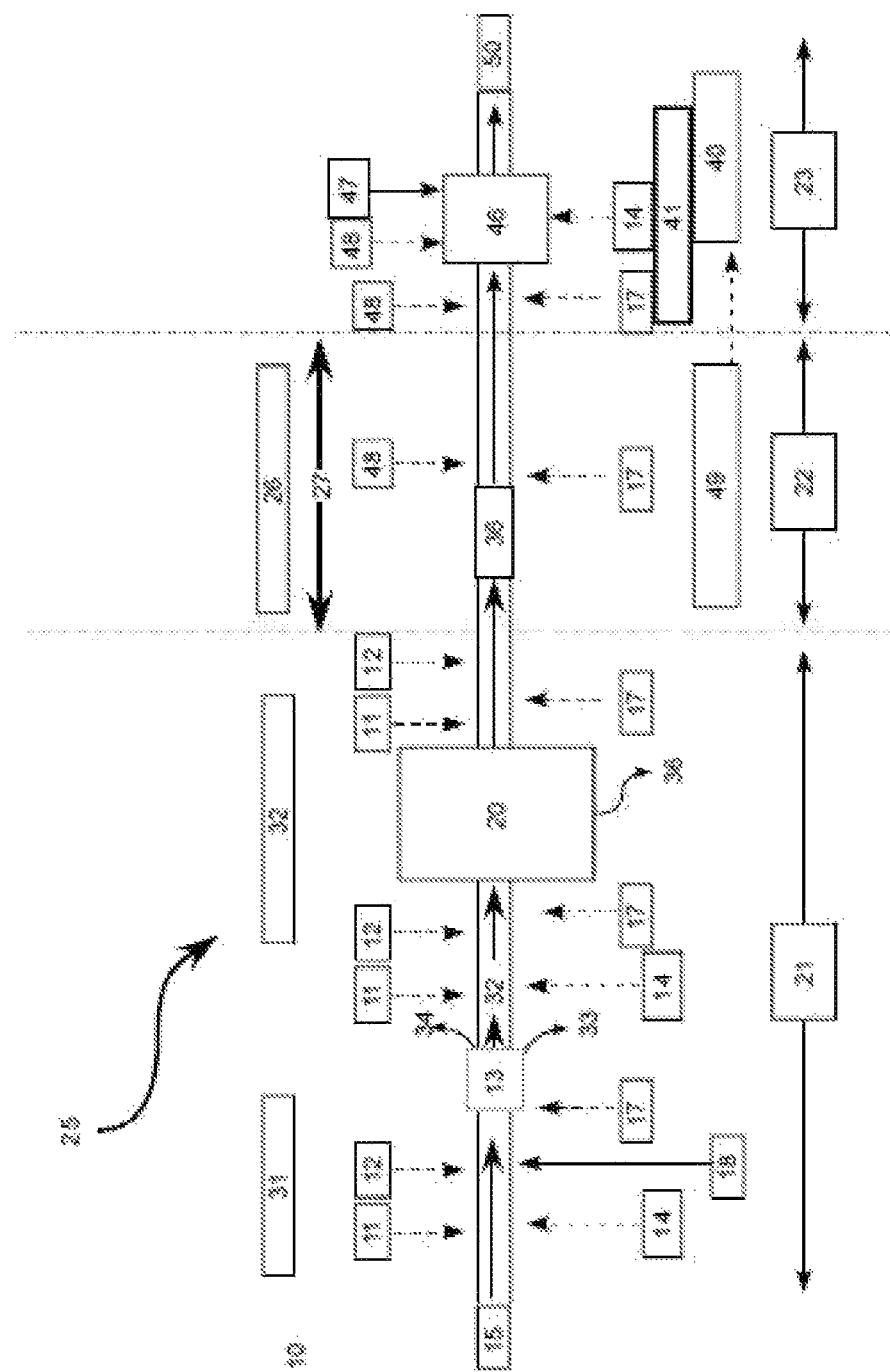
FIG. 17 illustrates an exemplary flowchart of the components and methodology from blood collection to transfusion using a depletion device of the present disclosure in an anaerobic blood storage system.

Devices of the present disclosure may be included in, and integrated into systems and methods for the preparation and extended storage of blood products including, for example, packed red blood cells (pRBC), from receipt of whole blood from a donor until transfusion to a recipient, as shown in FIG. 17.

In its most general form, a system having a depletion device of the present disclosure provides for, and includes, an integrated system and method for the preparation and extended storage of red blood cells, from receipt of whole blood from a donor until transfusion to a recipient. By way of example, FIG. 17 illustrates an exemplary flowchart of the components and methodology from blood collection from a blood donor 15 to transfusion to a recipient 50 using a anaerobic storage method 10 and system 25 through Pre-Storage Phase A 21, Storage Phase B 22 in an anaerobic environment, and Post-Storage Phase C 23. However, as understood with reference to the present disclosure, various combinations of the disclosed systems and methods are envisioned as within the scope of the disclosure, and the illustrated components and methodologies may be optionally substituted, eliminated or reordered.

By way of illustration, method 10 describes a storage system 25 that includes a depletion device 20 of the present disclosure, an anaerobic storage system 26, and post-storage methods and systems to optimize the transfusion process to a recipient 50 and reduce morbidity associated with such transfusion. Provided for, and included in method 10 and storage system 25, are enhancing treatments including leukoreduction 12, editing 14, pathogen inactivation 11 and gamma irradiation 17. Also included and provided for are post-storage methods including gas addition using gas addition devices 46 of the present disclosure to provide oxygen 47 or oxygen 47 and nitric oxide 48 (NO) prior to transfusion to recipient 50. Method 10 also provides for supplement addition 49 and buffer exchange 40 steps.

Again referring to the drawings, and particular to FIG. 17, a method 10 describes storage system 25 from collection from a donor 15 to transfusion to a recipient 50. System 25 shows a method that has three phases during which different sub-processes or steps may occur. The three phases are generally: Pre-Storage Phase A 21, Storage Phase B 22 and Post-Storage Phase C 23. As shown in FIG. 17, different steps of the blood storage method 10 can occur at different phases to achieve optimal blood transfusion results as indicated by dashed arrows. For example, gamma irradiation 17 can optionally occur during Pre-Storage Phase A 21 before depletion using a depletion device 20 of the present disclosure, during Storage Phase B 22, during the Post-Storage Phase C 23, during Storage Phase B 22 and a portion of Pre-Storage Phase A 21 and Post-Storage Phase C 23, or combinations thereof, etc. Similarly, editing 14 of RBCs (e.g., to remove moribund RBCs) can occur during Pre-storage Phase A 21, during Post-storage Phase C 23, or a combination thereof, etc. An anaerobic environment 27 has synergistic relationships with steps such as the addition of nitric oxide 48, gamma irradiation 17 and pathogen inactivation 11, that provide advantages to the RBCs that must occur in such anaerobic environment. Accordingly, there exist several different sequences for the blood storage processing according to the present disclosure.

Pre-storage Phase A 21 includes the time from collection from a donor 15 to storage in an anaerobic environment 27. During Phase A 21, whole blood 31 may be collected from a donor 15, and the blood components, namely, plasma 33, platelets 34 and RBCs 32 may be separated. An optional additive solution 18 may be added to the whole blood to aid in storage and/or processing, as further described herein. Processing such as pathogen inactivation 11, leukoreduction 12 and editing 14 may occur during Pre-storage Phase A 21. During Phase A 21, oxygen, carbon dioxide, or oxygen and carbon dioxide are depleted using the depletion devices 20 of the present disclosure prior to Storage Phase B 22.

Storage Phase B 22 is an anaerobic storage period, wherein anaerobic RBCs 30 are stored in an anaerobic storage environment 27, for example anaerobic storage bag 36. In some embodiments, the anaerobic environment 27 is maintained by an anaerobic storage bag 36 after oxygen depletion using a depletion device 20 of the present disclosure.

Post-Storage Phase C 23, begins after storage in an anaerobic storage environment 27 but prior to transfusion to recipient 50 and may include processing such as volume reduction 41, editing 14, cleansing during buffer exchange 40, the addition of either or both nitric oxide 48 and oxygen 46, etc. In some embodiments, addition of either or both nitric oxide 48 and oxygen 46 may be accomplished using the gas addition devices 46 of the present disclosure.

Figure 18:
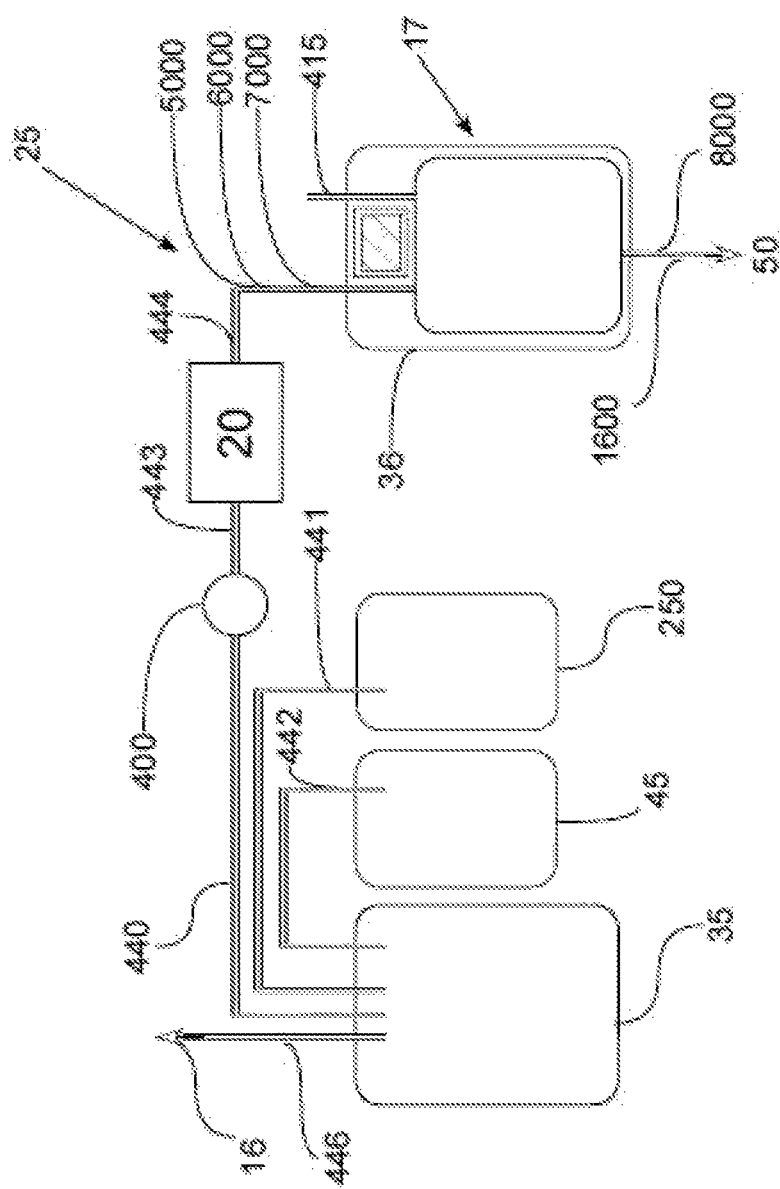
FIG. 18 illustrates an exemplary system according to FIG. 17 of the present disclosure.

Referring to the drawings and in particular to FIG. 18, an exemplary anaerobic storage system 25 is shown. In certain embodiments, system 25 may be constructed so as to be disposable. Again, system 25 is an exemplary system; accordingly, different sub-processes or steps can occur at different times or during different phases as discussed above. Blood storage system 25 includes a depletion device 20 of the present disclosure (for example, devices 100-1500), an anaerobic blood storage bag 36 and an optional additive solution bag 250. Components conventionally associated with the process of blood collection are a phlebotomy needle 16, a blood collection bag 35 containing an anti-coagulant (e.g., an additive 18) and a bag 45 containing plasma. Tubing can connect the various components of the blood storage system 25 in various configurations (one embodiment shown). Depletion devices according to the present disclosure may include a depletion device 100, 200, 300, 400, 500, 600, 700, 800, 900, or 1000), a gas and plasma separation device 1200 or 1300, or a combined leukoreduction, plasma separation depletion device 1400 or 1500. System 25 may also contain a leukoreduction filter 4000, and a editing device 5000, an irradiation device 6000, a pathogen inactivation device 7000, a volume reduction device 8000 and a gas addition device 9000. For example a gas addition device 1600 according the present disclosure to immediately supply nitric oxide 48, oxygen 47, or oxygen 47 and NO 48 to the RBCs in advance of transfusion to a recipient 50. System 25 can contain all or a combination of such devices 4000 through 9000 in varying configurations. System 25 may also contain devices 100 through 1600 as discussed above.

Components of system 25 are connected in a conventional fashion. Tube 440 connects collection bag 35 with leukoreduction filter 400. Tube 441 connects solution bag 250 with collection bag 35. Tube 442 connects plasma bag 45 with collection bag 35. Tube 443 connects leukoreduction filter 4000 with a depletion device 100 of the present disclosure. Tube 444 connects depletion device 100 with blood storage bag 2000. Blood storage system 25 is preferably a single-use, disposable, low cost system.

System components, namely, leukoreduction filter 4000, editing device 5000, irradiation device 6000, pathogen inactivation device 7000, volume reduction device 8000 and nitric oxide device 9000, perform various therapies for the RBCs prior to transfusion. Depending upon the therapies, such therapies are performed on RBCs before passage through a depletion device 20 of the present disclosure, or after storage in storage bag 36. After being depleted in a depletion device 20, RBCs are maintained in an oxygen, carbon dioxide, or oxygen and carbon dioxide depleted environment 27 to ensure the desired results for the patient and to avoid morbidity commonly associated with transfusions using stored RBCs.

Additional non-limiting examples of blood storage systems incorporating the depletion devices and gas addition devices of the present disclosure may be found in U.S. application Ser. No. 13/541,554, filed Jul. 3, 2012, entitled "System for Extended Storage of Red Blood Cells and Methods of Use," hereby incorporated by reference in its entirety.

Each periodical, patent, and other document or reference cited herein is herein incorporated by reference in its entirety.

Having now generally described the invention, the same will be more readily understood through reference to the following examples that are provided by way of illustration, and are not intended to be limiting of the present invention, unless specified.

EXAMPLES

Example 1: Rigid Enclosure, Single Liquid Chamber, Dual Depletion Chamber Device FIGS. 1A, 1B and 1C depict a rigid enclosure depletion device 100 with a single liquid chamber 101 and two depletion chambers 102. The two depletion chambers 102 are formed by rigid enclosure outer shells 103 and gas permeable barriers 107. The single liquid chamber 101 is formed by inner shell 109 and gas permeable barriers 107 and has an inlet 104 and an outlet 105. Depletion chambers 102 contain depletion media 106. Gas permeable barriers 107 separate the single liquid chamber 101 and two depletion chambers 102.

As blood enters the single liquid chamber 101 through the inlet 104, it is exposed to an oxygen depleted environment created by depletion media 106 in depletion chambers 102 where depletion media 106 is a solid $O_2$ and $CO_2$ sorbent combination. This causes the red blood cells to release oxygen and carbon dioxide into the gas depleted environment of depletion chambers 102. The oxygen and carbon dioxide diffuse through the gas permeable barriers 107. The increase in $O_2$ and $CO_2$ gases in the gas depleted environment causes a reaction in the depletion media 106 that removes this added oxygen and carbon dioxide from the environment. Oxygen and carbon dioxide depletion media 106 are depicted as a rectangular package present in depletion chambers 102, though several packets of oxygen and carbon dioxide depletion media 106, separate or combined, could be placed in each chamber or a single longer packet of oxygen and carbon dioxide depletion media 106 could be used.

The liquid chamber 101 contains flow control features 108 that direct the flow of liquid against the gas permeable barriers 107. This directed flow both mixes and minimizes the distance between individual red cells and the gas permeable barriers 107. The flow control features 108 are depicted as approximately one-half the height of the blood chamber 101 (FIG. 1B). This ratio may be altered for different flow rates. The number and position of flow control features 108 can also be altered to optimize the process for a specific configuration. The oxygen and carbon dioxide depletion process continues during the exposure of the liquid containing red blood cells in liquid chamber 101 until the cells and liquid are oxygen and carbon dioxide depleted to the desired level and exit through outlet 105. The degree of oxygen and carbon dioxide depletion is controlled by the height, length and width of the device, the time that the liquid is in the chamber and the flow rate through the chamber. Although depicted with the inlet 104 at the top and outlet 105 at the bottom, the orientation can be reversed to control the flow into and out of liquid chamber 101.

Example 2: Rigid Enclosure, Dual Liquid Chamber, Three Depletion Chamber Device

FIGS. 3A, 3B and 3C depict a rigid enclosure depletion device 300 with two liquid chambers 101 and three depletion chambers 102. The two outer depletion chambers 102 are formed by the gas barrier enclosure outer shells 103. The inner depletion chamber 102 is formed by the enclosure shell 110. The two liquid chambers 101 are formed by outer enclosure shells 109 and have inlets 104 and outlets 105. Depletion chambers 102 contain oxygen and carbon dioxide depletion media 106. Gas permeable barriers 107 separate the two liquid chambers 101 and three depletion chambers 102. As liquid enters the liquid chamber 101 through an inlet 104, it is exposed to an oxygen and carbon dioxide depleted environment created by oxygen and carbon dioxide depletion media 106. This causes red blood cells in the liquid to release oxygen and carbon dioxide into the oxygen and carbon dioxide depleted environment. The oxygen and carbon dioxide gases diffuse through the gas permeable barriers 107. The increase in oxygen and carbon dioxide in the gas depleted environment results in a reaction with the oxygen and carbon dioxide depletion media 106 that removes this added gas from the environment. This process continues during the exposure of the red blood cells in the liquid until the cells are oxygen and carbon dioxide depleted to a desired level and exit through outlet 105. Although depicted with an inlet 104 and an outlet 105 at the top and an inlet 104 and an outlet 105 at the bottom connected, the orientation can be reversed to control the flow into and out of liquid chambers 101. The liquid chambers could also be connected in parallel with both inlets and both outlets at the same end of the device. A "stacked" depletion device 300 replicates all the features and capabilities of depletion device 100 shown in FIGS. 1A, 1B and 1C. Stacking the design combined with altering the internal features and ratios of the blood chamber 109 and the control features 108 can be continued creating as many layers as required to meet the oxygen and carbon dioxide depletion process requirements.

Example 3: Flexible Enclosure, Rigid Liquid Chamber, Dual Depletion Chamber Device FIGS. 4A-C depict flexible enclosure gas depletion device 400 having a single liquid chamber 101 and having two depletion chambers 102. The two depletion chambers 102 are each formed by gas permeable barrier 107 and flexible shell 129. The single liquid chamber 101 has an inlet 104 and outlet 105 in rigid inner shell 109. Rigid inner shell 109 includes flow control features 108. Depletion chambers 103 contain depletion media 106.

As liquid containing red blood cells enters the single liquid chamber 101 through the inlet 104, it is exposed to a gas depleted environment created by oxygen and carbon dioxide depletion media 106 through gas permeable barriers 107. This causes the red blood cells to release oxygen and carbon dioxide into the gas depleted environment. Oxygen and carbon dioxide diffuse through the gas permeable barriers 107. The increase in oxygen and carbon dioxide in the depletion chamber causes a reaction with the oxygen and carbon dioxide depletion media 106 that removes this added oxygen and carbon dioxide from the environment. Oxygen and carbon dioxide depletion media 106 is depicted in a rectangular package in the center of depletion chambers 102. Several packets of oxygen and carbon dioxide depletion media 106 could be placed in each chamber or a single longer packet of oxygen and carbon dioxide depletion media 106 could be used. The oxygen and carbon dioxide media 106 could be included as separate packets. The configuration of the packet and the chemistry contained in the oxygen and carbon dioxide depletion media 106 could be different for each depletion chamber 102 to optimize performance. The oxygen and carbon dioxide depletion process continues during the exposure of the red blood cells in liquid chamber 101 until the red blood cells and liquid are oxygen and carbon dioxide depleted to the desired level and exit through outlet 105. The degree of oxygen and carbon dioxide depletion is controlled by the height and length of the device, the time that the blood is in the chamber or the flow rate through the chamber and the width of the blood chamber. Although depicted with the inlet 104 at the top and outlet 105 at the bottom, the orientation can be reversed to control the flow into and out of liquid chamber 101.

Example 4: Flexible Enclosure, Single Liquid Chamber, Dual Depletion Chamber Device FIGS. 5A, 5B and 5C depict a flexible enclosure gas depletion device 500 with a single liquid chamber 101 and two depletion chambers 102. As depicted in FIG. 5A, the flexible enclosure may provide, but does not require, expansion or inflation of the device as liquid flows through the liquid chamber 101. The two depletion chambers 102 are formed by the gas barrier outer films forming flexible shell 129. The single liquid chamber 101 has an inlet 104 and an outlet 105. Depletion chambers 102 contain oxygen and carbon dioxide depletion media 106. Gas permeable barriers 107 separate the single liquid chamber 101 and two depletion chambers 102.

As liquid containing red blood cells enters the single liquid chamber 101 through the inlet 104, it is exposed to a gas depleted environment created by oxygen and carbon dioxide depletion media 106. This causes the red blood cells to release oxygen and carbon dioxide into the gas depleted environment. Oxygen and carbon dioxide diffuse through the gas permeable barriers 107. The increase in oxygen and carbon dioxide in the depletion chamber causes a reaction with the oxygen and carbon dioxide depletion media 106 that removes this added oxygen and carbon dioxide from the environment. Oxygen and carbon dioxide depletion media 106 is depicted in a rectangular package in the center of depletion chambers 102. Several packets of oxygen and carbon dioxide depletion media 106 could be placed in each chamber or a single longer packet of oxygen and carbon dioxide depletion media 106 could be used. The oxygen and carbon dioxide media 106 could be included as separate packets. The configuration of the packet and the chemistry contained in the oxygen and carbon dioxide depletion media 106 could be different for each depletion chamber 102 to optimize performance. The liquid chamber 101 is depicted without flow control features 108, though flow control features could be incorporated, for example as provided in Example 5. The oxygen and carbon dioxide depletion process continues during the exposure of the red blood cells in liquid chamber 101 until the red blood cells and liquid are oxygen and carbon dioxide depleted to the desired level and exit through outlet 105. The degree of oxygen and carbon dioxide depletion is controlled by the height and length of the device, the time that the blood is in the chamber or the flow rate through the chamber and the width of the blood chamber. Although depicted with the inlet 104 at the top and outlet 105 at the bottom, the orientation can be reversed to control the flow into and out of liquid chamber 101.

Example 5: Flexible Enclosure, Single Liquid Chamber, Dual Depletion Chamber Device FIGS. 6A-C depict a flexible enclosure gas depletion device 600 with a single liquid chamber 101 and two depletion chambers 102. The two depletion chambers 102 are formed by gas barrier outer films to form flexible shell 129. The single liquid chamber 101 has a liquid inlet 104 and a liquid outlet 105. Depletion chambers 102 contain oxygen and carbon dioxide depletion media 106. Gas permeable barriers 107 separate the single liquid chamber 101 and two depletion chambers 102.

As liquid containing red blood cells enters the single liquid chamber 101 through the inlet 104, it is exposed to a gas depleted environment created by oxygen and carbon dioxide depletion media 106. This causes the red blood cells to release oxygen and carbon dioxide into the gas depleted environment. Oxygen and carbon dioxide diffuse through the gas permeable barriers 107. The increase in oxygen and carbon dioxide in the depletion chamber causes a reaction with the oxygen and carbon dioxide depletion media 106 that removes this added oxygen and carbon dioxide from the environment. Oxygen and carbon dioxide depletion media 106 is provided as described above. The liquid chamber 101 is provided with an indirect path 133 for the flow of liquid produced by bonding the gas permeable barriers 107 together in a manner that would direct the flow of blood along a controlled path in the gas permeable barriers 107. This directed flow mixes and minimizes the distance between individual red blood cells and the gas permeable barriers 107. The oxygen and carbon dioxide depletion process continues during the exposure of the red blood cells in liquid chamber 101 until the red blood cells and liquid are oxygen and carbon dioxide depleted to the desired level and exit through outlet 105. The degree of oxygen and carbon dioxide depletion is controlled by the height and length of the device, the time that the blood is in the chamber or the flow rate through the chamber and the width of the blood chamber. Although depicted with the inlet 104 at the top and outlet 105 at the bottom, the orientation can be reversed to control the flow into and out of liquid chamber 101.

Example 6: Flexible Enclosure, Dual Liquid Chamber, Triple Depletion Chamber Device FIGS. 7A, 7B and 7C depict a flexible enclosure depletion device 700 with two liquid chambers 101 and three depletion chambers 102. The two outer depletion chambers 102 are formed by the gas barrier outer films forming flexible shell 129. The inner depletion chambers 102 are formed by sealing the center two gas permeable barriers 107 at the edges. The two liquid chambers 101 are formed by sealing the outer two gas permeable barriers 107 to the inner two gas permeable barriers 107 at the outer edges with inlets 104 and outlets 105. Oxygen and carbon dioxide depletion chambers 102 contain oxygen and carbon dioxide depletion media 106. Gas permeable barriers 107 separate the two liquid chambers 101 and three depletion chambers 102. As liquid having red blood cells enters liquid chamber 101 through an inlet 104, it is exposed to an oxygen and carbon dioxide depleted environment created by oxygen and carbon dioxide depletion media 106. This causes the red blood cells to release oxygen and carbon dioxide into the oxygen and carbon dioxide depleted environment. Oxygen and carbon dioxide gases diffuse through the gas permeable barriers 107. The increase in oxygen and carbon dioxide in the gas depleted environment causes a reaction in the oxygen and carbon dioxide depletion media 106 that removes these added gases from the environment. Liquid chambers 101 are depicted without flow control features. Flow control features can be formed by bonding the gas permeable barriers 107, for example as illustrated in FIGS. 6A-C. The depletion process continues during the exposure of the red blood cells until the cells are oxygen and carbon dioxide depleted to a desired level and exit through outlet 105. Although depicted with the inlet 104 and outlet 105 at the top and the inlet 104 and outlet 105 at the bottom connected, the orientation can be reversed to control the flow into and out of liquid chambers 101. The liquid chambers 101 could also be connected in parallel with both inlets and both outlets at the same end of the device.

This stack design replicates all the features and capabilities of depletion device 500 shown in FIGS. 3A, 3B and 3C. Similar features and capabilities of depletion device 600 can be incorporated into a stacked design of device 700. Stacking the design combined with altering the internal features can create as many layers as required to meet the oxygen and carbon dioxide depletion process requirements.

Example 7. Flexible Enclosure, Single Liquid Chamber, Dual Depletion Chamber Device FIGS. 8A, 8B and 8C depict a rigid enclosure depletion device 800 with a single liquid chamber 101 and two depletion chambers 115. The two depletion chambers 115 are formed by rigid enclosure outer shells 103 that are gas impermeable. The single liquid chamber 101 is formed by inner shell 109 and has an inlet 104 and an outlet 105. Oxygen and carbon dioxide depletion chambers 115 are formed by gas barrier outer enclosure shells 103 having gas inlets 111 and gas outlets 112 through which depletion gas 114 enters and exits the device and gas permeable barriers 107. Gas permeable barriers 107 separate the single liquid chamber 101 and two depletion chambers 115.

As blood enters the single liquid chamber 101 through the inlet 104, it is exposed to a gas depleted environment created by a depletion gas 114 entering the gas inlets 111. The depletion gas 114 may be either oxygen free or oxygen and carbon dioxide free. An oxygen and carbon dioxide free depletion gas 114 causes the red blood cells to release oxygen and carbon dioxide into the oxygen and carbon dioxide depleted environment. The oxygen and carbon dioxide gases diffuse through the gas permeable barriers 107. The increased oxygen and carbon dioxide in the depletion environment mixes with the depletion gas 114 and exits through gas outlet 112. The flow of gas removes the added oxygen and carbon dioxide from the environment of depletion chamber 102. Although depicted with the gas inlets 111 at the top and gas outlets 112 at the bottom, the orientation can be reversed to control the flow into and out of oxygen depleted chambers 115. Oxygen free or oxygen and carbon dioxide depletion gases are not depicted. Several gases including, but not limited to, argon, helium, and nitrogen are used. The configuration of the gas and the flow rate may be different for each depletion chamber 102 to optimize performance. Depletion chambers 115 formed by gas barrier outer shells 103 contain gas flow control features 113. These flow control features 113 are depicted as two horizontal bars. These features increase the mixing of the released oxygen with the depletion gas 114. Different configurations can be used depending on the gas and flow rate selected.

The liquid chamber 101 contains flow control features 108 as described above. The gas depletion process continues during the exposure of the red blood cells in liquid chamber 101 until the cells are gas depleted to the desired level and exit through outlet 105. The degree of gas depletion is controlled by the height and length of the device, the time that the liquid containing red blood cells is in the chamber, the flow rate through the chamber and the width of the liquid chamber. Although depicted with the inlet 104 at the top and outlet 105 at the bottom, the orientation can be reversed to control the flow into and out of liquid chamber 101.

Example 8. Rigid Enclosure, Dual Liquid Chamber, Triple Gas Depletion Chamber Device FIGS. 9A, 9B and 9C depict a rigid enclosure depletion device 900 with two liquid chambers 101 and gas depletion chambers 115. The two gas depletion chambers 115 are formed by gas barrier outer shells 103. The two liquid chambers 101 are formed by inner shells 109 and have inlets 104 and outlets 105. The two outer gas depletion chambers 115 formed by gas barrier outer shells 103 have gas inlets 111 and gas outlets 112. The inner depletion chamber 115 is formed by the gas barrier enclosure shell 110. Gas permeable barriers 107 separate the two liquid chambers 101 and three gas depletion chambers 115.

As liquid containing red blood cells enters the liquid chambers 101 through an inlet 104, it is exposed to a gas depleted environment created by oxygen free or oxygen and carbon dioxide free gas entering the gas inlets 111 as provided for device 800 above. Although depicted with an inlet 104 and an outlet 105 at the top and an inlet 104 and an outlet 105 at the bottom connected, the orientation can be reversed to control the flow into and out of liquid chambers 101. A depletion device 900 provides for the serial depletion of a liquid flowing through the device. Additional gas depletion chambers 115 and liquid chambers 101 can readily be added. The chambers could also be connected in parallel with both inlets and both outlets at the same end of the device.

The gas depletion process continues during the exposure of the red blood cells in liquid chamber 101 until the cells are gas depleted to the desired level and exit through outlets 105. The degree of gas depletion is controlled by the height and length of the device, the time that the liquid is in the chamber or the flow rate through the chamber and the width of the liquid chamber.

Example 9. Rigid Enclosure, Dual Liquid Chamber, Triple Gas Depletion Chamber Device FIGS. 10A, 10B and 10C depict a rigid enclosure depletion device 1000 with two liquid chambers 101 and gas depletion chambers 115 similar to depletion device 900 above except that the red blood cell containing fluid flows in parallel rather than in series. The two gas depletion chambers 115 are formed by gas barrier outer shells 103. The two liquid chambers 101 are formed by inner shells 109 and have inlets 104 and outlets 105. In device 1000, the flow of liquid is split to two or more inlets 104 by splitter 130 and the flow of depleted liquid is combined after exiting from outlet 105 by joiner 131. Operation of the devices is as described above in Example 8.

Example 10. Rigid Enclosure, Single Liquid Chamber, Single Depletion Chamber Plasma Separation Device FIGS. 12A, 12B and 12C depict a rigid enclosure depletion device 1200 with a single liquid chamber 101, a depletion chamber 102, and a plasma/platelet chamber 127. The depletion chamber 102 is formed by rigid enclosure outer shells 103 and a gas permeable barrier 107. The single liquid chamber 101 is formed by inner shell 109 and gas permeable barrier 107 and plasma porous hydrophobic membrane 124. Depletion device 1200 has an inlet 104 and an outlet 105. Depletion chamber 102 contains depletion media 106. Gas permeable barrier 107 separates the single liquid chamber 101 and depletion chamber 102. Depletion device 1200 also has a plasma chamber 127 formed from plasma outer shell 119 and plasma porous hydrophilic membrane 124 and an anaerobic plasma port 116.

As blood enters the single liquid chamber 101 through the inlet 104, it is exposed to an oxygen depleted environment created by depletion media 106 in depletion chamber 102 where depletion media 106 is a solid $O_2$ and $CO_2$ sorbent combination. This causes the red blood cells to release oxygen and carbon dioxide into the gas depleted environment of depletion chambers 102, resulting in the diffusion of oxygen and carbon dioxide from the liquid chamber 101 through the gas permeable barrier 107. Gas depletion proceeds as for the devices described in the examples above. Also as provided in the examples above, the liquid chamber 101 contains flow control features 108.

The liquid chamber 101 further contains a plasma porous hydrophilic membrane 124 separating liquid chamber 101 from plasma chamber 127. Anaerobic plasma passes through the plasma porous hydrophilic membrane 118 into plasma chamber 127 and the anaerobic plasma 120 exits through anaerobic plasma port 116. Flow of anaerobic plasma through plasma porous hydrophilic membrane 127 and into anaerobic plasma chamber 127 is controlled by a pressure differential between liquid chamber 101 and plasma chamber 127. Increased pressure in liquid chamber 101 relative to the pressure of plasma chamber 117 results in an increase in plasma flow through plasma porous hydrophilic membrane 124 and into anaerobic plasma chamber 127.

Example 11: Rigid Enclosure, Single Liquid Chamber, Dual Depletion Chamber, Plasma Separation Device FIGS. 13A, 13B and 13C depict a rigid enclosure depletion device 1300 with a single liquid chamber 101 and two depletion chambers 102 and 122. A first depletion chamber 102 is formed by rigid enclosure outer shells 103 and a gas permeable barrier 107. A second depletion chamber 122 is formed by outer shell 103 and a gas permeable barrier 107. The single liquid chamber 101 is formed by inner shell 109, gas permeable barrier 107, and plasma porous hydrophobic membrane 124. Depletion device 1300 and has an inlet 104 and an outlet 105. Depletion chamber 102 and depletion chamber 122 contain depletion media 106. A gas permeable barrier 107 separates a single liquid chamber 101 and depletion chamber 102 and a gas permeable barrier 107 separates plasma chamber 117 from depletion chamber 122. Depletion device 1300 also has a plasma chamber 117 formed from plasma outer shell 119, plasma porous hydrophilic membrane 124, and gas permeable barrier 107. Plasma chamber 117 has anaerobic plasma port 116.

As blood enters the single liquid chamber 101 through the inlet 104, it is exposed to an oxygen depleted environment created by depletion media 106 in depletion chamber 102 where depletion media 106 is a solid $O_2$ and $CO_2$ sorbent combination. Gas depletion proceeds as provided in the examples above.

The liquid chamber 101 further contains a plasma porous hydrophilic membrane 124 separating liquid chamber 101 from plasma chamber 117. Gas depleted plasma passes through the plasma porous hydrophilic membrane 124 into anaerobic plasma chamber 117 and the anaerobic plasma 120 exits through anaerobic plasma port 116. The plasma in plasma chamber 117 is separated from a second depletion chamber 122 which provides for further removal of $O_2$ and $CO_2$ (depending on depletion media 106). Flow of anaerobic plasma through plasma porous hydrophilic membrane 124 and into anaerobic plasma chamber 117 is controlled by a pressure differential between liquid chamber 101 and plasma chamber 117. Increased pressure in liquid chamber 101 relative to the pressure of plasma chamber 117 results in an increase in plasma flow through plasma porous hydrophilic membrane 124 and into anaerobic plasma chamber 117.

Example 12: Combined Leukoreduction and Gas Depletion Device

Figure 14A:
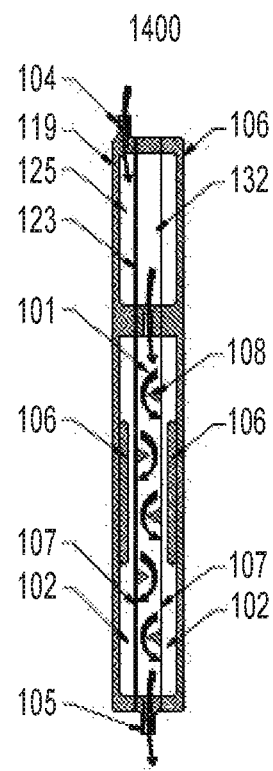
FIGS. 14A-C illustrate an exemplary depletion device having a leukoreduction filter, two depletion chambers and a fluid chamber according to the present disclosure.
Figure 14B:
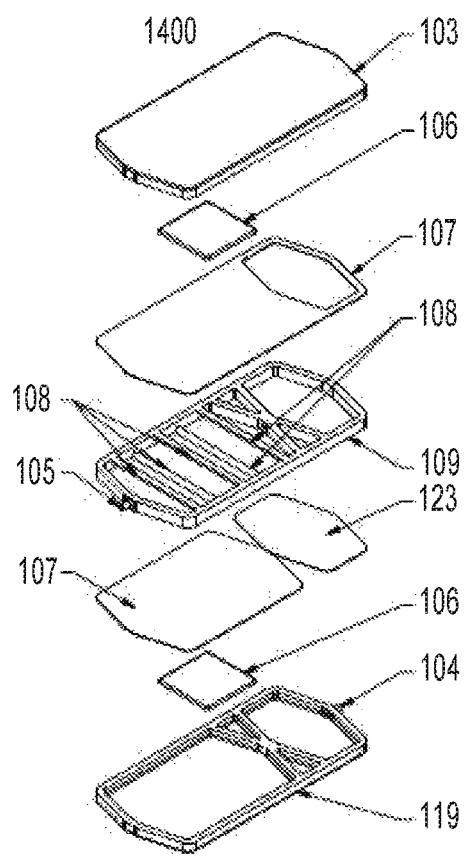
Figure 14C:
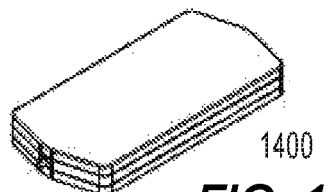

FIGS. 14A, 14B and 14C depict a combination depletion device 1400 having a leukoreduction media 123, a leukoreduction chamber 125, a leukoreduced fluid chamber 132, a liquid chamber 101 and two depletion chambers 102. The combination depletion device 1400 includes a liquid inlet 104 and liquid outlet 105. As provided in the examples above, depletion chambers 102 have depletion media 106 to provide for an oxygen free and carbon dioxide free environment.

As plasma reduced blood enters through liquid inlet 104, the fluid passes through leukoreduction media 123 which binds to or adsorbs white blood cells present in the blood. Upon passing through leukoreduction media 123, the fluid enters leukoreduction chamber 125 and flows to depletion chamber 102 having flow control features 108. As provided in the examples above, the blood is depleted of oxygen and carbon dioxide and flows out through liquid outlet 105.

As shown in FIG. 14A, leukoreduction media 123 is provided in a membrane form. In alternate configurations, the leukoreduction media 123 may be provided as a matrix through which the liquid flows. In this alternate configuration, leukoreduction chamber 123 and leukoreduced fluid chamber 132 may be combined and filled with a leukoreduction media 123 matrix.

Figure 15A:
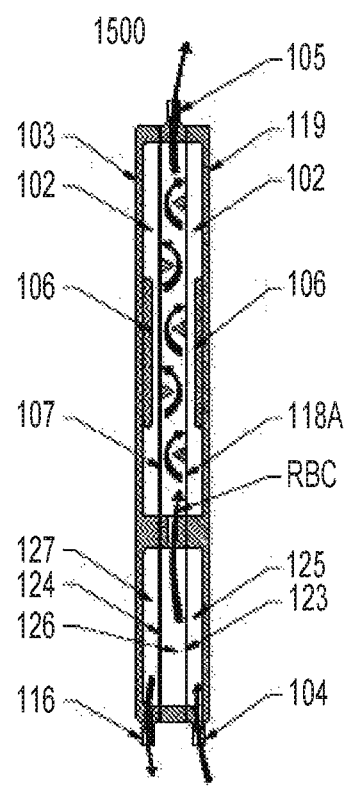
FIGS. 15A-C illustrate an exemplary depletion device having a leukoreduction filter, a plasma separation chamber, two depletion chambers and a fluid chamber according to the present disclosure.
Figure 15B:
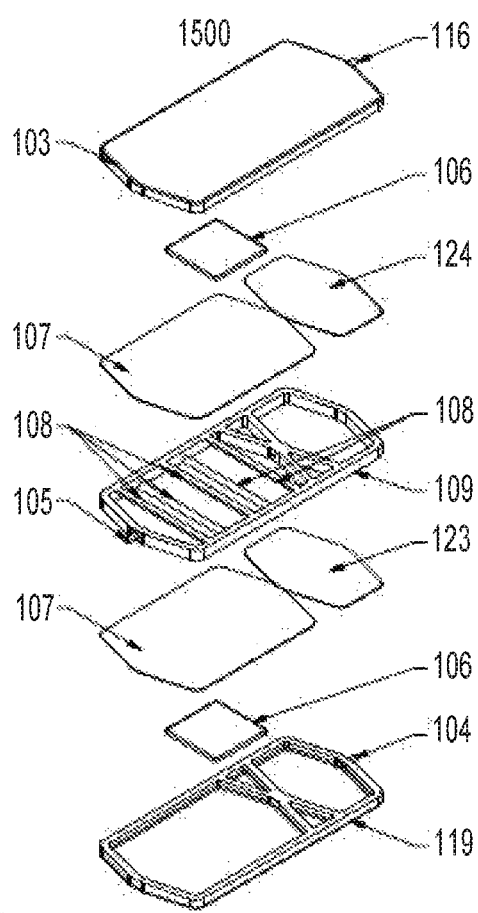
Figure 15C:
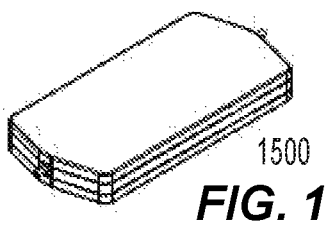

Example 13: Combined Leukoreduction, Gas Depletion, and Plasma Separation Device FIGS. 15A, 15B and 15C depict a combination depletion device 1500 having a leukoreduction media 123, a leukoreduction chamber 125, a plasma separation chamber 126, a liquid chamber 101 and two depletion chambers 102. The combination depletion device 1500 includes a liquid inlet 104 and liquid outlets 105 and 106. The depletion chambers 102 having depletion media 106 and flow control features 108 are as provided in the examples above.

As whole blood enters through liquid inlet 104, the fluid passes through leukoreduction media 123 which binds to, or adsorbs, white blood cells present in the blood. Upon passing through leukoreduction media 123, the fluid enters plasma separation chamber 126. As provided above, leukoreduction media 123 may be provided either as a membrane or a matrix of leukoreduction media. Plasma and platelets flow through the plasma porous hydrophobic membrane 124 into plasma/platelet chamber 127. The plasma and platelets flow from the chamber through 116 to a plasma and platelet collection bag (not shown). The now leukocyte/plasma/platelet depleted fluid having red blood cells flows into depletion chamber 102 and is depleted of oxygen and carbon dioxide in the manner described above. Anaerobic red blood cells flow out through liquid outlet 105 and are collected and stored in an anaerobic storage bag.

Example 14: Reoxygenation Device

FIGS. 16A, 16B and 16C depict a reoxygenation device 1600 according to the present disclosure having a gas addition chamber 134, separated by gas permeable barrier 107, and liquid chamber 101 formed by two gas permeable barriers 107.

An oxygen (or oxygen and carbon dioxide) depleted blood product enters through liquid inlet 104 and passes through liquid chamber 102 where it is supplied with oxygen through gas permeable barriers 107. As shown, ambient air is provided through gas addition ports 128. Oxygen diffuses from gas addition chambers 134, through gas permeable barriers 107 and is absorbed by the hemoglobin in the red blood cells. In some embodiments, addition ports 128 provide for an oxygen rich gas source to flow into the gas addition chamber 134. Any suitable gas may be provided to a gas addition device through addition port 128 including ambient air, pure oxygen and mixtures of oxygen and carbon dioxide and may further comprise NO, either together with $O_2$ or provided separately.

Example 15: Depletion of Oxygen in a Red Blood Cell Suspension Using a Single Cassette Configuration Oxygen is depleted in a red blood cell suspension using a device having a flexible enclosure, single liquid chamber, and dual depletion chamber (single cassette configuration). Deoxygenation of a red blood suspension is tested with a device of the present disclosure constructed from acrylic blocks machined with a sinuous path profile design described in FIGS. 6A, 6B, and 6C. Gas permeable barrier 107 is provided by a hydrophobic membrane (GVSP22205, Millipore, Billerica, Mass.). The membrane is attached to the sinuous path using Arrow AP10-4 all-purpose hot melt glue (Arrow Fastener Co., Saddle Brook, N.J.). Depletion media 106 is provided by a flushing gas (100% $N_2$). Table 1 summarizes the path geometries of three prototype devices tested. All devices have the same path length of 2235 mm and exposed surface area of 90 $cm^2$.

Two flow-through cell oxygen sensors ("cell"), are placed in series with the device, one upstream of inlet 104 and another downstream of outlet 105. The cell sensors comprise a PreSens Fibox 3 trace device running PreSens Fibox 3 trace PSt6 software (PST6v701) and an pST3 oxygen probe for in-line measurement (PreSens—Precision Sensing GmbH). Two dipping probe oxygen sensors ("probe") are provided in series with liquid chamber 101 inside flexible shell 129, one directly downstream of inlet 104 and another directly upstream of outlet 105. The probe sensors comprise a PreSens OXY-4 mini device running PreSens OXY-4 mini software (OXY4v2_30fb) and a PSt6 oxygen dipping probe sensor (PreSens—Precision Sensing GmbH). These sensors monitor partial pressures of oxygen in the fluid suspension having red blood cells at different positions along the flow path.

In this example, a red blood suspension flows through the sensor-liquid chamber assembly once. Table 2 summarizes the results of the deoxygenation process in the different prototype devices. All tests are performed at room temperature. The average partial pressure of oxygen in the red blood suspension measured by an inlet sensor is $pO_{2\ in}$. The average partial pressure of oxygen in the red blood suspension measured by an outlet sensor is $pO_{2\ out}$. The change in oxygen level ($\Delta pO_2$) is calculated by taking the difference between $pO_{2\ in}$ and $pO_{2\ out}$. The percentage of oxygen reduction (% $O_2$ reduction) is calculated by dividing $\Delta pO_2$ by $pO_{2\ in}$.

The exposed surface area to path volume ratio is observed to affect the efficiency of oxygen reduction. At the flow rate of 1 ml/min, prototype device A provides the highest percentage of oxygen reduction out of the three devices. An effect of flow rates on the efficiency of oxygen depletion is also observed in prototype device B. Out of three flow rates (1 ml/min, 1.2 ml/min, and 1.4 ml/min), the highest percentage of oxygen reduction is observed at 1 ml/min.

Probe sensors consistently measure higher percentage of oxygen reduction compared to cell sensors plausibly due to their relative positioning to the flexible shell 129 or possibly due to non-homogeneity of the fluid.

TABLE 1

Flow Path Geometries

| Device ID | Path Depth (mm) | Path Length (mm) | Path Volume (ml) | Exposed Surface Area (cm$^2$) |
|---|---|---|---|---|
| A | 0.5 | 2235 | 4.5 | 90 |
| B | 1 | 2235 | 8.9 | 90 |
| C | 2 | 2235 | 17.9 | 90 |

TABLE 2

Measurements of Oxygen Level

| Device ID | Sensor Type | Flow Rate (ml/min) | Processing Time (min) | pO$_2$ $_{in}$ (Torr) | pO$_2$ $_{out}$ (Torr) | ΔpO$_2$ (Torr) | % O$_2$ Reduction |
|---|---|---|---|---|---|---|---|
| A | Cell | 1 | 4.5 | 12.0 | 2.7 | 9.3 | 78 |
| A | Probe | 1 | 4.5 | 11.2 | 1.5 | 9.7 | 87 |
| B | Probe | 1 | 8.9 | 26 | 5 | 21 | 81 |
| B | Cell | 1.2 | 7.4 | 18 | 10 | 8 | 44 |
| B | Probe | 1.2 | 7.4 | 18 | 4 | 14 | 78 |
| B | Cell | 4.1 | 2.2 | 18 | 9 | 9 | 50 |
| B | Probe | 4.1 | 2.2 | 17 | 4 | 13 | 76 |
| C | Probe | 1 | 17.9 | 20 | 12 | 8 | 40 |

Example 16: Depletion of Oxygen in a Red Blood Cell Suspension Using Multiple Devices Connected in Series Devices having path geometries described in Table 1 are constructed as described in Example 15. Three devices having the same path depth are connected in series to produce a test set. Table 3 summarizes the overall path geometries for each test set. Each set of devices have in total the same path length of 6705 mm and exposed surface area of 269 cm$^2$.

Two dipping probe oxygen sensors ("probe") are provided in series with liquid chamber 101 inside flexible shell 129 of a first device in the series, one directly downstream of inlet 104 and another directly upstream of outlet 105. The probe sensors are as described above in example 15. Additionally, two dipping probe oxygen sensors ("probe") are provided in series with liquid chamber 101 inside flexible shell 129 of a third device in the series, one directly downstream of inlet 104 and another directly upstream of outlet 105. These sensors monitor partial pressures of oxygen in blood at different positions along the flow path.

Oxygen saturation levels and partial pressures of oxygen in a red blood cell suspension are also tested both pre- and post-processing. An aliquot of the red blood cell suspension is taken via a syringe before and after processing and is analyzed in an oxygen analyzer ("Nova COOX"; Nova Analytical Systems, Niagara Falls, N.Y.).

In this example, a red blood cell suspension flows through a test set once. Table 4 summarizes the results of the deoxygenation process in the different test sets. All tests are performed at temperatures between 22.0 to 23.6° C. The average partial pressure of oxygen in blood measured by the inlet sensor in a first device of the test set is pO$_2$ $_{d1in}$. The average partial pressure of oxygen in blood measured by the outlet sensor in a third device of the test set is pO$_2$ $_{d3out}$. The change in oxygen level (ΔpO$_2$) is calculated by taking the difference between pO$_2$ $_{d1in}$ and pO$_2$ $_{d3out}$. The percentage of oxygen reduction (% O$_2$ reduction) is calculated by dividing ΔpO$_2$ by pO$_2$ $_{d1in}$. Table 5 compares the measured % SO$_2$ at 37° C. with calculated % SO$_2$ values based on the pO$_2$ measurements at both 23° C. and 37° C. The conversion calculation is made based on the Hill Equation:

$$\% \ SO_2 = \frac{(pO_2)^n}{(pO_2)^n + (P_{50})^n} \times 100\%$$

where n=2.7 represents the cooperativity of oxygen binding to hemoglobin, and P$_{50}$ represents the partial pressure at which hemoglobin is half-saturated at either 23° C. or 37° C. The measured or calculated oxygen saturation of the red blood cell suspension before and after the deoxygenation are % SO$_2$ $_{in}$ and % SO$_2$ $_{out}$, respectively.

At a flow rate of 1.10 ml/min, a test set comprising three prototype B devices provides the highest percentage of oxygen reduction out of the three sets, achieving 91.5% oxygen reduction. Slower flow rates are consistently observed to result in a greater percentage oxygen reduction compared to faster flow rates in all test sets. At a flow rate of 1.10 ml/min, a red blood cell suspension sample that is processed with a test set comprising three prototype A devices is measured to have a 9.3% reduction in the saturated oxygen level at 37° C. using the Nova COOX system. However, the same blood sample is calculated to exhibit a 42.9% reduction in its oxygen saturation level based on the pO$_2$ measurements produced from the same system at 37° C. Not to be limited by theory, this may suggest that the cooperativity or the P$_{50}$ value in the Hill Equation model may not be optimized to reflect experimental results. Another discrepancy is observed between the post-processing pO$_2$ measurements made by the in-line probe sensor and the Nova COOX system. Not to be limited by theory, this may suggest that the red blood cell suspension sample aliquot is being re-oxygenated quickly during its transfer to the Nova COOX system.

TABLE 3

Flow Path Geometries for 3 Devices in Series

| Set ID | Path Depth (mm) | Path Length (mm) | Path Volume (ml) | Exposed Surface Area (cm$^2$) |
|---|---|---|---|---|
| A | 0.5 | 6705 | 13.4 | 269 |
| B | 1 | 6705 | 26.8 | 269 |
| C | 2 | 6705 | 53.7 | 269 |

TABLE 4

Measurements of Oxygen Level

| Set ID | Flow Rate (ml/min) | Processing Time (min) | pO$_2$ $_{d1in}$ (Torr) | pO$_2$ $_{d1out}$ (Torr) | pO$_2$ $_{d3in}$ (Torr) | pO$_2$ $_{d3out}$ (Torr) | ΔpO$_2$ (Torr) | % O$_2$ Reduction |
|---|---|---|---|---|---|---|---|---|
| A | 1.10 | 14.90 | 15.70 | 4.40 | 7.70 | 1.50 | 14.20 | 90.4 |
| A | 2.16 | 7.59 | 14.70 | 4.28 | 6.28 | 4.19 | 10.51 | 71.5 |

TABLE 4-continued

Measurements of Oxygen Level

| Set ID | Flow Rate (ml/min) | Processing Time (min) | $pO_{2\ d1in}$ (Torr) | $pO_{2\ d1out}$ (Torr) | $pO_{2\ d3in}$ (Torr) | $pO_{2\ d3out}$ (Torr) | $\Delta pO_2$ (Torr) | % $O_2$ Reduction |
|---|---|---|---|---|---|---|---|---|
| B | 1.10 | 29.64 | 18.30 | 8.08 | 9.10 | 1.56 | 16.74 | 91.5 |
| B | 3.98 | 8.19 | 20.87 | 12.73 | 8.31 | 8.05 | 12.82 | 61.4 |
| B | 4.50 | 7.24 | 15.60 | 12.14 | 9.12 | 8.61 | 6.99 | 44.8 |
| C | 1.03 | 57.77 | 18.64 | 8.50 | 10.91 | 7.14 | 11.50 | 61.7 |
| C | 2.10 | 28.33 | 18.05 | 8.71 | 11.24 | 7.73 | 10.32 | 57.2 |

TABLE 5

Comparison of $pO_2$ and $SO_2$ Measurements in Set A at 1.1 ml/min

| Measurement System | Test Temp. (° C.) | Measured $pO_{2\ d1in}$ (Torr) | Measured $pO_{2\ d3out}$ (Torr) | Calculated from $pO_2$ % $SO_{2\ in}$ | Calculated from $pO_2$ % $SO_{2\ out}$ | Measured % $SO_{2\ in}$ | Measured % $SO_{2\ out}$ |
|---|---|---|---|---|---|---|---|
| Probe | 23 | 15.70 | 1.50 | 64.9** | 0.3 | — | — |
| Nova COOX | 37 | 15.60 | 9.0 | 73.4** | 30.5 | 51.5 | 42.2 |

Example 17: Depletion of Oxygen in a Red Blood Cell Suspension by Re-Circulation in a Single Device Only prototype device B is tested in this example. The device is constructed as described in Example 15. The path geometry of the device is summarized in Table 1. The sensors are arranged as described in Example 15. The oxygen saturation levels are measured as described in Example 16.

In this example, a red blood cell suspension is re-circulated through the sensor-liquid chamber assembly for at least three passes. These devices are also tested in multiple orientations and gravity feed methods. Table 6 summarizes the results of the deoxygenation process at different flow rates and re-circulation cycles. All tests are performed at temperatures between 23.6 to 25.0° C. The average partial pressure of oxygen in blood measured by an inlet sensor during a single pass is $pO_{2\ in}$. The average partial pressure of oxygen in blood measured by an outlet sensor during a single pass is $pO_{2\ out}$. The change in oxygen level in a single pass ($\Delta pO_2$) is the calculated difference between $pO_{2\ in}$ and $pO_{2\ out}$ from the same pass measured for each type of sensors. The percentage of oxygen reduction in a single pass (% $O_2$ reduction (one pass)) is calculated by dividing $\Delta pO_2$ by $pO_{2\ in}$ from the same pass for each type of sensors. The overall percentage of oxygen reduction (overall % $O_2$ reduction (from start)) is calculated by dividing the difference between $pO_{2\ in}$ of the first pass and $pO_{2\ out}$ in the current pass by $pO_{2\ in}$ from the first pass for each type of sensors. The oxygen saturation of the red blood cell suspension before and after the deoxygenation are % $SO_{2\ in}$ at 37° C. and % $SO_{2\ out}$ at 37° C., respectively.

The flow rate affects the number of passes required to reduce oxygen down to a desired level. To achieve the same overall percentage oxygen reduction, it takes five passes at 8.4 ml/min compared to three passes at 5.1 ml/min. On the return pass through the device, the starting $pO_2$ level is higher than when the sample exited the device on the prior pass. Not to be limited by theory, this suggests that oxygen reduction in RBCs is not homogenous and diffusion from the RBC to the surrounding fluid takes place over time scales that are longer than the time necessary to remove the oxygen from the surrounding fluid. Alternatively, devices such as those FIGS. 3, 8, 9, 10, 13, and 15 may eliminate oxygen increases.

The observations of up to 94% reduction in the $pO_2$ levels suggests that the devices are effective in removing oxygen from red blood cell containing samples. The unchanged oxygen saturation levels observed in this Example demonstrate that deoxygenated red blood cell containing blood samples can be rapidly re-oxygenated upon removal from an anaerobic environment. Not to be limited by theory, this suggests that extra care needs to be taken when measuring $SO_2$ in the set up disclosed herein, given that hemoglobin has a very high affinity to oxygen. Such observations also support the understanding that a longer processing time is required for deoxygenation compared to re-oxygenation.

TABLE 6

Measurements of Oxygen Level

| Test No. | Flow Rate (ml/min) | Processing Time (min) | Pass No. | $pO_{2\ in}$ (Torr) Cell | $pO_{2\ in}$ (Torr) Probe | $pO_{2\ out}$ (Torr) Probe | $pO_{2\ out}$ (Torr) Cell | $\Delta pO_2$ (Torr) (one pass) Cell | $\Delta pO_2$ (Torr) (one pass) Probe | % $O_2$ Reduction (one pass) Cell | % $O_2$ Reduction (one pass) Probe | Overall % $O_2$ Reduction (from start) Cell | Overall % $O_2$ Reduction (from start) Probe | % $SO_{2\ in}$ at 37° C. | % $SO_{2\ out}$ at 37° C. |
|---|---|---|---|---|---|---|---|---|---|---|---|---|---|---|---|
| line 48 | 5.1 | 13 | 1 | 94.5 | 96.6 | 10.0 | 19.2 | 75.3 | 86.6 | 80 | 90 | 80 | 90 | 95.9 | 98.6 |
| | | | 2 | 62.7 | 60.6 | 18.2 | 17.0 | 45.7 | 42.4 | 73 | 70 | 82 | 81 | 98.6 | 98.1 |
| | | | 3 | 55.2 | 58.7 | 5.8 | 11.9 | 43.3 | 52.9 | 78 | 90 | 87 | 94 | 98.1 | 97.6 |

TABLE 6-continued

Measurements of Oxygen Level

| Test No. | Flow Rate (ml/min) | Processing Time (min) | Pass No. | $pO_2\ _{in}$ (Torr) Cell | $pO_2\ _{in}$ (Torr) Probe | $pO_2\ _{out}$ (Torr) Probe | $pO_2\ _{out}$ (Torr) Cell | $\Delta pO_2$ (Torr) (one pass) Cell | $\Delta pO_2$ (Torr) (one pass) Probe | % $O_2$ Reduction (one pass) Cell | % $O_2$ Reduction (one pass) Probe | Overall % $O_2$ Reduction (from start) Cell | Overall % $O_2$ Reduction (from start) Probe | % $SO_2\ _{in}$ at 37° C. | % $SO_2\ _{out}$ at 37° C. |
|---|---|---|---|---|---|---|---|---|---|---|---|---|---|---|---|
| line 64 | 8.4 | 10 | 1 | 97.9 | 101.8 | 21.1 | 24.2 | 73.7 | 80.7 | 75 | 79 | 75 | 79 | 98.8 | 98.2 |
| | | | 2 | 60.5 | 58.5 | 14.8 | 16.0 | 44.5 | 43.7 | 74 | 75 | 85 | 85 | 98.2 | 97.6 |
| | | | 3 | 48.5 | 49.3 | 14.0 | 15.0 | 33.5 | 35.3 | 69 | 72 | 85 | 86 | 97.6 | 97.3 |
| | | | 4 | 36.8 | 35.4 | 10.7 | 16.0 | 20.8 | 24.7 | 57 | 70 | 84 | 89 | 97.3 | 98.0 |
| | | | 5 | 31.3 | 33.3 | 7.9 | 14.4 | 16.9 | 25.4 | 54 | 76 | 85 | 92 | 98.0 | 97.3 |
| line 89 | 5.1 | 13 | 1 | 144.0 | 162.3 | 24.2 | 24.2 | 119.8 | 138.1 | 83 | 85 | 83 | 85 | 98.2 | 99.3 |
| | | | 2 | 82.5 | 82.6 | 12.8 | 18.9 | 63.6 | 69.8 | 77 | 85 | 87 | 92 | 99.3 | 99.0 |
| | | | 3 | 63.2 | 64.9 | 17.0 | 12.8 | 50.4 | 47.9 | 80 | 74 | 91 | 90 | 99.0 | 98.8 |

What is claimed is:

1. A gas addition device for adding gas to a blood product comprising:
   a. an enclosure;
   b. one or more liquid chambers;
      wherein said one or more liquid chambers further comprise one or more flow control features that disrupt laminar flow and wherein said one or more flow control features are half the height of said one or more liquid chambers and are the width of said one or more liquid chambers;
   c. two or more gas addition chambers;
   d. at least one gas permeable barrier separating at least one of said one or more liquid chambers from said two or more gas addition chambers;
   e. at least one liquid inlet; and
   f. at least one liquid outlet.

2. The gas addition device of claim 1, wherein said gas permeable barrier is a membrane comprising a polyolefin, polytetrafluoroethylene (PTFE), polyvinylidene mono- or di-fluoride (PVDF), a polysulfone, a silicone, an epoxy, a polyester membrane, or a ceramic.

3. The gas addition device of claim 2, wherein said at least one gas permeable barrier is a hydrophobic porous structure.

4. The gas addition device of claim 1, wherein said one or more liquid chambers are separated from said two or more gas addition chambers by more than one gas permeable barrier.

5. The gas addition device of claim 1, wherein said enclosure is prepared of a material selected from the group consisting of a rigid material, a flexible material, an elastic material, and combinations thereof.

6. The gas addition device of claim 1, wherein said liquid chamber is prepared of a material selected from the group consisting of a rigid material, a flexible material, an elastic material, and combinations thereof.

7. The gas addition device of claim 1, wherein said blood product is selected from the group consisting of whole blood, leukocyte depleted blood, leukocyte and platelet depleted blood, a red blood cell suspension, oxygen and carbon dioxide depleted red blood cells, oxygen depleted red blood cells, and plasma.

8. The gas addition device of claim 1, wherein said two or more gas addition chambers further comprise at least one gas inlet and at least one gas outlet in fluid communication with said two or more gas addition chambers.

9. The gas addition device of claim 8, wherein said gas addition chambers further comprise one or more gas flow control features.

10. The gas addition depletion device of claim 8, wherein an addition gas flows into said at least one gas inlet, through said two or more gas addition chambers and out through said one or more gas outlets.

11. The gas addition device of claim 10, wherein said addition gas is selected from the group consisting of pure oxygen, air, carbon dioxide, nitrous oxide and combinations thereof.

12. The gas addition device of claim 1, wherein said one or more liquid chambers is selected from the group consisting of one liquid chamber, two liquid chambers, three liquid chambers, four liquid chambers, five liquid chambers, and more than five liquid chambers.

13. The gas addition device of claim 1, wherein said two or more gas addition chambers is selected from the group consisting of two gas addition chambers, three gas addition chambers, four gas addition chambers, five gas addition chambers, and more than five gas addition chambers.

14. A method of preparing a blood product for transfusion comprising flowing a blood product liquid through a device according to claim 1 to prepare a blood product having an increased level of gas.

15. The method of claim 14, wherein said blood product is selected from the group consisting of whole blood, leukocyte depleted blood, leukocyte and platelet depleted blood, a red blood cell suspension, oxygen and carbon dioxide depleted red blood cells, oxygen depleted red blood cells, and plasma.

16. The method of claim 14, wherein said addition gas is selected from the group consisting of oxygen, carbon dioxide, nitric oxide, and combinations thereof.

17. The method of claim 14, wherein said increased level of gas is a physiological level of oxygen bound to hemoglobin.

18. The method of claim 14, wherein said blood product flows through a red blood cell editing device.

19. The method of claim 18, wherein said blood product is selected from the group consisting of a red blood cell suspension and packed red blood cells.

* * * * *